United States Patent
Niyikiza et al.

(10) Patent No.: US 12,178,882 B2
(45) Date of Patent: *Dec. 31, 2024

(54) ALPHA POLYGLUTAMATED PEMETREXED AND USES THEREOF

(71) Applicant: L.E.A.F. HOLDINGS GROUP LLC, Gulph Mills, PA (US)

(72) Inventors: Clet Niyikiza, Gulph Mills, PA (US); Victor Mandla Moyo, Ringoes, NJ (US)

(73) Assignee: L.E.A.F. HOLDINGS GROUP LLC, Gulph Mills, PA (US)

( * ) Notice: Subject to any disclaimer, the term of this patent is extended or adjusted under 35 U.S.C. 154(b) by 146 days.

This patent is subject to a terminal disclaimer.

(21) Appl. No.: 17/544,191

(22) Filed: Dec. 7, 2021

(65) Prior Publication Data

US 2022/0088219 A1 Mar. 24, 2022

Related U.S. Application Data

(63) Continuation of application No. 16/324,823, filed as application No. PCT/US2017/046666 on Aug. 12, 2017, now Pat. No. 11,344,628, which is a continuation of application No. 15/675,701, filed on Aug. 11, 2017, now abandoned, and a continuation of application No. 15/675,695, filed on Aug. 11, 2017, now abandoned.

(60) Provisional application No. 62/374,458, filed on Aug. 12, 2016.

(51) Int. Cl.
| | |
|---|---|
| *A61K 47/69* | (2017.01) |
| *A61K 9/127* | (2006.01) |
| *A61K 31/517* | (2006.01) |
| *A61K 31/519* | (2006.01) |
| *A61K 45/06* | (2006.01) |
| *A61K 47/10* | (2017.01) |
| *A61K 47/54* | (2017.01) |
| *A61K 47/64* | (2017.01) |
| *A61K 47/68* | (2017.01) |
| *A61P 19/02* | (2006.01) |
| *A61P 35/00* | (2006.01) |
| *C07K 16/28* | (2006.01) |
| *B82Y 5/00* | (2011.01) |

(52) U.S. Cl.
CPC ........ *A61K 47/6913* (2017.08); *A61K 9/1271* (2013.01); *A61K 31/517* (2013.01); *A61K 31/519* (2013.01); *A61K 45/06* (2013.01); *A61K 47/10* (2013.01); *A61K 47/545* (2017.08); *A61K 47/64* (2017.08); *A61K 47/645* (2017.08); *A61K 47/6801* (2017.08); *A61K 47/6849* (2017.08); *A61K 47/6911* (2017.08); *A61P 19/02* (2018.01); *A61P 35/00* (2018.01); *C07K 16/28* (2013.01); *A61K 2300/00* (2013.01); *B82Y 5/00* (2013.01); *C07K 2317/73* (2013.01)

(58) Field of Classification Search
CPC ............ A61K 47/6913; A61K 47/6911; A61K 47/645; A61K 47/545; A61K 47/64; A61K 47/6849; A61K 47/6801; A61K 9/1271; A61K 31/517; A61K 31/519; A61K 45/06; A61K 47/10; A61K 2300/00; A61P 35/00; C07K 16/28; C07K 2317/73; B82Y 5/00
See application file for complete search history.

(56) References Cited

U.S. PATENT DOCUMENTS

| | | | |
|---|---|---|---|
| 4,584,375 A | 4/1986 | Coward | |
| 5,268,362 A | 12/1993 | Akimoto et al. | |
| 5,912,251 A | 6/1999 | Nair | |
| 6,569,432 B1 | 5/2003 | Israeli et al. | |
| 7,053,065 B2 | 5/2006 | Niyikiza et al. | |
| 7,399,461 B2 * | 7/2008 | Heston ........... | A61K 39/001195 424/9.44 |
| 7,446,120 B2 | 11/2008 | Gour et al. | |
| 7,772,209 B2 | 8/2010 | Niyikiza | |
| 8,466,111 B2 | 6/2013 | Jansen et al. | |
| 8,747,869 B2 | 6/2014 | Irvine et al. | |
| 9,207,238 B2 | 12/2015 | Ando et al. | |
| 9,261,509 B2 | 2/2016 | Dervieux | |
| 9,440,979 B2 | 9/2016 | Lahiri et al. | |
| 11,244,628 B2 | 2/2022 | Cho et al. | |
| 11,344,628 B2 | 5/2022 | Niyikiza et al. | |
| 11,534,498 B2 | 12/2022 | Niyikiza et al. | |
| 11,701,432 B2 | 7/2023 | Niyikiza et al. | |

(Continued)

FOREIGN PATENT DOCUMENTS

| | | |
|---|---|---|
| CN | 103040748 A | 4/2013 |
| RU | 2423114 C2 | 2/2011 |

(Continued)

OTHER PUBLICATIONS

International Search Report for PCT/US2019/016955, mailed Apr. 24, 2019, 4 pages.

(Continued)

*Primary Examiner* — Michael P Cohen
(74) *Attorney, Agent, or Firm* — Nixon & Vanderhye, PC

(57) ABSTRACT

The disclosure relates generally to polyglutamated antifolates, formulations containing liposomes filled with alpha or D-gamma polyglutamated antifolates, methods of making the polyglutamated antifolates and liposome containing formulations, and methods of using polyglutamated antifolates and liposome containing formulations to treat hyerproliferative disorders (e.g., cancer) and disorders of the immune system (e.g., an autoimmune disease such as rheumatoid arthritis).

19 Claims, 15 Drawing Sheets

(56) References Cited

U.S. PATENT DOCUMENTS

| | | |
|---|---|---|
| 11,779,584 B2 | 10/2023 | Niyikiza et al. |
| 2001/0046533 A1 | 11/2001 | Bailey et al. |
| 2003/0125302 A1 | 7/2003 | Lu et al. |
| 2004/0001846 A1 | 1/2004 | Israeli et al. |
| 2004/0175834 A1 | 9/2004 | Dervieux et al. |
| 2005/0031679 A1 | 2/2005 | Clemens et al. |
| 2005/0163832 A1 | 7/2005 | Torchilin |
| 2006/0063768 A1 | 3/2006 | Mueller et al. |
| 2006/0067368 A1 | 3/2006 | Ballester et al. |
| 2006/0111272 A1 | 5/2006 | Roberts et al. |
| 2006/0160751 A1 | 7/2006 | McGuire |
| 2006/0222696 A1 | 10/2006 | Okada et al. |
| 2007/0116753 A1 | 5/2007 | Hong et al. |
| 2007/0270431 A1 | 11/2007 | Tabunoki et al. |
| 2007/0280880 A1 | 12/2007 | Moser et al. |
| 2008/0214585 A1 | 9/2008 | Roberts et al. |
| 2008/0260812 A1 | 10/2008 | Matsuyama et al. |
| 2009/0155345 A1 | 6/2009 | Barenholz et al. |
| 2009/0234298 A1 | 9/2009 | Habeshaw et al. |
| 2010/0203539 A1 | 8/2010 | Dervieux |
| 2010/0266709 A1 | 10/2010 | Hicks |
| 2011/0280932 A1 | 11/2011 | Garcia et al. |
| 2012/0077784 A1 | 3/2012 | Whitbourne |
| 2012/0142692 A1 | 6/2012 | Roberts |
| 2012/0252816 A1 | 10/2012 | Chen et al. |
| 2012/0258450 A1 | 10/2012 | Norfray |
| 2013/0122096 A1 | 5/2013 | Shemi et al. |
| 2013/0165654 A1 | 6/2013 | Kadaboina et al. |
| 2013/0177570 A1 | 7/2013 | Low et al. |
| 2013/0259922 A1 | 10/2013 | Haas et al. |
| 2013/0324727 A1 | 12/2013 | Tarnchompoo et al. |
| 2014/0086939 A1 | 3/2014 | Karin et al. |
| 2014/0120157 A1 | 5/2014 | Chang et al. |
| 2014/0315920 A1 | 10/2014 | Virca et al. |
| 2015/0239956 A1 | 8/2015 | Koguma et al. |
| 2016/0228573 A1 | 8/2016 | Niyikiza et al. |
| 2018/0236098 A1 | 8/2018 | Niyikiza et al. |
| 2019/0224334 A1 | 7/2019 | Niyikiza et al. |
| 2020/0360388 A1 | 11/2020 | Niyikiza et al. |
| 2021/0038719 A1 | 2/2021 | Niyikiza et al. |
| 2021/0052592 A1 | 2/2021 | Niyikiza et al. |
| 2021/0128469 A1 | 5/2021 | Niyikiza et al. |
| 2021/0154196 A1 | 5/2021 | Niyikiza et al. |
| 2021/0161899 A1 | 6/2021 | Niyikiza et al. |
| 2021/0169887 A1 | 6/2021 | Niyikiza et al. |
| 2021/0220494 A1 | 7/2021 | Bradbury et al. |
| 2021/0338675 A1 | 11/2021 | Niyikiza et al. |
| 2022/0088219 A1 | 3/2022 | Niyikiza et al. |
| 2022/0279831 A1 | 9/2022 | Perrin et al. |

FOREIGN PATENT DOCUMENTS

| | | | |
|---|---|---|---|
| WO | WO-1985005453 A1 | 12/1985 | |
| WO | WO-200002938 A2 | 1/2000 | |
| WO | WO2001005405 A1 | 1/2001 | |
| WO | WO-200195884 A2 | 12/2001 | |
| WO | WO-2004087115 A2 | 10/2004 | |
| WO | WO-2005070465 A2 | 8/2005 | |
| WO | WO-2005089767 A1 | 9/2005 | |
| WO | WO-2011106528 A2 | 9/2005 | |
| WO | WO-2006002049 A2 | 1/2006 | |
| WO | WO-2006029385 A2 | 3/2006 | |
| WO | WO-2006074416 A1 | 7/2006 | |
| WO | WO-2007023243 A2 | 3/2007 | |
| WO | WO-2007098089 A2 | 8/2007 | |
| WO | WO-2008030818 A2 | 3/2008 | |
| WO | WO-2008083107 A2 * | 7/2008 | ........... A61K 31/131 |
| WO | WO-2009153575 A1 | 12/2009 | |
| WO | WO-2011143484 A1 | 11/2011 | |
| WO | WO-2011150392 A1 | 12/2011 | |
| WO | WO-2012061469 A2 | 5/2012 | |
| WO | WO-2012061759 A2 | 5/2012 | |
| WO | WO2012118806 A2 | 9/2012 | |
| WO | WO-2013008240 A2 | 1/2013 | |
| WO | WO-2013012722 A1 | 1/2013 | |
| WO | WO-2014046630 A1 | 3/2014 | |
| WO | WO-2014186403 A2 | 11/2014 | |
| WO | WO-2016025882 A2 * | 2/2016 | ........... A61K 31/519 |
| WO | WO-2017123517 A1 | 7/2017 | |
| WO | WO-2018031967 A1 | 2/2018 | |
| WO | WO-2018031968 A1 | 2/2018 | |
| WO | WO-2018031979 A1 | 2/2018 | |
| WO | WO-2018031980 A1 | 2/2018 | |
| WO | WO-2019094648 A1 | 5/2019 | |
| WO | WO-2019157120 A1 | 8/2019 | |
| WO | WO-2019157121 A1 | 8/2019 | |
| WO | WO-2019157123 A1 | 8/2019 | |
| WO | WO-2019157125 A1 | 8/2019 | |
| WO | WO-2019157129 A1 | 8/2019 | |
| WO | WO-2019157133 A1 | 8/2019 | |
| WO | WO-2019157138 A1 | 8/2019 | |
| WO | WO-2019157140 A1 | 8/2019 | |
| WO | WO-2019157145 A1 | 8/2019 | |
| WO | WO-2019157146 A1 | 8/2019 | |
| WO | WO-2019157148 A1 | 8/2019 | |
| WO | WO-2019160732 A1 | 8/2019 | |
| WO | WO-2019160733 A1 | 8/2019 | |
| WO | WO-2019160734 A1 | 8/2019 | |
| WO | WO-2019160735 A1 | 8/2019 | |
| WO | WO-2019160736 A1 | 8/2019 | |
| WO | WO-2021026310 A1 | 2/2021 | |

OTHER PUBLICATIONS

Written Opinion of the ISA for PCT/US2019/016955, mailed Apr. 24, 2019, 5 pages.

Assaraf, Y. G., et al., "Characterization of the Coexisting Multiple Mechanisms of Methotrexate Resistance in Mouse 3T6 R50 Fibroblasts." J. Biological Chemistry, 267(9):5776-5784 (1992).

Banerjee, D., et al., "Molecular mechanisms of resistance to antifolates, a review." Acta Biochim Pol., 42(4):457-464 (1995).

Bertino, J. R., et al., "Resistance Mechanisms to Methotrexate in Tumors." Stem Cells, 14:5-9 (1996).

Bozzuto, G., et al., "Liposomes as nanomedical devices," Intl. J. Nanomed. 10:975-999 (2015).

Bulbake, U., et al., "Liposomal Formulations in Clinical Use: An Updated Review." Pharmaceutics, 9(12):1-33 (2017).

Chabner, B. A., et al., "Polyglutamation of Methotrexate is Methotrexate a Prodrug?" Journal of Clinical Investigation, 76:907-912 (1985).

Chazal, M., et al., "Decreased Folylpolyglutamate Synthetase Activity in Tumors Resistant to Fluorouracil-Folinic Acid Treatment: Clinical Data." Clinical Cancer Research, 3:553-557 (1997).

Danenberg, P. V., et al., "Folates as adjuvants to anticancer agents: Chemical rationale and mechanism of action." Crit Rev. Oncol. Hematol., 106:118-131. (2016).

Delfino, R. T., et al., "Type 2 Antifolates in the Chemotherapy of falciparum Malaria." J. Braz. Chem. Soc., 13(6):727-741 (2002).

Deshpande, P., et al., "Current trends in the use of liposomes for tumor targeting." Nanomedicine (Lond), 8(9):1-32 (2013).

Desmoulin, S. K., et al., "The human proton-coupled folate transporter." Cancer Biology & Therapy, 13(14):1355-1373; (2012).

Faessel, H. M., et al., "Super in Vitro Synergy between Inhibitors of Dihydrofolate Reductase and Inhibitors of Other Folate-requiring Enzymes: The Critical Role of Polyglutamylation." Cancer Research, 58:3036-3050 (1998).

Fan, Y., et al., "Development of liposomal formulations: From concept to clinical investigations." Asian Journal of Pharmaceutical Sciences, 8(2):81-87 (2013).

Fouladi, F., et al., "Enzyme-Responsive Liposomes for the Delivery of Anticancer Drug." Bioconjug Chem., 19:28(4): 857-868 (2017).

Galivan, J., et al., "γ-Fluoromethotrexate: Synthesis and biological activity of a potent inhibitor of dihydrofolate reductase with greatly diminished ability to form poly-γ-glutamates." Proc. Natl. Acad. Sci. USA, (82):2598-2602 (1985).

Gonen, N., et al., "Antifolates in cancer therapy: Structure, activity and mechanisms of drug resistance." Drug Resistance Updates, 15:183-210 (2012).

Habeck L. L., et al., "A Novel Class of Monoglutamated Antifolates Exhibits Tight-binding Inhibition of Human Glycinamide Ribonucleotide

(56) References Cited

OTHER PUBLICATIONS

Formyltransferase and Potent Activity against Solid Tumors." Cancer Research, 54: 1021-1026 (1994).
Heath, T.D., et al., "Antibody-directed liposomes Determination of affinity constants for soluble and liposome-bound antifluorescein." Biochimica et Biophysica Acta (BBA)—Biomembranes, 770(2):148-158 (1984).
Jackman, A. L., et al., "Folate-based thymidylate synthase inhibitors as anticancer drugs." Annals of Oncology, 6: 871-881 (1995).
Jansen, G., et al., "Folates in rheumatoid arthritis." Pteridines, 24(1): 21-26 (2013).
Kim, S., et al., "Gamma-glutamyl hydrolase modulation and folate influence chemosensitivity of cancer cells to 5-fluorouracil and methotrexate." British Journal of Cancer, 109:2175-2188 (2013).
Kremer, J.M. "Toward a Better Understanding of Methotrexate." Arthritis & Rheumatism, 50:1370-1382 (2004).
Kuehl, M., et al., "Cytotoxicity, Uptake, Polyglutamate Formation, and Antileukemic Effects of 8-Deaza Analogues of Methotrexate and Aminopterin in Mice." Cancer Research, 48:1481-1488 (1988).
Ledermann, J. A., et al., "Targeting the folate receptor: diagnostic and therapeutic approaches to personalize cancer treatments." Annals of Oncology, 26:2034-2043 (2015).
Li, J., et al., "A review on phospholipids and their main applications in drug delivery systems." Asian Journal of Pharmaceutical Science, 10(2):81-98 (2015).
Lila, A. S., et al., "Liposomal Delivery Systems: Design Optimization and Current Applications." Biol. Pharm. Bull., 40:1-10 (2017).
Matherly, L. H., et al., "The Major Facilitative Folate Transporters Solute Carrier 19A1 and Solute Carrier 46A1: Biology and Role in Antifolate Chemotherapy of Cancer." Drug Metabolism and Disposition, 42:632-649 (2014).
McCloskey, D. E., et al.,. "Decreased Folylpolyglutamate Synthetase Activity as a Mechanism of Methotrexate Resistance in CCRF-CEM Human Leukemia Sublines." J. Biological Chemistry, 266(10):6181-6187 (1991).
Muhale, F., et al., "Systems pharmacology assessment of the 5-fluorouracil pathway." Pharmacogenomics, 12(3): 341-350 (2011).
Obeid, R., et al, "Is 5-methyltetrahydrofolate an alternative to folic acid for the prevention of neural tube defects?" J. Perinat. Med., 41(5): 469-483 (2013).
Pavlova, N. N., et al., "The Emerging Hallmarks of Cancer Metabolism." Cell Metab., 12;23(1):27-47 (2016).
Reeve, S. M., et al., "Charged Propargyl-Linked Antifolates Reveal Mechanisms of Antifolate Resistance and Inhibit Trimethoprim-Resistant MRSA Strains Possessing Clinically Relevant Mutations." J. Med. Chem., 59:6493-6500 (2016).
Rhee, M. S., et al., "Acquisition of Resistance to Antifolates Caused by Enhanced y-Glutamyl Hydrolase Activity." Cancer Research, 53: 2227-2230 (1993).
Rots, M. G., et al., "Role of Folylpolyglutamate Synthetase and Folylpolyglutamate Hydrolase in Methotrexate Accumulation and Polyglutamylation in Childhood Leukemia." Blood, 93(5):1677-1683 (1999).
Samuels, L.S., et al., "Similar Differential for Total Polyglutamylation and Cytotoxicity among Various Folate Analogues in Human and Murine Tumor Cells in Vitro." Cancer Research, 45:1488-1495 (1985).
Ser, A., et al., "Targeting One Carbon Metabolism with an Antimetabolite Disrupts Pyrimidine Homeostasis and Induces Nucleotide Overflow." Cell Reports, 15(11): P2367-2376 (2016).
Shih, C., et al., "LY231514, a Pyrrolo[2,3-d]pyrimidine-based Antifolate That Inhibits Multiple Folate-requiring Enzymes." Cancer Research, 57:1116-1123 (1997).
Shimamoto, Y., et al., "Association between mRNA expression of chemotherapy-related genes and clinicopathological features in colorectal cancer: A large-scale population analysis." International Journal of Molecular Medicine, 37:319-328 (2016).
Shrestha, H., et al., "Lipid-Based Drug Delivery Systems." Journal of Pharmaceutics, 1-10 (2014).
Stathopoulos, G. P., et al., "Lipoplatin Formulation Review Article." Journal of Drug Delivery, 1-10 (2012).
Torchilin, V, P., "Recent Advances with Liposomes as Pharmaceutical Carriers." Nature Reviews Drug Discovery, 4:145-160 (2005).
Tsukioka, S., et al., "In vivo evidence for a significant role of folylpolyglutamate synthase in combined chemotherapy with oral fluoropyrimidine, UFT or S-1, and leucovorin." Oncology Reports 25:1407-1412 (2011).
Van Triest, B., et al., "Thymidylate Synthase Level as the Main Predictive Parameter for Sensitivity to 5-Fluorouracil, but not for Folate-based Thymidylate Synthase Inhibitors, in 13 Nonselected Colon Cancer Cell Lines." Clinical Cancer Research, 5:643-654 (1999).
Verma, M. S., "1,3-Beta-Glucans: Drug Delivery and Pharmacology." The Complex WO-rld of Polysaccharides, Chapter 21:551-572 (2012).
Visentin, M., et al., "The Antifolates." Hematol. Oncol. Clin. North Am., 26(3): 629-ix (2012).
Wagner, A. and Vorauer-Uhl, K., "Liposome Technology for Industrial Purposes," Journal of Drug Delivery, vol. 2011, Article ID 591325, 9 pages (2011).
Whitehead, V. M., et al., "Accumulation of Methotrexate and Methotrexate Polyglutamates in Lymphoblasts at Diagnosis of Childhood Acute Lymphoblastic Leukemia: A Pilot Prognostic Factor Analysis." Blood, 76(1):44-49 (1990).
Wilson, M. R., et al., "Targeting Nonsquamous Non small Cell Lung Cancer via the Proton-Coupled Folate Transporter with 6-Substituted Pyrrolo [2,3-d]Pyrimidine Thienoyl Antifolates." Mol. Pharmacol., 89:425-434 (2016).
Wojtuszkiewicz, A., et al., ""Methotrexate resistance in relation to treatment outcome in childhood acute lymphoblastic leukemia."" J Hematol Oncol., 8:61 (2015).
Molina, et al., "The role of Pemetrexed in Lung Cancer Therapy", Clinical Lung Cancer 5:21 (2003).
Tomsho, et al., "Concentration-dependent processivity of multiple glutamate ligations catalyzed by foly-poly-gamma-glutamate synthetase" Biochemistry 47(34):9040 (2008).
Tomsho et al., "Synthesis of (6R)- and (6S)-5, 10-dideazatetrahydrofolate oligo-γ-glutamates: Kinetics of multiple glutamate ligations catalyzed by folylpoly-γ-glutamate synthetase" Org. Biomol. Chem. 3(18):3388-98 (2005).
Besson et al., "Effects of tetrahydrofolate polyglutamates on the kinetic parameters of serine hydroxymethyltransferase and glycine decarboxylase from pea leaf mitochondria" Biochem J. (Pt 2)(Pt 2):425 (1993).
Tsushima et al., "Fluorine containing amino acids and their derivatives. 7. Synthesis and antitumor activity of α- and γ-substituted methotrexate analogs" Tetrahedron 44(77):5375 (1988).
Duch et al., "Biochemical and Cellular Pharmacology of 1843U89, a Novel Benzoquinazoline Inhibitor of Thymidylate Synthase" Cancer Research 53:810-818 (1993).
Matherly et al., "Enhanced Polyglutamylation of Aminopterin Relative to Methotrexate in the Ehrlich Ascites Tumor Cell in Vitro" Cancer Research 45:1073 (1985).
Fry et al., "Rapid formation of poly-γ-glutamyl derivatives of methotrexate and their association with dihydrofolate reductase as assessed by high pressure liquid chromatography in the Ehrlich ascites tumor cell in vitro" J. Biol. Chem. 257(4): 1980-1986 (1982).
National Center for Biotechnology Information (2020). PubChem Compound Summary for CID 101607589. Retrieved Nov. 22, 2020 from https://pubchem.ncbi.nlm.nih.gov/compound/101607589.
National Center for Biotechnology Information (2020). PubChem Compound Summary for CID 267606. Retrieved Nov. 22, 2020 from https://pubchem.ncbi.nlm.nih.gov/compound/101607589.
National Center for Biotechnology Information (2020). PubChem Compound Summary for CID 102483590. Retrieved Nov. 22, 2020 from https://pubchem.ncbi.nlm.nih.gov/compound/101607589.
Zwicke et al., "Utilizing the folate receptor for active targeting of cancer nanotherapeutics" Nano Reviews 3(1):18496 (2012).

(56) References Cited

OTHER PUBLICATIONS

Springer et al. "Prodrugs of thymidylate synthase inhibitors potential for antibody directed enzyme prodrug therapy (Adept)", Anti-Cancer Drug Design, Oxford University Press, Basingstoke 11(8):625-636 (1996).
Anonymous, "Antifolate—Wikipedia" (Dec. 29, 2020), pp. 1-5, Retrieved from the Internet: URL:https://en.wikipedia.org/wiki/Antifolate [retrieved on Mar. 29, 2021].
Abolmaali et al., A review of therapeutic challenges and achievements of methotrexate delivery systems for treatment of cancer and rheumatoid arthritis Cancer Chemotherapy and Pharmacology 71:1115-1130 (2013).
Jackman et al., "ICI D1694, a Quinazoline Antifolate Thymidylate Synthase Inhibitor That is a Potent Inhibitor of L1210 Tumor Cell Growth in Vitro and in Vivo: A New Agent for Clinical Study." Cancer Research 51:5579-5586 (1991).
Database Biosis [Online] Biosciences Information Service, Philadelphia, PA, US;Jackman A L et al: "ICI D1694, a Quinazoline Antifolate Thymidylate Synthase Inhibitor That is a Potent Inhibitor of L1210 Tumor Cell Growth in Vitro and in Vivo: A New Agent for Clinical Study", XP002341574, retrieved from BIOSIS Database accession No. PREV199293007206 * abstract *.
Pawelczak et al., "Quinazoline 1-41 antifolates inhibiting thymidylate synthase: synthesis of four oligo(L-.gamma.-glutamyl) conjugates of N10-propargyl-5,8-dideazafolic acid and Their enzyme inhibition", J. Med. Chem. 32(1):160-165 (1989).
Michalak et al., "Synthesis and 42-82 Physicochemical Characterization of the Impurities of Pemetrexed Disodium, an Anticancer Drug", Molecules, 20(6):10004-10031 (2105).
Meesters et al., "Assessment of intracellular methotrexate and methotrexate-polyglutamate metabolite concentrations in erythrocytes by ultrafast matrix-assisted laser desorption/ionization triple quadrupole tandem mass spectrometry", 25(20):3063-3070 (2011).
Pitts et al., "Interaction energy analyses of folate analog binding to human dihydrofolate reductase: contribution of the antifolate substructural regions to complex stability", Drug Metabol. Drug Interact. 16(2):99-121 (2000).
Ng et al., "Liposome-dependent 1-15 delivery of pteridine antifolates: a two-compartment growth inhibition assay for evaluating drug leakage and metabolism", Biochimica et Biophysica Acta, 98(2):261-268 (1989).
Chattopadhyay et al., "Pemetrexed: biochemical and cellular pharmacology, mechanisms, and clinical applications", Molecular Cancer Therapeutics 6(2):404-417 (2007).
Abraham et al., "Folate analogs. 33. Synthesis of folate and antifolate poly-.gamma.-glutamates by [(9-fluorenylmethoxy)oxy]carbonyl chemistry and biological evaluation of certain methotrexate polyglutamate polylysine conjugates as inhibitors of the growth of H35 hepatoma cells", J. Med. Chem. 33(2):711-717 (1990).
Khan et al., "Methotrexate: a detailed review on drug delivery and clinical aspects", Expert Opinion on Drug Delivery 9(2) 151-169 (2012).
Lachelt et al., Syntheic polyglutamylation of dual-functional MTX ligands for enhanced combined cytotoxicity of poly(I:C) nanoplexes, Molecular Pharmaceutics (118): 2631-2639 (2014).
Piper et al., "Syntheses of. alpha.- and. gamma.- substituted amides, peptides, and esters of methotrexate and their evaluation as inhibitors of folate metabolism" J. Med. Chem. 25( 2): 182-187 (1982).
Schultz, R. M., "Preclinical development of Alimta (Pemetrexed, LY231514), a multitargeted antifolate", Progress in Drug Research, vol. 63, pp. 275-300. DOI: https://doi.org/10.1007/3-7643-7414-4_11, published in 2005.
Szabo et al., "Cell-penetrating conjugates of pentaglutamylated methotrexate as potential anticancer drugs against resistant tumor cells" European Journal of Medicinal Chemistry 115:361-368 (2016).
SciFinder® substance search alpha methotrexate diglutamate; Oct. 13, 2020 (Year 2020).
Goolge Scholar Search—Shih pemetrexed Oct. 13, 2020 (Year: 2020).
Barenholz, Y "Doxil®—The first FDA-approved nano-drug: Lessons learned" J. Controlled Release 160(2):117-134 (2012).
Barrueco et al., "Facilitated Transport of Methotrexate Polyglutamates into Lysosomes Derived from S180 Cells." The Journal of Biological Chemistry, 267(28): 19986-19991 (1992).
Eldin et al., Encapsulation in a rapid-release liposomal formulation enhances the anti-tumor efficacy of pemetrexed in a murine solid mesothelioma-xenograft model "European Journal of Pharmaceutical Sciences, 81:" 60-66 (2016).
Immordino et al., ""Stealth liposomes: review of the basic science, rationale, and clinical applications, existing and potential."" Intl. J. Nanomed. 1 (3):297-315 (2006).
Marchi et al., "Pralatrexate Pharmacology and Clinical Development," Clin. Cancer Res. 19(24):6657-6661 (2013).
Heinrich et al., "Comparison of the results obtained by ELISA and surface plasmon resonance for the determination of antibody affinity," Journal of Immunological Methods, 352:13-22 (2010).
Langer et al., "Carboplatin and pemetrexed with or without pembrolizumab for advanced, non-squamous non-small-cell lung cancer: a randomised, phase 2 cohort of the open-label Keynote-021 study," Lancet Oncol. 17:1497-1508 (2016).
Nagai et al., "Production of a High-affinity Monoclonal Antibody Reactive with Folate Receptors Alpha and BetaMonoclonal Antibodies in Immunodiagnosis and Immunotherapy," 34(3):181-190 (2015); doi.org/10.1089/mab.2014.0072.
Nair et al., "Synthesis and biological evaluation of poly-.gamma.-glutamyl metabolites of 10-deazaaminopterin and 10-ethyl-10-deazaaminopterin," J. Med. Chem. 31:181-185 (1988).
Piper et al., "A synthetic approach to poly(.gamma.-glutamyl) conjugates of methotrexate" J. Med. Chem. 26(2):291-294 (1983).
Piper et al., "Synthesis and antifolate activity of 5-methyl-5, 10-dideaza analogs of aminopterin and folic acid and an alternative synthesis of 5,10-dideazatetrahydrofolic acid, a potent inhibitor of glycinamide ribonucleotide formyltransferase," J. Med. Chem. 31(11):2164-9 (1988);doi: 10.1021/jm00119a018. PMID: 3184124.
Rosowsky et al., "Synthesis and in Vitro Antifolate Activity of Rotationally Restricted Aminopterin and Methotrexate Analogues," Medicinal Chemistry 47:6958-6963 (2004).
Raz et al., "Folylpoly-γ-glutamate synthetase: A key determinant of folate homeostasis and antifolate resistance in cancer," Drug Resistance Updates, 28:43-64 (2016).
Sulciner et al., "Resolvins suppress tumor growth and enhance cancer therapy," Journal of Experimental Medicine 215(1):115-140 (2018).
Pan et al., Pharmacology and Chemotherapy), Edition I, p. 102 paragraph 5 (Feb. 2000).
Sakamoto et al., "Folylpolyglutamate synthase and γ-glutamyl hydrolase regulate leucovorin-enhanced 5-fluorouracil anticancer activity," Biochem. and Biophys. Res. Comm. 365(4):801-807 (2008), ISSN 0006-291X.
Paiardini et al., "Screening and In Vitro Testing of Antifolate Inhibitors of Human Cytosolic Serine Hydroxymethyltransferase," ChemMedChem. 10(3): 490-497 (2015); doi:10.1002/cmdc.201500028.
Schwendener chapt. 9, Liposomes in Biology and Medicine, 117-128 (2007).
Hobl et al., "A short-chain methotrexate polyglutamate as outcome parameter in rheumatoid arthritis patients receiving methotrexate," Clin. Exp. Rheum. 30:156-163 (2012).
Purcell et al., "Novel antifolate Drugs," Curr. Oncology Reports, Curr. Science, 5(2):114-125 (2003).
Jolivet et al., "Synthesis, Retention, and Biological Activity of Methotrexate Polyglutamates in Cultured Human Breast Cancer Cells," The Journal of Clinical Investigation, 70:351-360 (1982).
Pignatello et al., "Effect of Liposomal Delivery on In Vitro Anti-tumor Activity of Lipophilic Conjugates of Methotrexate with Lipoamino Acids," Drug Delivery 10:95-100 (2003).
Selim, A., et al., "Liposomal Delivery Systems: Design Optimization and Current Applications," Biol. Pharm. Bull. 40:1-10 (2017).
Shmeeda, H., et al., "Intracellular uptake and intracavitary targeting of folate-conjugated liposomes in a mouse lymphoma model with up-regulated folate receptors," Mol. Cancer Ther., 5(4):818-824 (2006).

(56) References Cited

OTHER PUBLICATIONS

Tseng, Y-L, et al., "Translocation of Liposomes into Cancer Cells by CellPenetrating Peptides Penetratin and Tat: A Kinetic and Efficacy Study," Mol. Pharmacol. 62:864-872 (2002).

Lehtinen, J., et al., "Pre-Targeting and Direct Immunotargeting of Liposomal Drug Carriers to Ovarian Carcinoma," PLOS One, 7(7): 1-10 (2012).

Li, T., "A novel application of maleimide for advanced drug delivery: in vitro and in vivo evaluation of maleimide-modified pH-sensitive liposomes," Intl J. Nanomed.8:3855-3866 (2013).

Li, Y., "Self-assembly of multifunctional integrated nanoparticles loaded with a methotrexate-phospholipid complex: combining simplicity and efficacy in both targeting and anticancer effects," RSC Ad., 6:86717 (2016).

Paolino et al., "Gemcitabine-loaded PEGylated unilamellar liposomes vs Gemzar®: Biodistribution, pharmacokinetic features and in vivo antitumor activity," J Controlled Release 144:144-150 (2010).

Pasut, G., et al., "Antitumoral activity of PEG-gemcitabine prodrugs targeted by folic acid," J. Controlled Rel. 127:239-248 (2008).

Varshochian, et al., "Utilizing liposomes and lipid nanoparticles to overcome challenges in breast cancer treatment," Clin. Lipidol. 9(5), 571-585 (2014).

Wibowo, A., et al., "Structures of human folate receptors reveal biological trafficking states and diversity in folate and antifolate recognition," PNAS 110(38):15180-15188 (2013).

Rhee, et al., "Glutamyl hydrolase and the multitargeted antifolate LY231514," Cancer Chemother. Pharmacol., 44:427-432 (1999).

Chan et al., Advances in Experimental Medicine and Biology, vol. 620, Biochem. J. (1986) 236, 193-200 (Printed in Great Britain) (2007).

Fiehn C: "The future of methotrexate therapy and other folate inhibitors", Zeitschrift Fur Rheumatologie, Springer, DE, vol. 70, No. 2, Jan. 27, 2011 (Jan. 27, 2011), pp. 129-134, XP036030662, ISSN: 0340-1855, DOI: 10.1007/S00393-010-0688-Z.

Alexis et al: "Nanoparticle technologies for cancer therapy", Jan. 1, 2010 (Jan. 1, 2010, Drug Delivery In: Handbook of Experimental Pharmacology; vol. 197; pp. 55-86, ISSN 0171-2004; XP008182266.

Allegra et al., "Enhanced Inhibition of Thymidylate Synthase by Methotrexate Polyglutamates," J. Biological Chemistry, 260(17):9720-9726 (1985).

Beutel et al., "Phase I study of OSI-7904L, a novel liposomal thymidylate synthase inhibitor in patients with refractory solid tumors," Clinical Cancer Research 11, 5487-5495 (2005).

Boechat et al., "Methotrexate-loaded lipid-core nanocapsules are highly effective in the control of inflammation in synovial cells and a chronic arthritis model," Intl. J. Nanomed. 10:6603-6614 (2015).

Desjardins et al., "Pharmacokinetics, safety, and efficacy of a liposome encapsulated thymidylate synthase inhibitor, OSI-7904L [(S)-2-[5-[(1,2-dihydro-3-methyl-1-oxobenzo [f] quinazolin-9-yl)methyl]amino-1-oxo-2-isoindolynl]-glutaric acid] in mice," Journal of Pharmacology and Experimental Therapeutics, 309(3):894-902 (2004).

Baggot et al., "Inhibition of 5-aminoimidazole-4-carboxamide ribotide transformylase, adenosine deaminase and 5'-adenylate deaminase by polyglutamates of methotrexate and oxidized folates and by 5-aminoimidazole-4-carboxamide riboside and ribotide," Biochem. J., 236:193-200 (1986).

\* cited by examiner

Exemplary polyglutamated antifolates

PMX-[glutamyl]$_n$

MTX-[glutamyl]$_n$

LTX-[glutamyl]$_n$

RTX-[glutamyl]$_n$ piritrexim-[glutamyl]$_n$ pralatrexate-[glutamyl]$_n$

AG2034-[glutamyl]$_n$

GW1843-[glutamyl]$_n$ aminopterin-[glutamyl]$_n$

LY309887-[glutamyl]$_n$

Wherein: each glutamyl (even in the same molecule) can be independently

D-gamma-glutamic acid,

L-alpha glutamic acid, or

D-alpha glutamic acid.

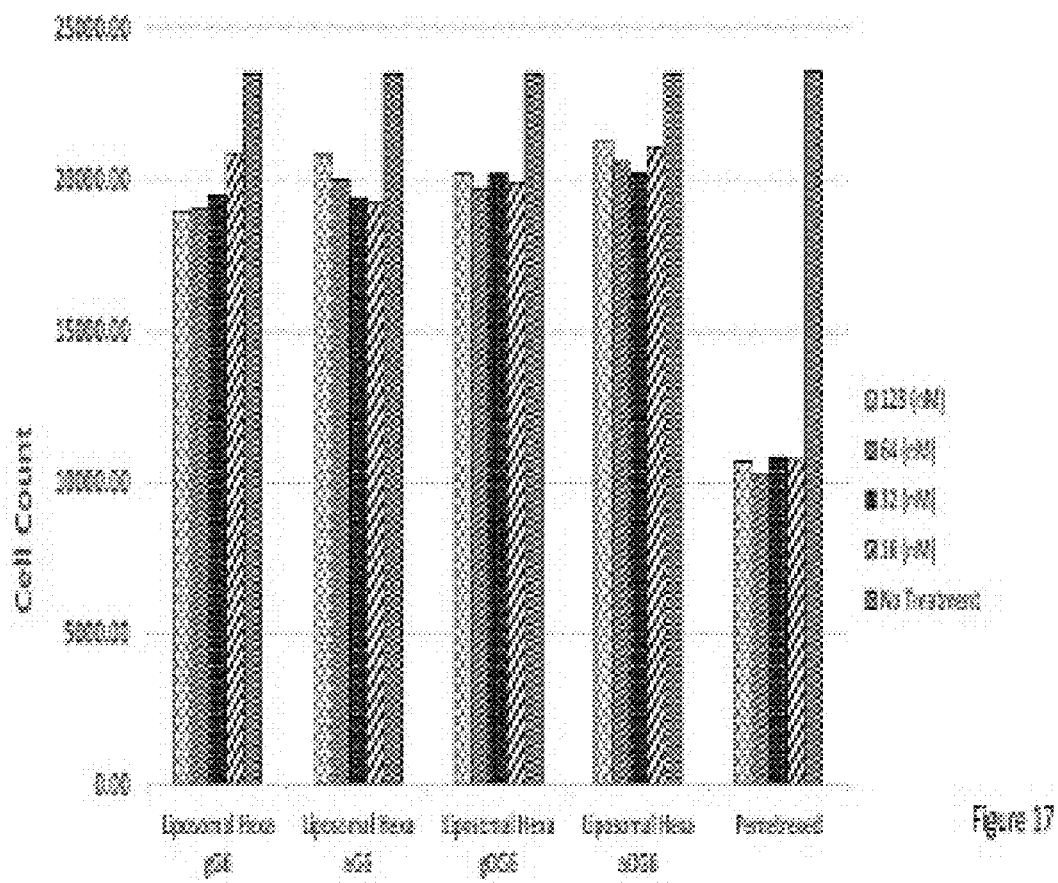

ALPHA POLYGLUTAMATED PEMETREXED AND USES THEREOF

RELATED CASES

This application is a continuation of U.S. application Ser. No. 16/324,823, filed on Feb. 11, 2019, which is the U.S. National Phase of PCT Application No. PCT/US2017/046666, filed on Aug. 12, 2017, based on and claims priority under 35 U.S.C. § 119 to U.S. Provisional Patent application No. 62/374,458, filed on Aug. 12, 2016 in the U.S. Patent and Trademark Office, the entirety of which is incorporated by reference herein. This application also claims priority to U.S. application Ser. No. 15/675,695, filed on Aug. 11, 2017 and U.S. application Ser. No. 15/675,701, filed on Aug. 11, 2017. The contents of each of the U.S. applications are incorporated herein in their entirety. All references, patents and patent applications referred to herein are herein incorporated by reference in their entireties.

BACKGROUND

This disclosure generally relates to alpha and D-gamma polyglutamated antifolate compositions, including delivery vehicles such as liposomes filled with the alpha (L-alpha or D-alpha) or D-gamma polyglutamated antifolates, and methods of making and using the compositions to treat diseases including hyperproliferative diseases such as cancer, disorders of the immune system such as rheumatoid arthritis and infectious diseases such as HIV.

Folates are indispensable for cell growth and tissue regeneration. Mammalian cells do not synthesize folates de novo and rely on extracellular folates taken up by three major folate uptake systems: a reduced folate carrier (RFC) system; a system of folate receptors (FRs) α and β; and a folate symporter (PCFT) system. Antifolates that target folate-dependent biosynthetic pathways function as anti-proliferative agents. Naturally occurring folates exist within cells as polyglutamates through the action of the enzyme folylpolyglutamyl synthetase (FPGS), which may add up to 6 glutamyl groups in a L-gamma peptide linkage to the folate substrate. L gamma polyglutamation serves at least 3 main purposes: (1) it facilitates the accumulation of intracellular folates in vast excess of the monoglutamate pool, which is freely transportable into and out of cells; (2) it allows selective intracellular retention of these relatively large anionic molecules; and (3) it greatly enhances folate cofactor affinity for several folate-dependent enzymes, including thymidylate synthase and AICAR transformylase (see, e.g., FIG. 2).

Antifolates are a class of antiproliferatives that were first developed more than 70 years ago as "folic acid mimic molecule" cytotoxic agents. The rationale was to design a class of molecules that would counter the action of folic acid in fast replicating cells such as cancer cells, taking advantage of physiological folate transport mechanism and their facilitative intracellular mode of action for DNA replication during the cell division. Specifically, antifolates were designed to mimic folic acid in its systemic transport, physiologic cell uptake (e.g., via reduced folate carriers (RFCs) and proton-coupled folate transporters (PCFTs)) and intracellular processing. Antifolates act specifically during DNA and RNA synthesis, exerting a cytotoxic effect during the S-phase of the cell cycle. As a result, they have a greater toxic effect on rapidly dividing cells such as malignant and myeloid cells.

Antifolates are widely recognized for their inhibition of folate metabolism. Major antifolate enzyme targets and exemplary antifolates that target these enzymes include: (a) dihydrofolate reductase (DHFR) [e.g., methotrexate (MTX) and pralatrexate], (b) thymidylate synthase (TS) [e.g., raltitrexed (RTX), GW1843U, and pemetrexed (PMX)], (c) β-glycinamide ribonucleotide formyl transferase (GARFTase) [e.g., lometrexol (LMX), PMX] and (d) 5-aminoimidazole-4-carboxamide ribonucleotide formyl transferase (AICARFTase) [e.g., PMX]. Inhibition of the above enzymes suppresses de novo nucleotide biosynthesis, resulting in an imbalance of purine and pyrimidine precursors and rendering cells incapable of undergoing accurate DNA replication, ultimately resulting in cell death. Accordingly, it is not surprising that inhibitors of the folate metabolism pathway play important roles in treating hyperproliferative diseases including hematologic malignancies and solid tumors, as well as disorders of the immune system such as rheumatoid arthritis.

Each of the above antifolates is transported by the reduced folate carrier (RFC), which is the main transport system at physiologic pH. RFC is ubiquitously expressed in normal and diseased cells, and consequently these drugs suffer from dose-limiting toxicity which is a major obstacle in the chemotherapy of cancer. As such, it is desirable to design targeted antifolates that are selectively taken up by transport systems (other than RFC) which have limited expression and function in normal tissues compared with tumors.

Pemetrexed (sold commercially under the brand name ALIMTA®) is a antifolate containing a 6-5 fused pyrrolo[2,3-d]pyrimidine nucleus that inhibits thymidylate synthase (TS), glycinamide ribonucleotide formyltransferase (GARFT), and dihydrofolate reductase (DHFR), folate-dependent enzymes involved in the synthesis of thymidine and purine nucleotides. Like methotrexate, pemetrexed is transported into cells by the RFC and membrane folate-binding proteins, where it is L gamma polyglutamated by folylpoly-gamma-glutamate synthetase. L gamma polyglutamated forms of pemetrexed have greater intracellular retention and have greater affinity for TS and GARFT compared to pemetrexed monoglutamate. Pemetrexed is approved for the treatment of mesothelioma and non-small lung carcinoma (NSCLC). Myelosuppression is typically the dose-limiting toxicity with pemetrexed therapy and has limited the clinical applications of this drug. Pretreatment with folic acid and vitamin B is now used to ameliorate the most frequent side effects that include bone marrow suppression, fatigue, and skin rash.

One of the challenges of cancer treatment is delivering cytotoxic agents to cancer cells while minimizing and/or reducing the effect of such agents on normal healthy cells. To address the toxicity of antifolates in normal cells, WO 2016/25882 describes liposomal formulations of antifolates that are targeted to cancer cells using, for example, antibodies having a specific affinity for folate receptors expressed by many cancer cells. This formulation can reduce and/or minimize the effects of the antifolates on healthy cells, meaning that patients can experience fewer side effects.

Despite the advances in treating cancer and other hyperproliferative disorders using antifolates, additional compositions and methods are needed for improving the efficacy and decreasing the dose-limiting toxicity associated with antifolate therapy. The present disclosure provides compositions and methods that address these needs.

BRIEF SUMMARY

This disclosure generally relates novel alpha and D-gamma polyglutamated antifolate compositions, including delivery vehicles such as liposomes filled with the alpha and D-gamma polyglutamated antifolates, and methods of making and using the compositions to treat diseases including hyperproliferative diseases such as cancer, disorders of the immune system such as rheumatoid arthritis and infectious diseases such as HIV. The disclosure further relates to alpha and D-gamma pentaglutamated and hexaglutamated antifolate compositions, including delivery vehicles such as liposomes filled with the alpha and/or D-gamma pentaglutamated and hexaglutamated antifolates, and methods of making and using the compositions to treat diseases including hyperproliferative diseases, disorders of the immune system and infectious disease.

By way of example and without limitation, the disclosure describes liposome compositions that contain alpha (e.g., L-alpha and D-alpha) and D-gamma polyglutamated (e.g., pentaglutamated and hexaglutamated) forms of the antifolates MTX, PMX, LTX, AG2034, RTX, piritrexim, pralatrexate, AG2034, GW1843, aminopterin, and LY309887. These compositions provide improvements to the efficacy and safety of delivering antifolates to cancer cells by providing the preferential delivery of a more cytotoxic payload (e.g., polyglutamated antifolates) compared to the cytotoxicity of the corresponding antifolate in its administered monoglutamated state. Therefore, in one aspect the disclosure provided liposomal antifolate composition that is untargeted. That is the liposomal antifolate composition does not have specific affinity towards a specific epitope.

The disclosure also provides targeted liposome compositions (targeted composition comprising liposomal antifolate composition) that contain a targeting moiety having a specific affinity for an epitope (antigen) expressed on the surface of a target cell of interest. The targeted liposomes provide further improvements to the efficacy and safety of delivering antifolates to cancer cells by specifically delivering polyglutamated (e.g., pentaglutamated and hexaglutamated) antifolates to the target cell.

In some embodiments, the disclosure provides a composition comprising an alpha (e.g., L-alpha and D-alpha) or D-gamma polyglutamated antifolate (e.g., pentaglutamated and hexaglutamated). In further embodiments the composition comprises an alpha (e.g., L-alpha and D-alpha) or D-gamma pentaglutamated or hexaglutamated antifolate. According to some embodiments, the alpha (e.g., L-alpha and D-alpha) or D-gamma polyglutamated antifolate is a member selected from the group consisting of: polyglutamated methotrexate (MTX), polyglutamated pemetrexed (PMX), polyglutamated lometrexol (LTX), polyglutamated AG2034, polyglutamated raltitrexed (RTX), polyglutamated piritrexim, polyglutamated pralatrexate, polyglutamated AG2034, polyglutamated GW1843, polyglutamated aminopterin, and polyglutamated LY309887. In further embodiments, the alpha (L-alpha or D-alpha) or D-gamma polyglutamated member is pentaglutamated. In further embodiments, the alpha (L-alpha or D-alpha) or D-gamma polyglutamated member is hexaglutamated.

In one embodiment, the composition comprises an alpha polyglutamated PMX, MTX, RTX, or LTX. In a further embodiment the composition comprises an alpha pentaglutamated PMX, MTX, RTX, or LTX. In a further embodiment the composition comprises an alpha hexaglutamated PMX, MTX, RTX, or LTX.

In one embodiment, the composition comprises an alpha polyglutamated PMX. In a further embodiment the composition comprises an alpha pentaglutamated PMX. In a further embodiment the composition comprises an alpha hexaglutamated PMX.

In another embodiment, the composition comprises an alpha polyglutamated MTX. In a further embodiment the composition comprises pentaglutamated MTX. In a further embodiment the composition comprises hexaglutamated MTX.

In another embodiment, the composition comprises an alpha polyglutamated RTX. In a further embodiment the composition comprises pentaglutamated RTX. In a further embodiment the composition comprises hexaglutamated RTX.

In an additional embodiment, the composition comprises an alpha polyglutamated LTX. In a further embodiment the composition comprises pentaglutamated LTX. In a further embodiment the composition comprises hexaglutamated LTX.

In one embodiment, the composition comprises an alpha polyglutamated PMX, MTX, RTX, or LTX. In a further embodiment the composition comprises pentaglutamated PMX, MTX, RTX, or LTX. In a further embodiment the composition comprises hexaglutamated PMX, MTX, RTX, or LTX.

In one embodiment, the composition comprises an L-alpha polyglutamated PMX. In a further embodiment the composition comprises an L-alpha pentaglutamated PMX. In a further embodiment the composition comprises an L-alpha hexaglutamated PMX.

In another embodiment, the composition comprises polyglutamated MTX. In a further embodiment the composition comprises an L-alpha pentaglutamated MTX. In a further embodiment the composition comprises an L-alpha hexaglutamated MTX.

In another embodiment, the composition comprises an L-alpha polyglutamated RTX. In a further embodiment the composition comprises an L-alpha pentaglutamated RTX. In a further embodiment the composition comprises an L-alpha hexaglutamated RTX.

In an additional embodiment, the composition comprises an L-alpha polyglutamated LTX. In a further embodiment the composition comprises an L-alpha pentaglutamated LTX. In a further embodiment the composition comprises an L-alpha hexaglutamated LTX.

In one embodiment, the composition comprises a D-alpha polyglutamated PMX, MTX, RTX, or LTX. In a further embodiment the composition comprises a D-alpha pentaglutamated PMX, MTX, RTX, or LTX. In a further embodiment the composition comprises a D-alpha hexaglutamated PMX, MTX, RTX, or LTX In one embodiment, the composition comprises a D-alpha polyglutamated PMX. In a further embodiment the composition comprises a D-alpha pentaglutamated PMX. In a further embodiment the composition comprises a D-alpha hexaglutamated PMX.

In another embodiment, the composition comprises a D-alpha polyglutamated MTX. In a further embodiment the composition comprises a D-alpha pentaglutamated MTX. In a further embodiment the composition comprises a D-alpha hexaglutamated MTX.

In another embodiment, the composition comprises a D-alpha polyglutamated RTX. In a further embodiment the composition comprises a D-alpha pentaglutamated RTX. In a further embodiment the composition comprises a D-alpha hexaglutamated RTX.

In an additional embodiment, the composition comprises a D-alpha polyglutamated LTX. In a further embodiment the composition comprises a D-alpha pentaglutamated LTX. In a further embodiment the composition comprises a D-alpha hexaglutamated LTX.

In one embodiment, the composition comprises a D-gamma polyglutamated PMX, MTX, RTX, or LTX. In a further embodiment the composition comprises a D-gamma pentaglutamated PMX, MTX, RTX, or LTX. In a further embodiment the composition comprises a D-gamma hexaglutamated PMX, MTX, RTX, or LTX.

In one embodiment, the composition comprises a D-gamma polyglutamated PMX. In a further embodiment the composition comprises a D-gamma pentaglutamated PMX. In a further embodiment the composition comprises a D-gamma hexaglutamated PMX.

In another embodiment, the composition comprises a D-gamma polyglutamated MTX. In a further embodiment the composition comprises a D-gamma pentaglutamated MTX. In a further embodiment the composition comprises a D-gamma hexaglutamated MTX.

In another embodiment, the composition comprises a D-gamma polyglutamated RTX. In a further embodiment the composition comprises a D-gamma pentaglutamated RTX. In a further embodiment the composition comprises a D-gamma hexaglutamated RTX.

In an additional embodiment, the composition comprises a D-gamma polyglutamated LTX. In a further embodiment the composition comprises a D-gamma pentaglutamated LTX. In a further embodiment the composition comprises a D-gamma hexaglutamated LTX.

In additional embodiments, the disclosure provides a liposomal alpha (L-alpha or D-alpha) or D-gamma polyglutamated antifolate (LPA) composition that comprises an alpha or D-gamma polyglutamated (e.g., pentaglutamated or hexaglutamated) antifolate. For example, the alpha (L-alpha or D-alpha) or D-gamma polyglutamed antifolate may be in a HEPES buffered solution within a liposome. In further embodiments the LPA composition is pegylated (PLPA). In some embodiments, the PLPA composition comprises an alpha (L-alpha or D-alpha) or D-gamma pentaglutamated antifolate. In some embodiments, the PLPA composition comprises an alpha (L-alpha or D-alpha) or D-gamma hexaglutamated antifolate. In some embodiments, the PLPA liposome is anionic or neutral. In other embodiments, the PLPA liposome is cationic. In some embodiments, the PLPA composition comprises at least 10% liposome, at least 20%, or at least 30% liposome entrapped alpha (L-alpha or D-alpha) or D-gamma polyglutamated antifolate. In some embodiments, the PLPA liposomes have a diameter in the range of 20 nm to 200 nm, 30 nm to 175 nm, or 50 nm to 150 nm. In some embodiments, the PLPA liposomes have a diameter in the range of 30 nm to 175 nm or 50 nm to 150 nm. In further embodiments, the PLPA liposomes have a diameter in the range of 80 nm to 120 nm.

In some embodiments, the PLPA composition comprises an alpha (L-alpha or D-alpha) or D-gamma polyglutamated antifolate selected from the group consisting of: polyglutamated MTX, polyglutamated PMX, polyglutamated LTX, polyglutamated AG2034, polyglutamated RTX, polyglutamated piritrexim, polyglutamated pralatrexate, polyglutamated AG2034, polyglutamated GW1843, polyglutamated aminopterin, and polyglutamated LY309887. In further embodiments, the alpha (L-alpha or D-alpha) or D-gamma polyglutamated antifolate is pentaglutamated. In one embodiment, the PLPA composition comprises alpha (L-alpha or D-alpha) or D-gamma polyglutamated PMX, MTX, RTX, or LTX. In further embodiments, the alpha (L-alpha or D-alpha) or D-gamma polyglutamated antifolate is hexaglutamated. In one embodiment, the PLPA composition comprises alpha (L-alpha or D-alpha) or D-gamma polyglutamated PMX, MTX, RTX, or LTX. In a further embodiment the PLPA composition comprises an alpha (L-alpha or D-alpha) or D-gamma pentaglutamated PMX, MTX, RTX, or LTX. In a further embodiment the PLPA composition comprises an alpha (L-alpha or D-alpha) or D-gamma hexaglutamated PMX, MTX, RTX, or LTX.

In one embodiment, the PLPA composition comprises an alpha polyglutamated PMX. In a further embodiment the PLPA composition comprises an alpha pentaglutamated PMX. In a further embodiment the PLPA composition comprises an alpha hexaglutamated PMX.

In another embodiment, the PLPA composition comprises an alpha polyglutamated MTX. In a further embodiment the PLPA comprises pentaglutamated MTX. In a further embodiment the PLPA comprises hexaglutamated MTX.

In another embodiment, the PLPA composition comprises an alpha polyglutamated RTX. In a further embodiment the PLPA composition comprises an alpha pentaglutamated RTX. In a further embodiment the PLPA composition comprises an alpha hexaglutamated RTX.

In an additional embodiment, the PLPA composition comprises an alpha polyglutamated LTX. In a further embodiment the PLPA composition comprises an alpha pentaglutamated LTX. In a further embodiment the PLPA composition comprises an alpha hexaglutamated LTX.

In one embodiment, the PLPA composition comprises an L-alpha polyglutamated PMX. In a further embodiment the PLPA composition comprises an L-alpha pentaglutamated PMX. In a further embodiment the PLPA composition comprises an L-alpha hexaglutamated PMX.

In another embodiment, the PLPA composition comprises an L-alpha polyglutamated MTX. In a further embodiment the PLPA comprises an L-alpha pentaglutamated MTX. In a further embodiment the PLPA comprises an L-alpha hexaglutamated MTX.

In another embodiment, the PLPA composition comprises an L-alpha polyglutamated RTX. In a further embodiment the PLPA composition comprises an L-alpha pentaglutamated RTX. In a further embodiment the PLPA composition comprises an L-alpha hexaglutamated RTX In an additional embodiment, the PLPA composition comprises an L-alpha polyglutamated LTX. In a further embodiment the PLPA composition comprises an L-alpha pentaglutamated LTX. In a further embodiment the PLPA composition comprises an L-alpha hexaglutamated LTX.

In one embodiment, the PLPA composition comprises a D-alpha polyglutamated PMX. In a further embodiment the PLPA composition comprises a D-alpha pentaglutamated PMX. In a further embodiment the PLPA composition comprises a D-alpha hexaglutamated PMX.

In another embodiment, the PLPA composition comprises a D-alpha polyglutamated MTX. In a further embodiment the PLPA comprises a D-alpha pentaglutamated MTX. In a further embodiment the PLPA comprises a D-alpha hexaglutamated MTX.

In another embodiment, the PLPA composition comprises a D-alpha polyglutamated RTX. In a further embodiment the PLPA composition comprise a D-alpha pentaglutamated RTX. In a further embodiment the PLPA composition comprise a D-alpha hexaglutamated RTX.

In an additional embodiment, the PLPA composition comprises a D-alpha polyglutamated LTX. In a further embodiment the PLPA composition comprises a D-alpha pentaglutamated LTX. In a further embodiment the PLPA composition comprises a D-alpha hexaglutamated LTX In one embodiment, the PLPA composition comprises a D-gamma polyglutamated PMX. In a further embodiment the PLPA composition comprises a D-gamma pentaglutamated PMX. In a further embodiment the PLPA composition comprises a D-gamma hexaglutamated PMX.

In another embodiment, the PLPA composition comprises a D-gamma polyglutamated MTX. In a further embodiment the PLPA comprises a D-gamma pentaglutamated MTX. In a further embodiment the PLPA comprises a D-gamma hextaglutamated MTX.

In another embodiment, the PLPA composition comprises a D-gamma polyglutamated RTX. In a further embodiment the PLPA composition comprises a D-gamma pentaglutamated RTX. In a further embodiment the PLPA composition comprises a D-gamma hexaglutamated RTX.

In an additional embodiment, the PLPA composition comprises a D-gamma polyglutamated LTX. In a further embodiment the PLPA composition comprises a D-gamma pentaglutamated LTX. In a further embodiment the PLPA composition comprises a D-gamma hexaglutamated LTX.

In some embodiments, the disclosure provides a liposomal alpha (L-alpha or D-alpha) or D-gamma polyglutamated antifolate composition wherein the liposome is pegylated and comprises a alpha (L-alpha or D-alpha) or D-gamma polyglutamated antifolate and targeting moiety attached to one or both of a PEG and the exterior of the liposome, and wherein the targeting moiety has a specific affinity for a surface antigen on a target cell of interest. In some embodiments, the targeting moiety is a polypeptide. In further embodiments, the targeting moiety is an antibody or a fragment of an antibody. In additional embodiments, the targeting moiety comprises one or more of an antibody, a humanized antibody, an antigen binding fragment of an antibody, a single chain antibody, a single-domain antibody, a bi-specific antibody, a synthetic antibody, a pegylated antibody, and a multimeric antibody. In additional embodiments, the targeting moiety has the specific affinity for an epitope on a tumor cell surface antigen that is present on a tumor cell but absent or inaccessible on a non-tumor cell. In some embodiments, the targeting moiety-PLPA further comprises one or more of an immunostimulatory agent, a detectable marker and a maleimide disposed on at least one of the PEG and the exterior of the liposome. In some embodiments, the targeting moiety-PLPA liposome is anionic or neutral. In other embodiments, the targeting moiety-PLPA liposome is cationic. In some embodiments, the targeting moiety-PLPA composition comprises at least 10% liposome entrapped alpha (L-alpha or D-alpha) or D-gamma polyglutamated antifolate. In additional embodiments, the targeting moiety-PLPA liposomes have a diameter in the range of 20 nm to 200 nm. In further embodiments, the liposomes have a diameter in the range of 80 nm to 120 nm.

In some embodiments, the targeting moiety-PLPA comprises a polypeptide targeting moiety such as an antibody or an antibody fragment and the targeting moiety binds a target antigen with an equilibrium dissociation constant (Kd) in a range of $0.5 \times 10^{-10}$ to $10 \times 10^{-6}$ as determined using BIA-CORE analysis. In further embodiments, the targeting moiety comprises a polypeptide that specifically binds a folate receptor. In some embodiments the folate receptor bound by the targeting moiety is one or more folate receptors selected from the group consisting of: folate receptor alpha (FR-$\alpha$), folate receptor beta (FR-$\beta$), and folate receptor delta (FR-$\delta$).

The disclosure also provides a method of killing a hyperproliferative cell that comprises contacting the hyperproliferative cell with a PLPA and/or LPA composition. In some embodiments the hyperproliferative cell is a cancer cell. In some embodiments, the method is performed in vivo. In some embodiments, the method is performed in vitro. In further embodiments, the cancer cell is a primary cell or a cell from a cell line obtained/derived from a cancer selected from the group consisting of: lung cancer, pancreatic, breast cancer, ovarian cancer, lung cancer, prostate cancer, head and neck cancer, gastric cancer, gastrointestinal cancer, colon cancer, esophageal cancer, cervical cancer, kidney cancer, biliary duct cancer, gallbladder cancer, and a hematologic malignancy.

In additional embodiments, the disclosure provides a method for treating cancer that comprises administering an effective amount of a liposomal alpha (L-alpha or D-alpha) or D-gamma polyglutamated (e.g., pentaglutamated and hexaglutamated) antifolate (LPA) composition and/or a pegylated-LPA (PLPA) composition, to a subject having or at risk of having cancer. In some embodiments, the method is administered to treat a cancer selected from the group consisting of: lung cancer, pancreatic, breast cancer, ovarian cancer, lung cancer, prostate cancer, head and neck cancer, gastric cancer, gastrointestinal cancer, colon cancer, esophageal cancer, cervical cancer, kidney cancer, biliary duct cancer, gallbladder cancer, and a hematologic malignancy. In some embodiments, the administered alpha (L-alpha or D-alpha) or D-gamma polyglutamated antifolate is a member selected from the group consisting of: polyglutamated methotrexate (MTX), polyglutamated pemetrexed (PMX), polyglutamated lometrexol (LTX), polyglutamated AG2034, polyglutamated raltitrexed (RTX), polyglutamated piritrexim, polyglutamated pralatrexate, polyglutamated AG2034, polyglutamated GW1843, polyglutamated aminopterin, and polyglutamated LY309887. In further embodiments, the administered composition comprises alpha (L-alpha or D-alpha) or D-gamma pentaglutamated antifolates. In further embodiments, the administered composition comprises alpha (L-alpha or D-alpha) or D-gamma hexaglutamated antifolates. In some embodiments, the administered composition comprises the alpha (L-alpha or D-alpha) or D-gamma polyglutamated form of PMX, MTX, RTX, or LTX. In further embodiments, the administered composition comprises the pentaglutamated form of PMX, MTX, RTX, or LTX. In further embodiments, the administered composition comprises the hexaglutamated form of PMX, MTX, RTX, or LTX. In one embodiment, the administered composition comprises the pentaglutamated form of PMX. In another embodiment, the administered composition comprises the pentaglutamated form of MTX. In another embodiment, the administered composition comprises the pentaglutamated form of RTX. In an additional embodiment, the administered composition comprises the pentaglutamated form of LTX. In one embodiment, the administered composition comprises the hexaglutamated form of PMX. In another embodiment, the administered composition comprises the hexaglutamated form of MTX. In another embodiment, the administered composition comprises the hexaglutamated form of RTX. In an additional embodiment, the administered composition comprises the hexaglutamated form of LTX.

In additional embodiments, the disclosure provides a method for treating cancer that comprises administering an effective amount and wherein the liposome is optionally pegylated), to a subject having or at risk of having cancer. In some embodiments, the method is administered to treat a cancer selected from the group consisting of: lung cancer, pancreatic, breast cancer, ovarian cancer, lung cancer, prostate cancer, head and neck cancer, gastric cancer, gastrointestinal cancer, colon cancer, esophageal cancer, cervical cancer, kidney cancer, biliary duct cancer, gallbladder cancer, and a hematologic malignancy. In some embodiments, the administered alpha (L-alpha or D-alpha) or D-gamma polyglutamated antifolate is a member selected from the group consisting of: polyglutamated methotrexate (MTX), polyglutamated pemetrexed (PMX), polyglutamated lometrexol (LTX), polyglutamated AG2034, polyglutamated raltitrexed (RTX), polyglutamated piritrexim, polyglutamated pralatrexate, polyglutamated AG2034, polyglutamated GW1843, polyglutamated aminopterin, and polyglutamated LY309887. In further embodiments, the administered composition comprises alpha (L-alpha or D-alpha) or D-gamma pentaglutamated antifolates. In further embodiments, the administered composition comprises alpha (L-alpha or D-alpha) or D-gamma hexaglutamated antifolates. In some embodiments, the administered composition comprises the alpha (L-alpha or D-alpha) or D-gamma polyglutamated form of PMX, MTX, RTX, or LTX. In some embodiments, the administered composition comprises the pentaglutamated form of PMX, MTX, RTX, or LTX. In some embodiments, the administered composition comprises the hexaglutamated form of PMX, MTX, RTX, or LTX. In a further embodiment, the administered composition comprises the alpha (L-alpha or D-alpha) or D-gamma pentaglutamated form of PMX. In a further embodiment, the administered composition comprises the alpha (L-alpha or D-alpha) or D-gamma hexaglutamated form of PMX. In another further embodiment, the administered composition comprises the alpha (L-alpha or D-alpha) or D-gamma pentaglutamated form of MTX. In another further embodiment, the administered composition comprises the alpha (L-alpha or D-alpha) or D-gamma hexaglutamated form of MTX. In another further embodiment, the administered composition comprises the pentaglutamated form of RTX. In another further embodiment, the administered composition comprises the hexaglutamated form of RTX. In an additional further embodiment, the administered composition comprises the pentaglutamated form of LTX. In an additional further embodiment, the administered composition comprises the hexaglutamated form of LTX.

In some embodiments, the disclosure provides a method of treating cancer that comprises administering an effective amount of a LPA composition and/or a pegylated-LPA (PLPA) composition to a subject having or at risk of having cancer, wherein the PLPA and/or LPA composition further contains a targeting moiety having a specific affinity for a surface antigen (epitope) on the cancer. In further embodiments, the disclosure provides a method for treating cancer that comprises administering a liposomal alpha (L-alpha or D-alpha) or D-gamma polyglutamated antifolate composition that comprises a polyglutamated antifolate and a targeting moiety that has a specific binding affinity for a folate receptor to a subject having or at risk of having cancer expresses on its surface the folate receptor bound by the targeting moiety. In further embodiments, the targeting moiety has a specific binding affinity for folate receptor alpha (FR-α), folate receptor beta (FR-β), and/or folate receptor delta (FR-δ).

In some embodiments, the method is administered to treat a cancer selected from the group consisting of: lung cancer, pancreatic, breast cancer, ovarian cancer, lung cancer, prostate cancer, head and neck cancer, gastric cancer, gastrointestinal cancer, colon cancer, esophageal cancer, cervical cancer, kidney cancer, biliary duct cancer, gallbladder cancer, and a hematologic malignancy. In some embodiments, the administered alpha (L-alpha or D-alpha) or D-gamma polyglutamated antifolate is a member selected from the group consisting of: polyglutamated methotrexate (MTX), polyglutamated pemetrexed (PMX), polyglutamated lometrexol (LTX), polyglutamated AG2034, polyglutamated raltitrexed (RTX), polyglutamated piritrexim, polyglutamated pralatrexate, polyglutamated AG2034, polyglutamated GW1843, polyglutamated aminopterin, and polyglutamated LY309887. In further embodiments, the administered composition comprises pentaglutamated antifolates. In further embodiments, the administered composition comprises hexaglutamated antifolates. In some embodiments, the administered composition comprises the alpha (L-alpha or D-alpha) or D-gamma polyglutamated form of PMX, MTX, RTX, or LTX. In some embodiments, the administered composition comprises the pentaglutamated form of PMX, MTX, RTX, or LTX. In some embodiments, the administered composition comprises the hexaglutamated form of PMX, MTX, RTX, or LTX. In a further embodiment, the administered composition comprises the pentaglutamated form of PMX. In a further embodiment, the administered composition comprises the hexaglutamated form of PMX. In another further embodiment, the administered composition comprises the pentaglutamated form of MTX. In another further embodiment, the administered composition comprises the hexaglutamated form of MTX. In another further embodiment, the administered composition comprises the pentaglutamated form of RTX. In another further embodiment, the administered composition comprises the hexaglutamated form of RTX In an additional further embodiment, the administered composition comprises the pentaglutamated form of LTX. In an additional further embodiment, the administered composition comprises the hexaglutamated form of LTX In additional embodiments, the disclosure provides a method for cancer maintenance therapy that comprises administering an effective amount of a LPA composition and/or a PLPA composition to a subject that is undergoing or has undergone cancer therapy.

In additional embodiments, the disclosure provides a method for treating a disorder of the immune system that comprises administering an effective amount a liposomal alpha (L-alpha or D-alpha) or D-gamma polyglutamated (e.g., pentaglutamated and hexaglutamated) antifolate composition that comprises a liposomal alpha (L-alpha or D-alpha) or D-gamma polyglutamated (e.g., pentaglutamated and hexaglutamated) antifolate containing a targeting moiety that has a specific affinity for a surface antigen on the immune cell of interest (and wherein the liposome is optionally pegylated), to a subject having or at risk of having an immune system disorder. In some embodiments, the method is administered to treat an autoimmune disease. In a further embodiment the method is administered to treat rheumatoid arthritis. In some embodiments, the administered polyglutamated antifolate is a member selected from the group consisting of: polyglutamated methotrexate (MTX), polyglutamated pemetrexed (PMX), polyglutamated lometrexol (LTX), polyglutamated AG2034, polyglutamated raltitrexed (RTX), polyglutamated piritrexim, polyglutamated pralatrexate, polyglutamated AG2034, polyglutamated GW1843, polyglutamated aminopterin, and polyglutamated LY309887. In further embodiments, the administered composition comprises pentaglutamated antifolates. In further embodiments, the administered composition comprises hexaglutamated antifolates. In some embodiments, the administered composition comprises the alpha (L-alpha or D-alpha) or D-gamma polyglutamated form of PMX, MTX, RTX, or LTX. In some embodiments, the administered composition comprises the pentaglutamated form of PMX, MTX, RTX, or LTX. In some embodiments, the administered composition comprises the hexaglutamated form of PMX, MTX, RTX, or LTX. In another further embodiment, the administered composition comprises the pentaglutamated form of MTX. In another further embodiment, the administered composition comprises the hexaglutamated form of MTX. In a further embodiment, the administered composition comprises the pentaglutamated form of PMX. In a further embodiment, the administered composition comprises the hexaglutamated form of PMX. In another further embodiment, the administered composition comprises the pentaglutamated form of RTX. In another further embodiment, the administered composition comprises the hexaglutamated form of RTX. In an additional further embodiment, the administered composition comprises the pentaglutamated form of LTX. In an additional further embodiment, the administered composition comprises the hexaglutamated form of LTX.

The disclosure also provides a method of delivering alpha (L-alpha or D-alpha) or D-gamma polyglutamated antifolate to a tumor that comprises: administering tumor to a subject having the tumor, a liposomal alpha (L-alpha or D-alpha) or D-gamma polyglutamated (e.g., pentaglutamated and hexaglutamated) antifolate (LPA) composition and/or a pegylated-LPA (PLPA) comprising a targeting moiety that has a specific binding affinity for a surface antigen on the tumor, and wherein the targeted-PLPA and/or targeted-LPA composition is delivered to the tumor in a therapeutically effective dose.

In additional embodiments the disclosure provides a method of preparing a composition that comprises a liposomal alpha (L-alpha or D-alpha) or D-gamma polyglutamated antifolate composition, the method comprising: forming a mixture comprising: liposomal components; polyglutamated antifolate in solution; homogenizing the mixture to form liposomes in the solution; and processing the mixture to form liposomes containing polyglutamated antifolate.

Pharmaceutical compositions comprising a liposomal alpha (L-alpha or D-alpha) or D-gamma polyglutamated (e.g., pentaglutamated and hexaglutamated) antifolate (LPA) composition and/or a pegylated-LPA (PLPA) composition and optionally further comprising a targeting moiety that has a specific affinity for a surface antigen on the surface of a target cell of interest are also provided.

BRIEF DESCRIPTION OF THE DRAWINGS/FIGURES

FIG. 1 depicts homeostasis of folates and cellular accumulation of antifolates. Influx and efflux (anti)folates transporters. Once inside the cell, (anti)folates undergo polyglutamation in the cytosol and mitochondria, whereas the counteracting process of hydrolysis occurs in the lysosome. FIG. 1 is adapted from Gonen et al., Drug Resistance Updates 15:183-210 (2012).

FIG. 2 depicts cellular folate metabolism and its compartmentalization in the cytosol and mitochondria. FIG. 2 is adapted from Gonen et al., Drug Resistance Updates 15:183-210 (2012).

FIGS. 3A and 3B depict the disruption of cell polarity and tissue disorganization that is a hallmark of advanced epithelial tumors. As depicted in FIG. 3A, normal simple epithelium comprises a monolayer of individual cells that display a distinct apical-basal polarity. Cells are tightly packed and connected to each other by the apical junctional complexes, which separate apical and basolateral membrane domains. In normal tissue where polarity is preserved, FR-α is attached at the apical surface of cells situated away from, and out of direct contact with folates in the blood circulation. As depicted in FIG. 3B, cells in high-grade epithelial tumors display loss of apical-basal polarity and overall tissue disorganization, putting FR-α in direct contact with folates in blood circulation. This feature of tumor tissue cells has significance for antimetabolites based therapies while minimizing associated severe and sometime life-threatening toxicities. If one designs a chemical entity to deliver, for example, an alpha (L-alpha or D-alpha) or D-gamma polyglutamate form of antifolates in a manner that selectively targets specifically folate receptor alpha while avoiding RFCs, one could possibly increase exposure of polyglutamated forms of antifolates to tumor tissue cells only, because these tumor tissue cells overexpress folate receptor alpha while this receptor is concurrently in direct contact with blood circulation, which is not the case for normal tissues in which folate receptor alpha is expressed in a restricted manner and away from contact with circulating blood (FIGS. 3A and 3B).

FIG. 4 is adapted from Gonen et al., Drug Resistance Updates 15:183-210 (2012).

FIG. 6 shows chemical formulae of exemplary L-gamma pentaglutamate and hexaglutamate antifolate compositions encompassed by the disclosure.

Figure 7:
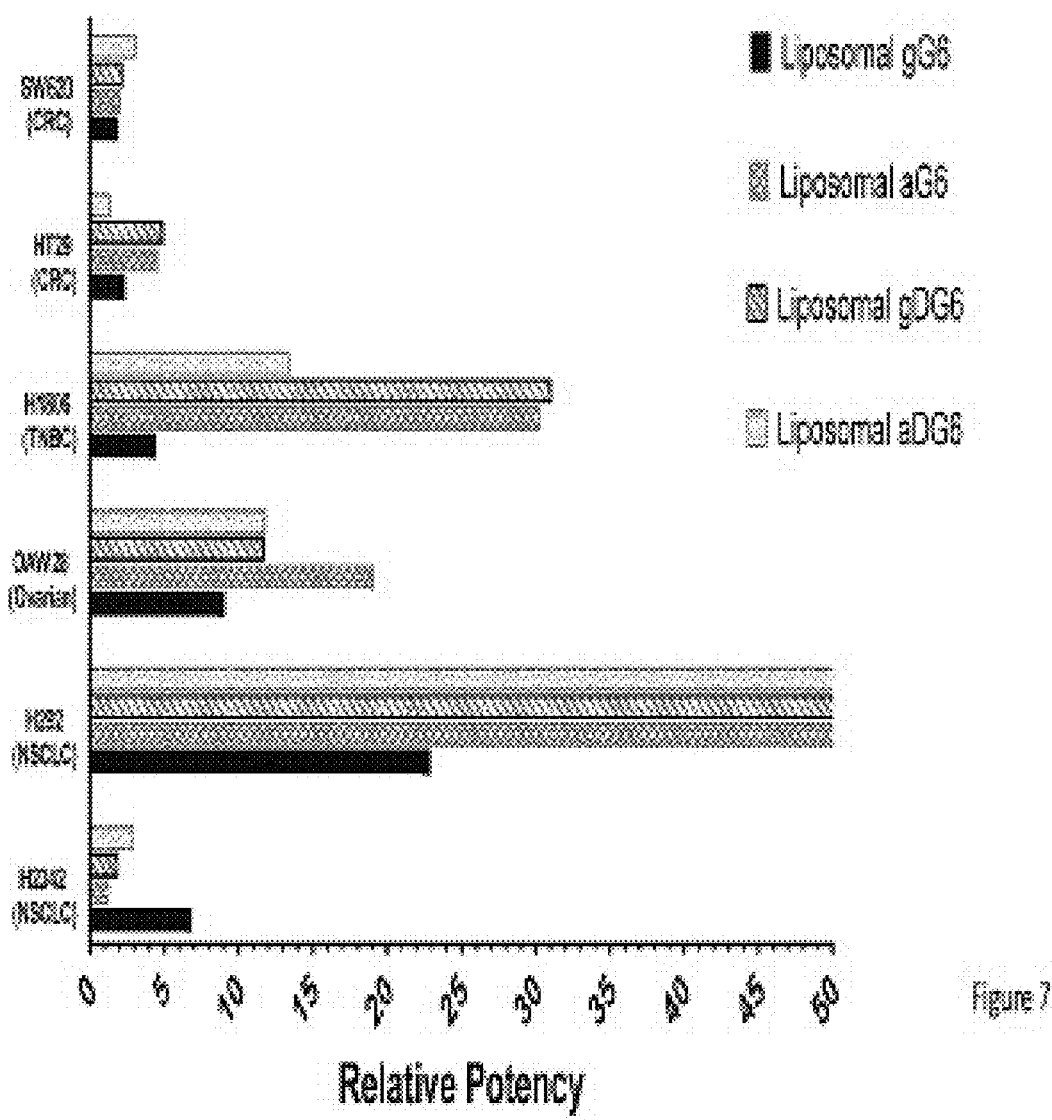

FIG. 7 presents the relative potency of liposomal pemetrexed L-Gamma hexaglutamate (liposomal gG6) and its mirror image (enantiomer) liposomal pemetrexed gamma-D hexaglutamate (liposomal gDG6), and liposomal pemetrexed alpha-L hexaglutamate (liposomal aG6) and its mirror image, liposomal alpha-D hexaglutamate (liposomal aDG6) relative to pemetrexed following exposure of the cancer cell lines SW620 (CRC), HT-29 (colon cancer), H1806 (triple negative breast cancer), OAW28 (ovarian cancer), H292 (NSCLC, adenocarcinoma subtype), and H2342 (NSCLC, adenocarcinoma subtype), over 48 hours.

Figure 8:
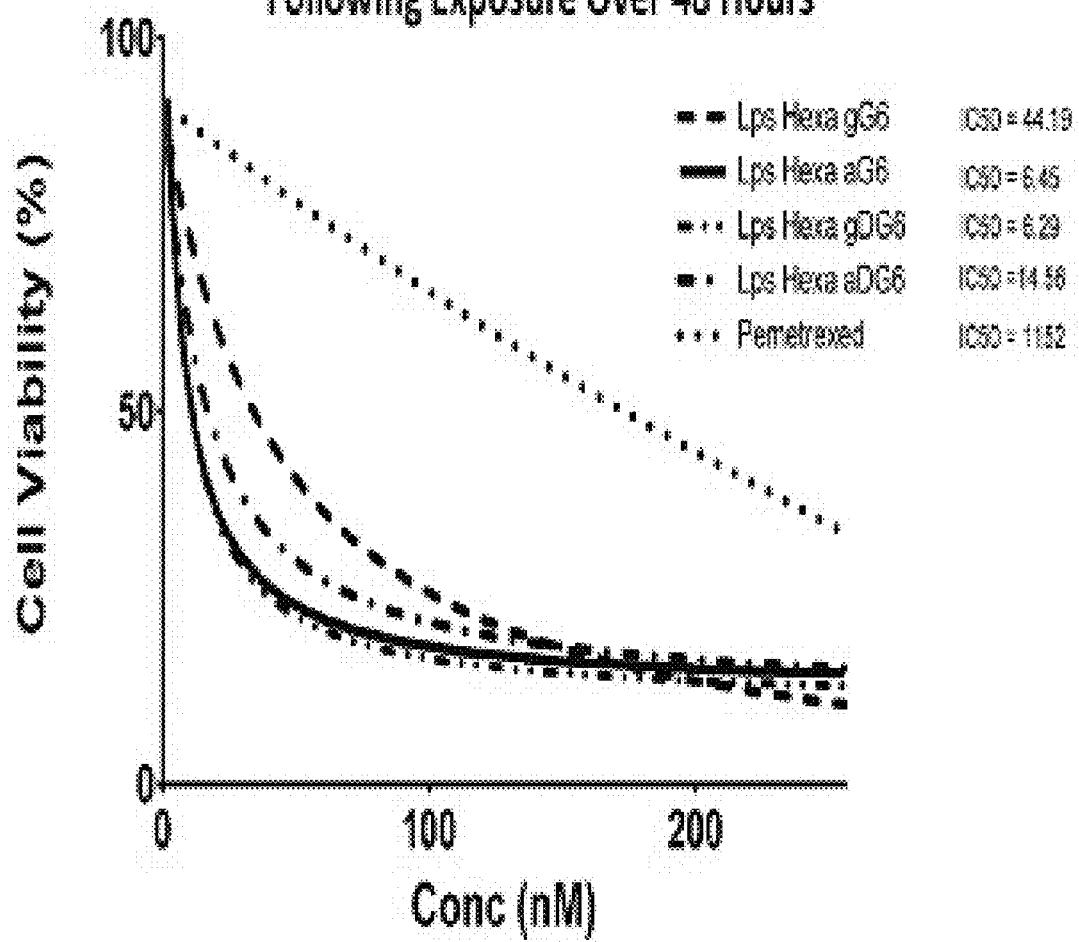

FIG. 8 presents the treatment effect on HCC1806 triple negative breast cancer cells following exposure of liposomal pemetrexed L-Gamma hexaglutamate (Lps Hexa gG6), liposomal pemetrexed alpha-L hexaglutamate (Lps Hexa aG6), liposomal pemetrexed gamma-D hexaglutamate (Lps Hexa gDG6), liposomal pemetrexed alpha-D hexaglutamate (Lps Hexa aDG6), and to pemetrexed over 48 hours.

Figure 9:
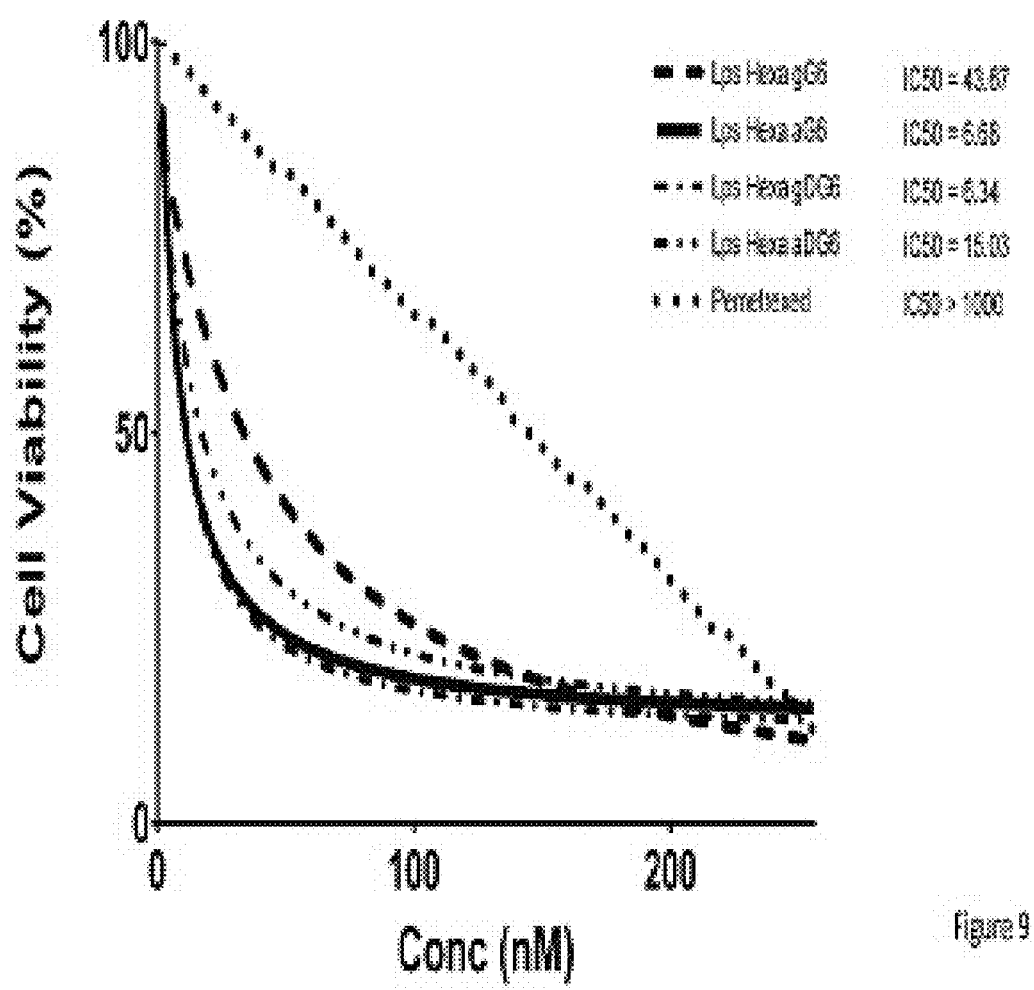

FIG. 9 presents the treatment effect on H292 non-small cell lung cancer cells following exposure of liposomal pemetrexed L-Gamma hexaglutamate (Lps Hexa gG6), pemetrexed L-Gamma hexaglutamate (Lps Hexa gG6), liposomal pemetrexed alpha-L hexaglutamate (Lps Hexa aG6), liposomal pemetrexed gamma-D hexaglutamate (Lps Hexa gDG6), liposomal pemetrexed alpha-D hexaglutamate (Lps Hexa aDG6), and to pemetrexed over 48 hours.

Figure 10:
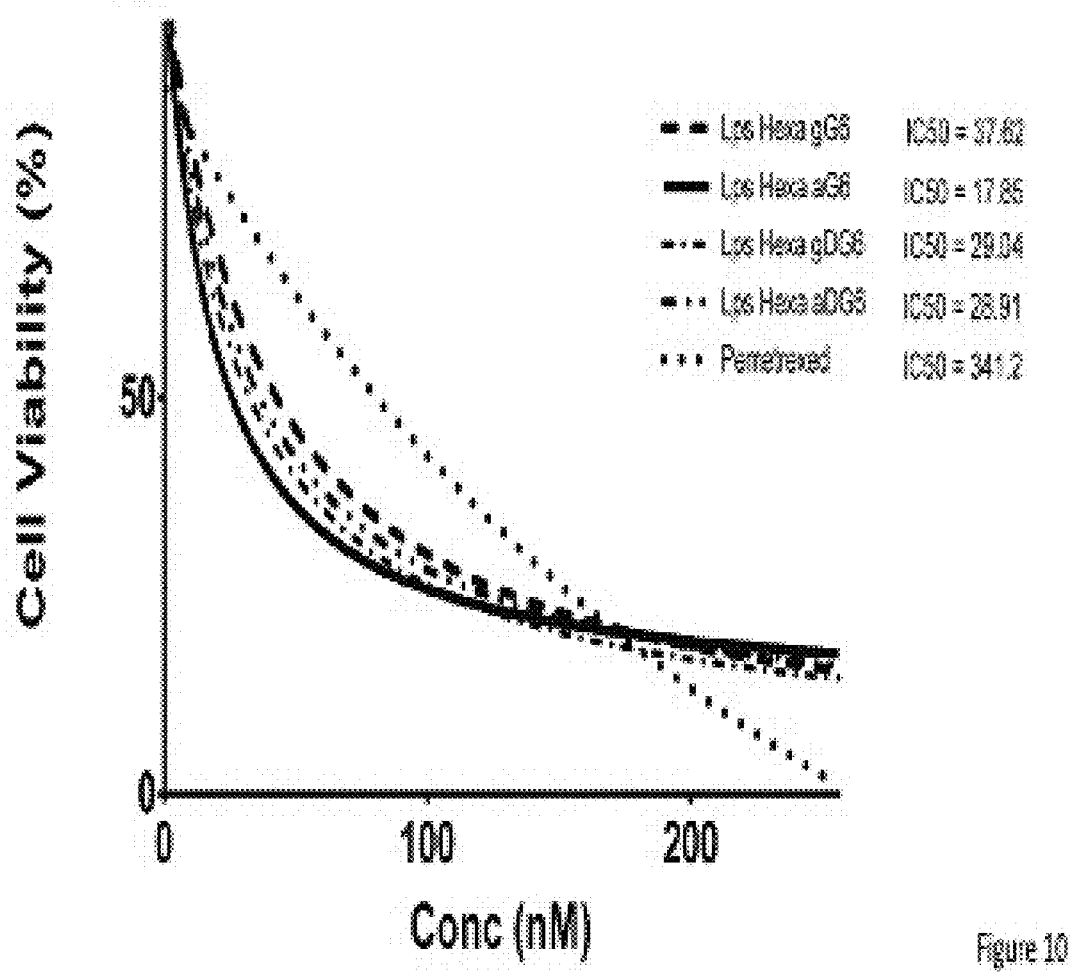

FIG. 10 presents the treatment effect on OAW28 ovarian cancer cells following exposure of liposomal pemetrexed L-Gamma hexaglutamate (Lps Hexa gG6) hexaglutamated pemetrexed isomer liposomes liposomal pemetrexed L-Gamma hexaglutamate (Lps Hexa gG6), liposomal pemetrexed alpha-L hexaglutamate (Lps Hexa aG6), liposomal pemetrexed gamma-D hexaglutamate (Lps Hexa gDG6), liposomal pemetrexed alpha-D hexaglutamate (Lps Hexa aDG6), as compared to pemetrexed over 48 hours.

Figure 11:
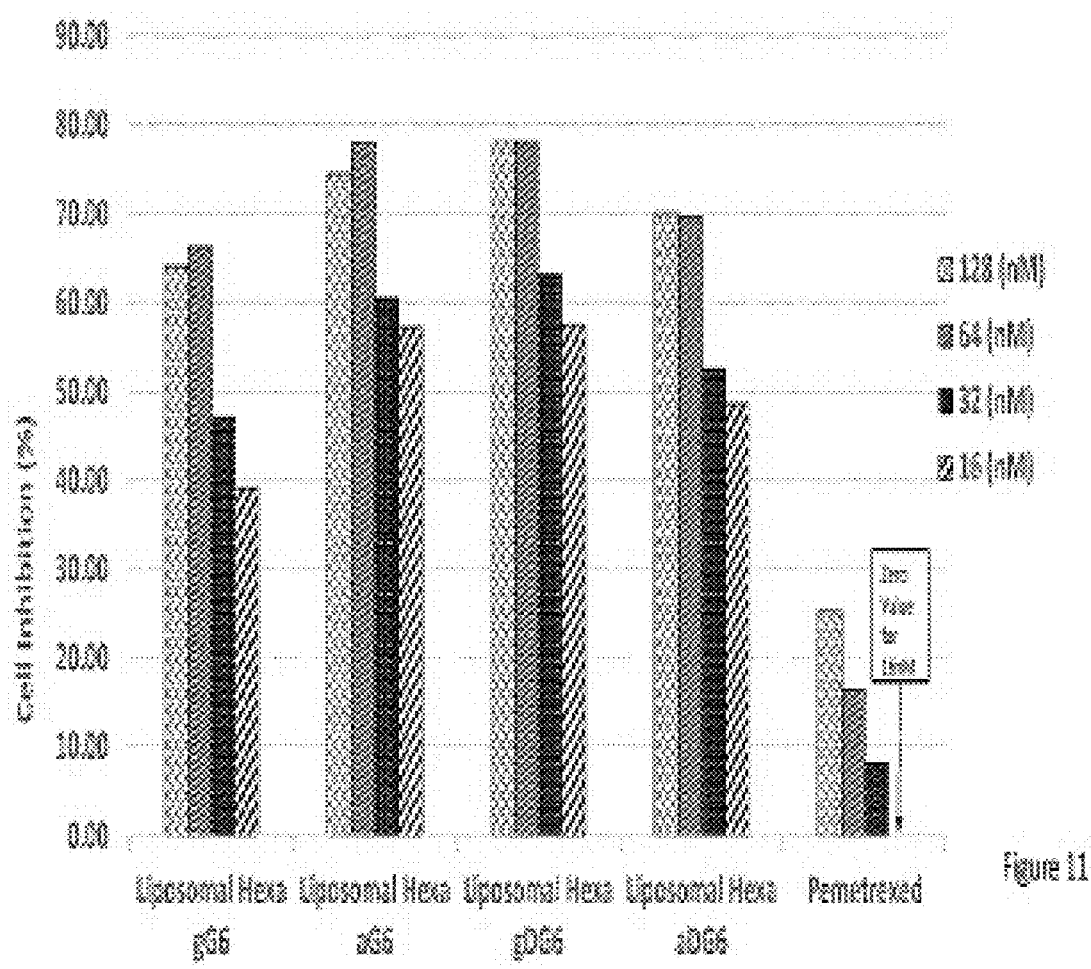

FIG. 11 presents the treatment effect on H292 non-small cell lung cancer cells following exposure of various dose levels ranging from 16 to 128 nM of liposomal pemetrexed L-Gamma hexaglutamate (Liposomal gG6), liposomal pemetrexed alpha-L hexaglutamate (Liposomal aG6), liposomal pemetrexed gamma-D hexaglutamate (Liposomal gDG6), liposomal pemetrexed alpha-D hexaglutamate (Liposomal aDG6), and pemetrexed over 48 hours. At each of the tested dose ranges, the liposomal pemetrexed gG6 formulation is superior to inhibiting H292 non-small cell lung cancer cells compared to pemetrexed.

Figure 12:
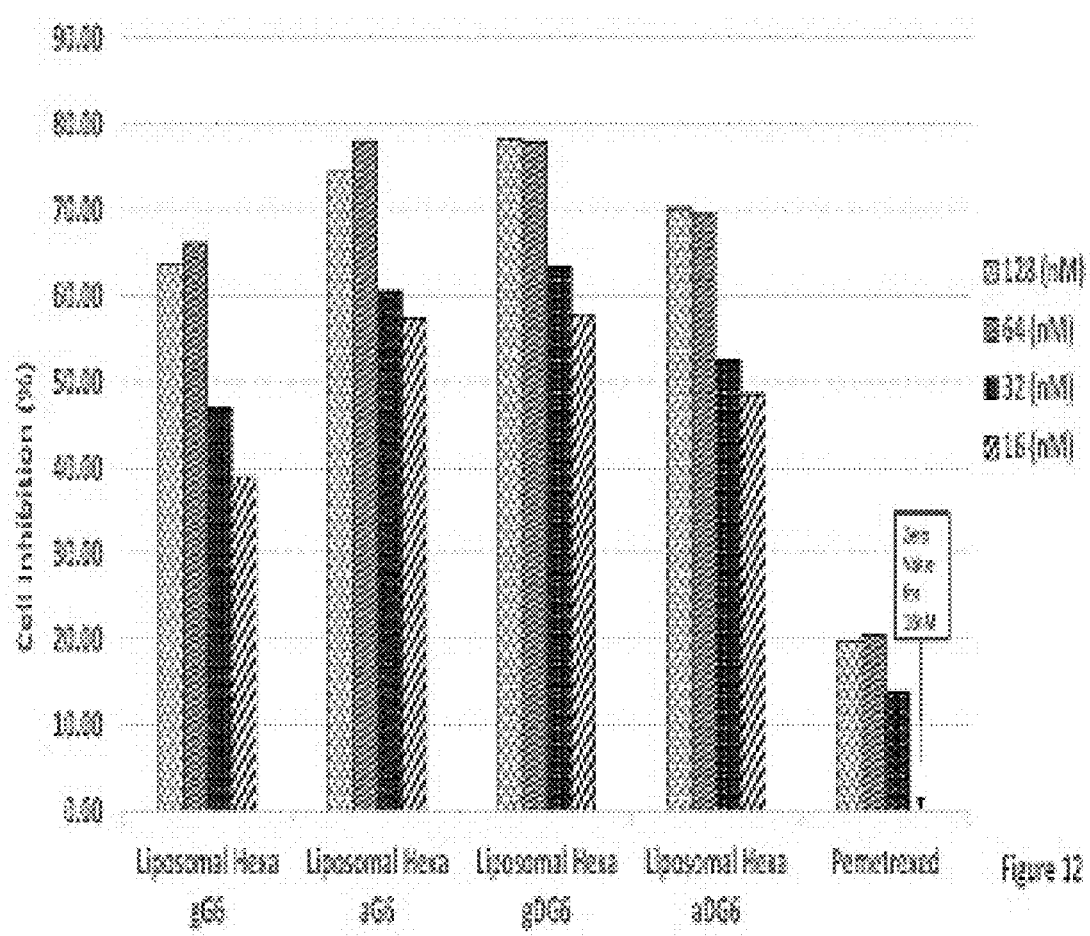

FIG. 12 presents the treatment effect on HCC1806 triple negative breast cancer cells following exposure of 16 nM, 32 nM, 64 nM, and 128 nM of liposomal pemetrexed L-Gamma hexaglutamate (Liposomal gG6), liposomal pemetrexed alpha-L hexaglutamate (Liposomal aG6), liposomal pemetrexed gamma-D hexaglutamate (Liposomal gDG6), liposomal pemetrexed alpha-D hexaglutamate (Liposomal aDG6), and pemetrexed over 48 hours. At each of the tested doses, the liposomal pemetrexed gG6 formulation is superior to pemetrexed in inhibiting HCC1806 triple negative breast cancer cells.

Figure 13:
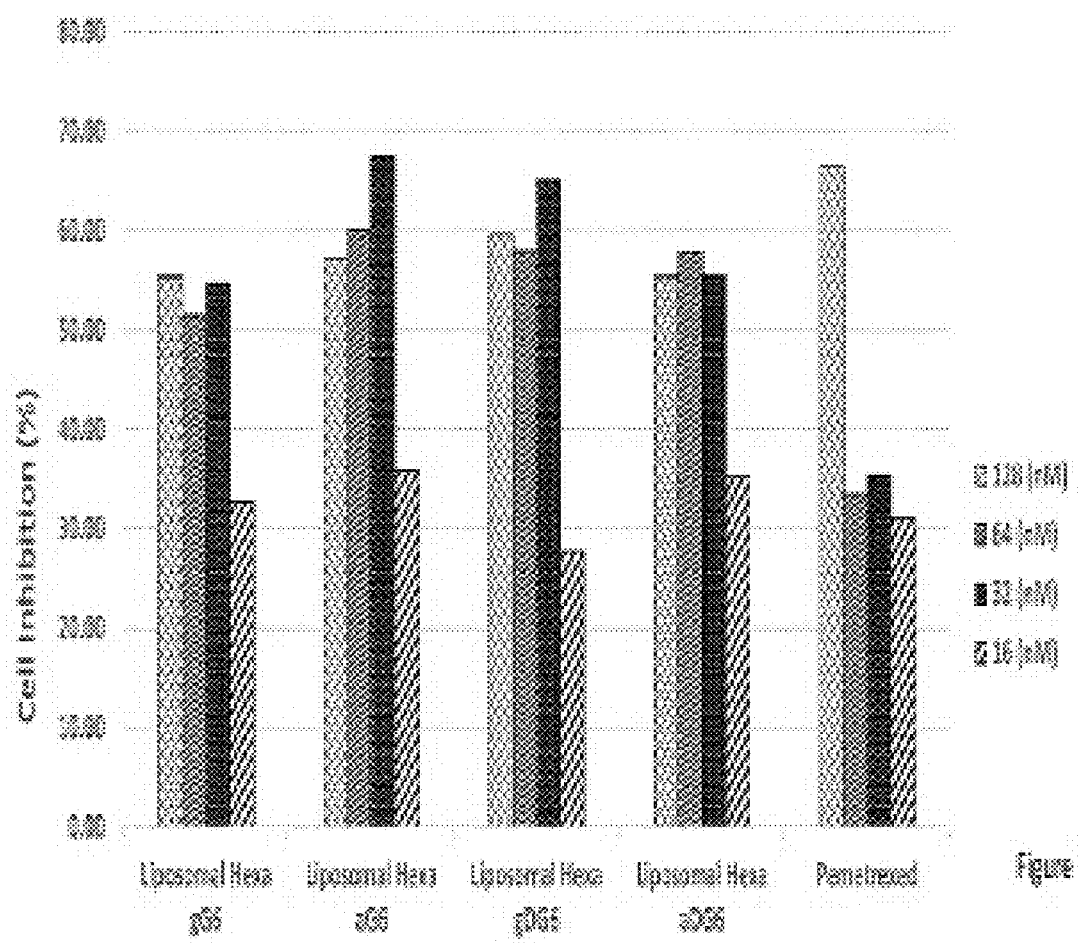

FIG. 13 presents the treatment effect on OAW28 ovarian cancer cells of liposomal pemetrexed L-Gamma hexaglutamate (Liposomal gG6), liposomal alpha-L hexaglutamate (Liposomal aG6), liposomal gamma-D hexaglutamate (Liposomal gDG6), liposomal alpha-D hexaglutamate (Liposomal aDG6), and pemetrexed following exposure over 48 hours following exposure over a range of concentrations. At the dose of 128 nM, pemetrexed appears to more effective than the Liposomal pemetrexed gG6 liposomal formulation, whereas the liposomal formulation at the dose of 32 nM and 64 nM has a better treatment effect than pemetrexed; at 16 nM the Liposomal pemetrexed gG6 treatment effect is similar in to pemetrexed.

Figure 14:
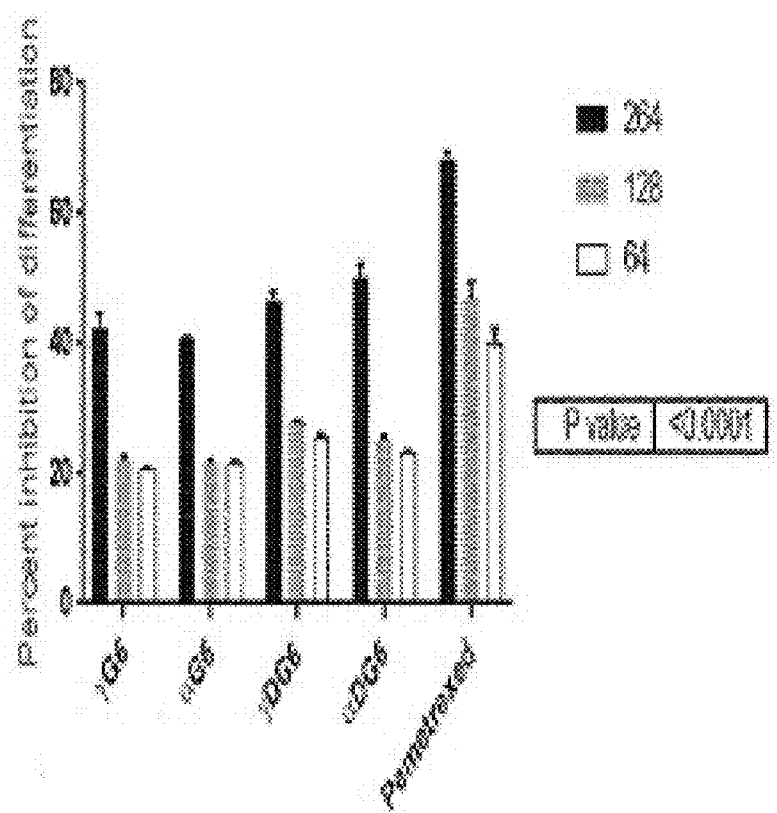

FIG. 14 shows the toxicity of liposomal pemetrexed L-Gamma hexaglutamate (Liposomal gG6), liposomal pemetrexed alpha-L hexaglutamate (Liposomal aG6), liposomal pemetrexed gamma-D hexaglutamate (Liposomal gG6), liposomal pemetrexed alpha-D hexaglutamate (Liposomal aDG6), and pemetrexed on differentiating human neutrophils at 16 nM, 32 nM, 64 nM, 128 nM, and 264 nM. The figure demonstrates that liposomal pemetrexed gG6 is significantly less toxic to differentiating human neutrophils then pemetrexed.

Figure 15:
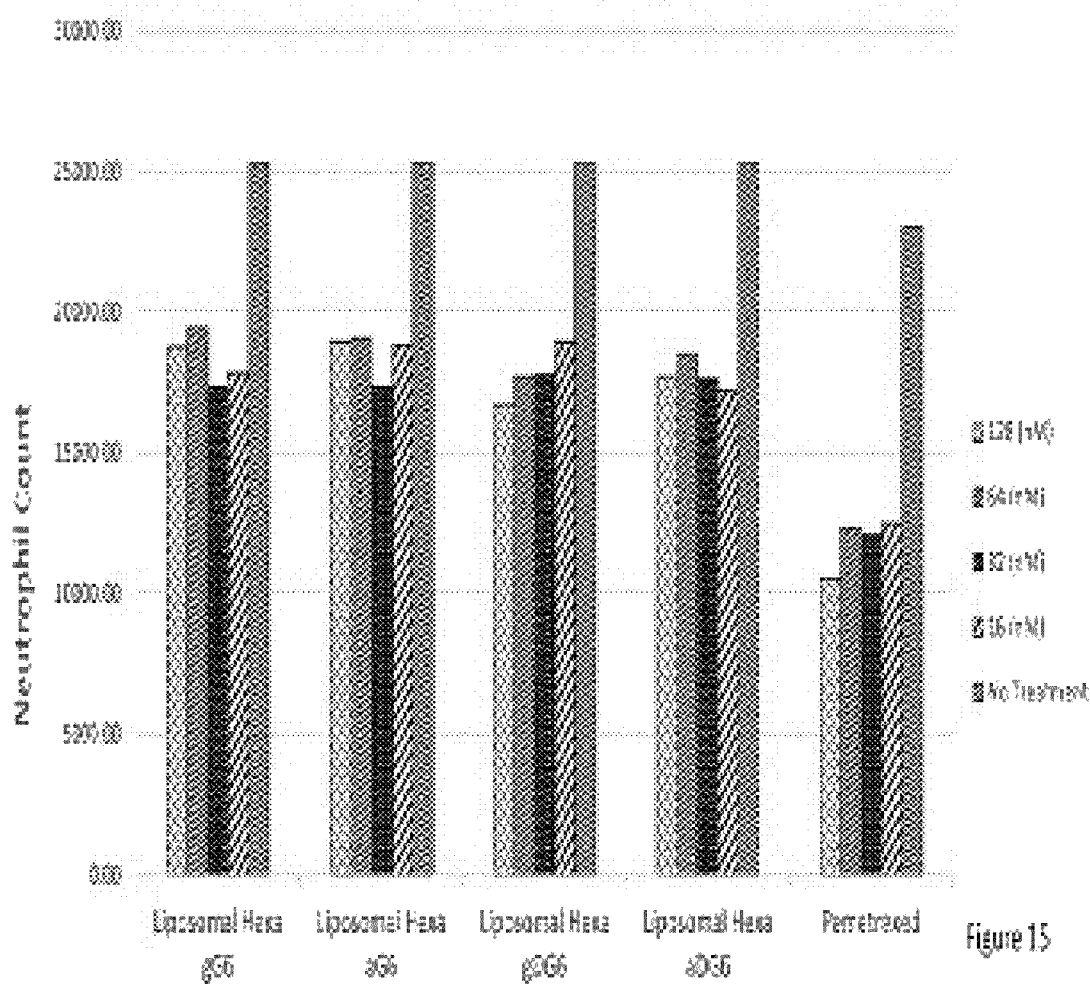

FIG. 15 shows the effect of liposomal pemetrexed L-Ganuna hexaglutamate (liposomal gG6), liposomal pemetrexed alpha-L hexaglutamate (liposomal aG6), liposomal gamma-D hexaglutamate (liposomal gDG6), liposomal alpha-D hexaglutamate (liposomal aDG6), and pemetrexed on pentagulutmated and pemetrexed on neutrophils (differentiated from CD34+ cells) following exposure of various dose levels ranging from 16 to 128 nM of the corresponding agent over 48 hours.

Figure 16:
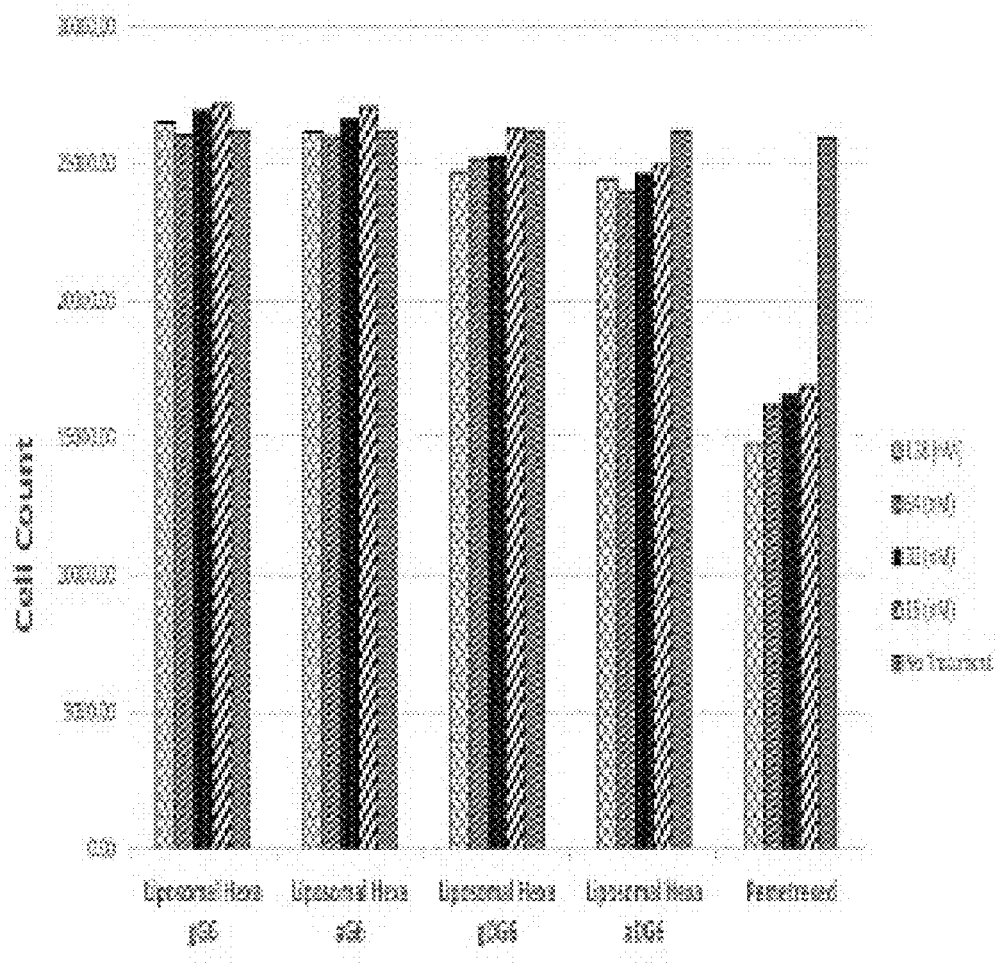

FIG. 16 shows the effect of liposomal pemetrexed L-Gamma hexaglutamate (liposomal gG6), liposomal pemetrexed alpha-L hexaglutamate (liposomal aG6), liposomal pemetrexed gamma-D hexaglutamate (liposomal gDG6), liposomal pemetrexed alpha-D hexaglutamate (liposomal aDG6), and pemetrexed on AML12 liver cells following exposure over 48 hours at 16 nM, 32 nM, and 64 nM, and 128 nM of the corresponding agent. Strikingly, there does not appear to be any toxicity to the AML12 liver cells following treatment with a liposomal pemetrexed gG6 at any of the liposomal agents at the dose levels tested. In contrast, pemetrexed treatment results in a reduction in the AML12 liver cell counts of approximately 40% at all doses studied.

FIG. 17 shows the effect of liposomal pemetrexed L-Gamma hexaglutamate (liposomal gG6), liposomal pemetrexed alpha-L hexaglutamate (liposomal aG6), liposomal pemetrexed gamma-D hexaglutamate (liposomal gDG6), liposomal pemetrexed alpha-D hexaglutamate (liposomal aDG6), and pemetrexed on CCD841 colon epithelium cells following exposure over 48 hours at 16 nM, 32 nM, and 64 nM, and 128 nM, of the corresponding agent. At all of the concentrations tested, pemetrexed leads to approximately a ≥50% decrease in the number of CCD841 colon epithelium cells compared to approximately a 20% or less decrease in cell number after treatment with each of the liposomal agents tested.

DETAILED DESCRIPTION

The present application describes advances over prior cancer treatments and methods of delivering antifolates to cancer cells. The disclosure relates to a class of antifolates that were previously unable to be exploited due to issues relating to cellular uptake and unknown toxicity.

More specifically, the present application describes encapsulated polyglutamated antifolates such as, but not limited to, pemetrexed polyglutamate and Lometrexol polyglutamate. In a non-limiting example, the encapsulated pemetrexed polyglutamate is targeted using a targeting moiety with a specific affinity for one or more folate receptors alpha, beta and delta. The encapsulated pemetrexed polyglutamate may also be untargeted.

Folate is a water-soluble B vitamin. The primary role of folate in the body/cell is as a cofactor to various methyltransferases involved in serine, methionine, thymidine and purine biosynthesis that are critical processes involved in cell division. The major function of folate is to mediate the transfer of one-carbon unit involved in nucleotide biosynthesis, the remethylation of homocysteine (Hcy), and biological methylation reactions. As an essential co-factor of the de novo biosynthesis of nucleotide, folate plays an important role in DNA synthesis, stability and integrity, and repair. Folate also provides the primary methyl group donor for the methylation of DNA (regulates gene expression), proteins (important post-translational modifications), and lipids (important in their synthesis, for example phosphatidylcholine). As explained in greater detail below, because of this, antifolates were developed as a treatment for cancer with intent to block the actions of folate, thereby inhibiting cell division, DNA/RNA synthesis and repair as well as protein synthesis.

In nature, folate occurs in animal products and in leafy vegetables in polyglutamated forms. Polyglutamates are not amenable to physiological transport. Natural polyglutamates are broken down in the jejunum primarily into monoglutamates before they are physiologically transported and taken up by the cell. Dietary folate in the form of the polyglutamates is then cleaved to the monoglutamate in the jejunum where it is absorbed. Once absorbed by enterocytes, folate is either polyglutamated and retained within the cells or released into portal circulation for various compartments for metabolism, storage, or enterohepatic recirculation. Folates enter plasma and are rapidly cleared by entering hepatocytes and other cells.

The liver takes up the majority of folate that enters portal circulation, while the remaining folate passes through the liver, enters the general circulation and is taken up by other tissues where it is converted into its polyglutamate form for intracellular storage. The liver is the primary reservoir of folates. Surgical biliary drainage can result in a reduction in serum folate within six hours, whereas dietary restriction does not produce a comparable fall for three weeks, presumably because total body stores of folate are estimated to be between 500 to 20,000 mcg. This observation indicates that there is a large enterohepatic circulation of folate.

Monoglutamates are the only circulating forms of folates in the blood and the only form of folate that is transported across the cell membrane. Once absorbed by enterocytes, folate is either polyglutamated and retained within the cells or released into portal circulation for various compartments for metabolism, storage, or enterohepatic recirculation. Once monoglutamates are taken up into cells, intracellular folates exist primarily as polyglutamates, a form that is biologically active as a cofactor to various methyltransferases involved in serine, methionine, thymidine and purine biosynthesis that are critical processes involved in cell division.

Polyglutamation involves the addition of glutamate group(s) in gamma linkage to the end carboxyl group of the neighboring folyl glutamate by the enzyme folylpolyglutamate synthetase (FPGS) using ATP as its energy source. The alpha and gamma forms of a polyglutamated drug, such as pemetrexed pentaglutamate, have the same elemental composition and molecular mass but different structures. The glutamic acid residues are linked via amide bonds, but the spacing between these amide bonds differs. In the alpha-linked configuration, there is only 1 aliphatic carbon between each amide bond, resulting in a more compact molecule and closer spacing of the negatively charged carboxylate groups on the side-chains. In the L-Gamma linked configuration, there are 3 aliphatic carbons between each amide bond, resulting in a more extended molecule with larger distances between negative charges. Drug-protein interactions that depend on the gross structural features of the drug, such as overall net charge, are not likely to be affected by these differences. However, drug-protein interactions that are dependent on the detailed chemical environment around the amide bonds (such as the folylpolyglutamate hydrolase) may be impacted by the different configurations.

Polyglutamation refers to the addition of glutamic acid residue(s) to a molecule (such as an antifolate) so that the resultant molecule after the polyglutamation has more than one glutamic acid residue. The literature has used multiple names to refer to the glutamic acid residue such as glutamate, glutamyl group, glutamyl radical, and the like. Each of the glutamic acid residues (glutamyl groups) may independently be in the L-form or the D-form.

For example, pemetrexed, whose chemical name is "N-[4-2-(2-Amino-4,7-dihydro-4-oxo-1H-pyrrolo[2,3-d]pyrimidin-5-yl)ethyl]benzoyl]-1-glutamic acid" already has one glutamyl group (monoglutamated). The addition of glutamic acid residue(s) to pemetrexed as described herein results in polyglutamated pemetrexed. For example, the addition of 5 more glutamic acid residue to pemetrexed would lead to a total of 6 glutamyl groups (one from pemetrexed and 5 additional glutamyl groups added) and is referred to in this document as hexaglutamated pemetrexed or pemetrexed hexaglutamate. In the literature this may also be referred to as pentaglutamated pemetrexed or pemetrexed pentaglutamate.

Gamma polyglutamation refers to the addition of glutamic acid residue(s) to a molecule as described above, where the peptide bonds are between the amino group of glutamic acid and the carboxyl group at gamma carbon of the glutamic acid side chain. Alpha polyglutamation refers to the addition of glutamic acid residue(s) to a molecule, as described above, where the peptide bonds are between the amino group of glutamic acid and the carboxyl group at alpha carbon of the glutamic acid side chain.

A single molecule may be formed by gamma polyglutamation only, alpha polyglutamation only, or a combination of gamma polyglutamation and alpha polyglutamation.

Antifolates were developed more than 70 years ago as "folic acid mimic molecule" cytotoxic agents. The rationale was to design a class of molecules that would counter the action of folic acid in fast replicating cells such as cancer cells, taking advantage of physiological folate transport mechanism and their facilitative intracellular mode of action for DNA replication during the cell division. Specifically, antifolates were designed to mimic folic acid in its systemic transport, physiologic cell uptake (e.g., via reduced folate carriers (RFCs) and proton-coupled folate transporters (PCFTs)) and intracellular processing. Antifolates act specifically during DNA and RNA synthesis, exerting a cytotoxic effect during the S-phase of the cell cycle. As a result, they have a greater toxic effect on rapidly dividing cells such as malignant and myeloid cells.

Generally speaking, there are four transporters of folates and antifolates in the human body: reduced folate carriers (RFCs), folate receptors (FRs), proton-coupled folate transporters (PCFTs) and ATP-binding-cassette transporters. As noted above, none of these transport mechanisms are effective for transporting free polyglutamates across cell membranes.

RFCs are saturable anion dependent cell membrane carriers with a greater affinity for reduced folates and hydrophilic antifolates such as MTX or PMX and affinity for PMX that is 2-fold higher than that for MTX. They are members of the superfamily of solute carriers, and utilize the high transmembrane anion gradient, particularly the organic phosphate gradient which is modulated by energy status of the cell in order to achieve uphill folate transport into the cell.

The transport of cytotoxic antifolates by RFCs is not tumor specific. Because RFCs are ubiquitously expressed in normal tissues and exhibit a high level of activity at neutral pHs that are characteristic of most normal tissues, antifolates transported via RFCs have been shown to cause toxicities to a select type of normal tissues.

Folate receptors alpha, beta and delta (FR-α, FR-β and FR-δ) are high-affinity folate-binding proteins that are anchored in the cell membrane by the glycosylphosphatidylinositol (GPI) anchor domain. FRs have an especially high affinity for FA. They transport folates into cells via an endocytosis mechanism. Once in the cytoplasm, when the vesicle acidifies to a pH of 6.0-6.5, folate is released from the receptor and is exported from the endosome by a mechanism that has been proposed to be mediated in part by PCFT. Even though FR-α has a higher affinity for its preferred substrates than RFC, its folate transport into the cell requires a series of steps such as binding, invagination, vesicle formation and translocation, acidification, and export of substrate from the vesicle into cytoplasm. Because of these multiple steps required for transport into the cell, the rate of FR-mediated folate transport is 1% of the rate mediated by RFC.

The proton-coupled folate transporter (PCFT) is a folate-H+symporter that functions most efficiently in an acidic extracellular environment that is, among others, characteristic of hypoxic environment. The important difference between RFC and PCFT is the optimum pH that impacts their affinities for transport substrates. At pH 7.4, the transport of antifolates is mediated predominantly by RFC as RFC activity is optimal and the activity of PCFT is minimized. Alternatively, PCFT activity is more prominent as pH is decreased. Besides mediating intestinal folate absorption and uptake into tissues in which there is an acidic extracellular environment such as solid tumors or, less efficiently, transport into tissues in a neutral pH environment, PCFT may play a role, in folate receptor-mediated endocytosis.

Several of the ATP-Binding-Cassette Transporters are low-affinity, high capacity ATP-dependent efflux pumps of folates and antifolates. These include the multidrug-resistance-associated proteins, MRP1-MRP5 and the breast-cancer resistance protein, BCRP. All of these drug resistance efflux pumps are not just involved in pumping antifolates out of the cells, but have also been shown to pump out of cells other classes of drugs.

Intracellular folate is converted to polyglutamates by FPGS, whereas GGH removes the terminal glutamates, thereby facilitating the export of folate out of the cell back to extra-cellular circulation by the ATP-Binding-Cassette Transporters, sometime also referred to as folate efflux pumps. Without wishing to be bound by theory, polyglutamated folates are thought to be better retained in cells because they are poor substrates of the ATP-binding cassette transporters. In addition, without wishing to be bound by theory, polyglutamated folates are believed to be better substrates for intracellular folate dependent enzymes compared to monoglutamates.

As is the case for folates, antifolates such as MTX, PMX are RTX are believed to be retained in the tumor and normal cells by FPGS-induced polyglutamation and are exported from cells, after hydrolysis to monoglutamates, by GGH. As with the physiologic folate, polyglutamated antifolates are retained in cells longer, thereby increasing their cytotoxicity by extending the length of exposure. Polyglutamated antifolates generally have a higher affinity for and as a result inhibit their target folate-dependent enzymes in thymidylate and purine biosynthesis to a greater extent than monoglutamate forms. It is because of this that FPGS and GGH are considered to be important enzymes for the maintenance of intracellular homeostasis of folates and antifolates for optimal folate-dependent one-carbon transfer reactions and antifolate-induced cytotoxic effects.

Once inside the cell, folates and antifolates (such as, for example, and without limitation, pemetrexed and pralatrexate) are polyglutamated by FPGS into polyglutamates. This process is required for biological activity. For example, polyglutamation facilitates retention (increases intracellular concentrations) and increases affinity for folate-dependent enzymes (including thymidylate synthase). The ability of cells to form polyglutamates also enhances the cytotoxic action of an antifolate, thereby making antifolates very effective cytotoxic agents.

The present applicant undertook to study the cytotoxic effects of polyglutamated forms of antifolates to assess their effectiveness in treating cancerous cells. Because polyglutamated forms of antifolates are not taken up by either normal or cancer cells (as discussed in greater detail below), the applicant postulated that if such polyglutamated forms could be directly delivered to cancer cells, the toxicity of the antifolates could be improved, with reduced undesirable toxicities to normal cells that may occur as a result of efflux of excess antifolate in the cancer cells.

In particular, excess amounts of antifolate present in the cancer cells may be returned to the circulatory system via high capacity ATP-dependent efflux pumps of folates and antifolates. This is true even when the antifolates are delivered using the targeted liposomal approach described in WO 2016/25882, the entire contents of which are herein incorporated by reference in its entirety. In other words, even though the techniques of WO 2016/25882 can deliver antifolates to cancer cells while substantially bypassing normal cells, the efflux of excess of the delivered antifolate can be returned to the circulatory system and be taken up by normal cells, resulting in undesirable toxicities. While these toxicities are significantly reduced as compared to toxicities associated with the traditional administration of free antifolates in the circulatory system of a patient, they are nonetheless undesirable. The antifolates and delivery systems described herein can further reduce the albeit significantly reduced toxic effects on normal cells achieved by WO 2016/25882, and provide even greater reductions in toxicity for normal cells.

The present inventors realized potential advantages of using polygulatamated antifolates for cancer treatment. For example, polyglutamates, especially pentaglutamates and higher order glutamates such as hexaglutamates, can permit a cell to more efficiently retain its folate pools. However, due to their high negative charge and other properties, polyglutamates such as pentaglutamates and hexaglutamated have no known cross cell membrane transport substrates.

The present disclosure describes advanced and improved techniques to deliver to cancer cells a different class of antifolates (e.g., polyglutamates) which were previously not able to be taken up by cancer cells. Because of the lack of cross cell membrane transport, the polyglutamates delivered to the cancer cells are effectively retained within the cancer cells. This reduces and/or eliminates toxicities associated with, for example, non-polyglutamated antifolates, such as monoglutamated antifolates because the polyglutamates are not returned to the circulatory system. Indeed, even if they were, they would not be picked up by healthy cells.

The therapeutic benefits provided by polyglutamated antifolate compositions and their uses are both numerous and surprising.

First, the active form of many cytotoxic agents, and antifolates in particular, is in the alpha (L-alpha or D-alpha) or D-gamma polyglutamated form and therefore, the delivery of the previously undeliverable polyglutamated form of the antifolate means that the drug is immediately active. Moreover, it is known that some solid tumors are low or deficient in FPGS activity and polyglutamation level. This means that tumors that are low in FPGS activity are more resistant to chemotherapy via non-polyglutamated drugs because the drugs, after entry into the cells, are still dependent on the low endogenous FPGS activity for activation.

Second, retention of drugs in their non-polyglutamated states is also problematic. Part of the problems in treating tumors, and especially tumors with low endogenous FPGS activities, is two-folds at least. The previous paragraph discusses the issue with low activation of drugs due to low levels of FPGS. In addition to this defect, non-polyglutamated drugs such as, non-polyglutamated pemetrexed, have limited retention in cells because they can be actively transported out of the cell. The transport of non-polyglutamated drugs (e.g., non-polyglutamated pemetrexed) is in itself a two-fold problem. Firstly, if the non-polyglutamated drug is transported out of the cell, it can no longer act within the cancer cell for treatment. Also, cytotoxic agents such as antifolates that are located outside of the cell can reenter other cells, including normal cells, and cause undesirable toxicity to normal cells. It is possible that upon entry into the cell, certain cellular processes might function to reduce the alpha (L-alpha or D-alpha) or D-gamma polyglutamated antifolates provided herein to monoglutamates. However, current testing suggests that the toxicity and activity of the provided polyglutamated antifolates kill the cells before such reduction occurs.

Third, because a polyglutamated antifolate is retained inside the cell and not transported extracellularly, the administration of the alpha (L-alpha or D-alpha) or D-gamma polyglutamated antifolate drug (e.g., intravenous administration) may be performed only for a limited time, therefore further reducing potential undesirable toxicity to normal tissue. A reduced administration time also improves patient comfort and reduces cost since the length of administration in a clinical setting can be proportionally reduced. The retention of the alpha (L-alpha or D-alpha) or D-gamma polyglutamated antifolate within for example, tumor cells means that the tumor cells would be less likely to recover from the treatement, even after the drug is removed from the extracellular milieu (e.g., intravenous administration is stopped).

Fourth, the activity of the disclosed liposomal alpha (L-alpha or D-alpha) or D-gamma polyglutamated antifolates such as the targeted- and non-targeted-pegylated liposomal polyglutamated antifolates is undiminished in tumors even if the tumor is FPGS deficient. That is because there is no reliance of FPGS to activate the drug.

For all the above stated reasons, the untargeted and targeted pegylated liposomal alpha (L-alpha or D-alpha) or D-gamma polyglutamated antifolate has a higher therapeutic index than a non polyglutamated antifolate that is delivered in the same method. That is, the inventors expect the drug to have minimal/reduced toxicity and for patients to tolerate higher dosages of the drug with lower side effects. The benefits described above are absent in an administered drug that is not polyglutamated.

A non-exhaustive list of alpha (L-alpha or D-alpha) or D-gamma polyglutamated antifolates that are encompassed by the compositions and methods of the disclosure include polyglutamated methotrexate (MTX), polyglutamated pemetrexed (PMX), polyglutamated lometrexol (LTX), polyglutamated AG2034, polyglutamated raltitrexed (RTX), polyglutamated piritrexim, polyglutamated pralatrexate, polyglutamated AG2034, polyglutamated GW1843, polyglutamated aminopterin, and polyglutamated LY309887.

In some embodiments, the alpha (L-alpha or D-alpha) or D-gamma pentaglutamated antifolate is a member selected from the group consisting of: pentaglutamated methotrexate (MTX), pentaglutamated pemetrexed (PMX), pentaglutamated lometrexol (LTX), pentaglutamated AG2034, pentaglutamated raltitrexed (RTX), pentaglutamated piritrexim, pentaglutamated pralatrexate, pentaglutamated AG2034, pentaglutamated GW1843, pentaglutamated aminopterin, and pentaglutamated LY309887.

In some embodiments, the alpha (L-alpha or D-alpha) or D-gamma hexaglutamated antifolate is a member selected from the group consisting of: hexaglutamated methotrexate (MTX), hexaglutamated pemetrexed (PMX), hexaglutamated lometrexol (LTX), hexaglutamated AG2034, hexaglutamated raltitrexed (RTX), hexaglutamated piritrexim, hexaglutamated pralatrexate, hexaglutamated AG2034, hexaglutamated GW1843, hexaglutamated aminopterin, and hexaglutamated LY309887.

In some embodiments, the polyglutamated antifolate compositions (e.g., polyglutamates and delivery vehicles such as liposomes containing the polyglutamates) composition are "isolated." As use herein, the term isolated refers to a composition which is in a form not found in nature. Isolated polyglutamated antifolate compositions include those which have been purified to a degree that they are no longer in a form in which they are found in nature. In some embodiments, a polyglutamated antifolate compositions composition which is isolated is substantially pure. Isolated compositions will be free or substantially free of material with which they are naturally associated such as other cellular components such as proteins and nucleic acids with which they may potentially be found in nature, or the environment in which they are prepared (e.g., cell culture). The polyglutamated antifolate compositions may be formulated with diluents or adjuvants and still for practical purposes be isolated—for example, the polyglutamated antifolate compositions will normally be mixed with pharmaceutically acceptable carriers or diluents when used in diagnosis or therapy. In some embodiments, the isolated polyglutamated antifolate compositions (e.g., polyglutamates and delivery vehicles such as liposomes containing the polyglutamates contain at less than 1% or less than 0.1% DNA or proteins.

In some embodiments, greater than 70%, 80% or 90% of the polyglutamated antifolate in a provided liposomal composition is pentaglutamated. In some embodiments, greater than 70%, 80% or 90% of the polyglutamated antifolate in a provided composition is pentaglutamated. In some embodiments, greater than 70%, 80% or 90% of the polyglutamated antifolate in a liposomal composition is pentaglutamated. In some embodiments, greater than 70%, 80% or 90% of the polyglutamated antifolate in a provided composition is hexaglutamated. In some embodiments, greater than 70%, 80% or 90%) of the polyglutamated antifolate in a liposomal composition is hexaglutamated. In some embodiments, greater than 70%, 80% or 90% of the polyglutamated antifolate in the composition has 5-10 or ≥4 glutamyl groups. In some embodiments, greater than 70%, 80% or 90% of the polyglutamated antifolate in a liposomal composition has 5-10 or ≥4 glutamyl groups.

In some embodiments, the alpha (L-alpha or D-alpha) or D-gamma polyglutamated antifolate compositions (e.g., polyglutamates and delivery vehicles such as liposomes containing the polyglutamates) are in an aqueous solution. In some embodiments, the polyglutamated antifolate is at a concentration of 100 ng/ml to 700 mg/ml. In some embodiments, the polyglutamated antifolate is at a concentration of greater than 100 ng/ml, 250 ng/ml, 500 ng/ml, 750 ng/ml, 1 ug/ml, 100 ug/ml, 250 ug/ml, 500 ug/ml, 750 ug/ml, 1 mg/ml, 100 mg/ml, 250 mg/ml, or 500 mg/ml. In some embodiments, the concentration of the liposomes containing the polyglutamated antifolates is at a concentration of 100 ng/ml to 1 mg/ml. In some embodiments, the concentration of greater than 100 ng/ml, 250 ng/ml, 500 ng/ml, 750 ng/ml, 1 ug/ml, 100 ug/ml, 250 ug/ml, 500 ug/ml, 750 ug/ml, or 1 mg/ml.

Figure 1:
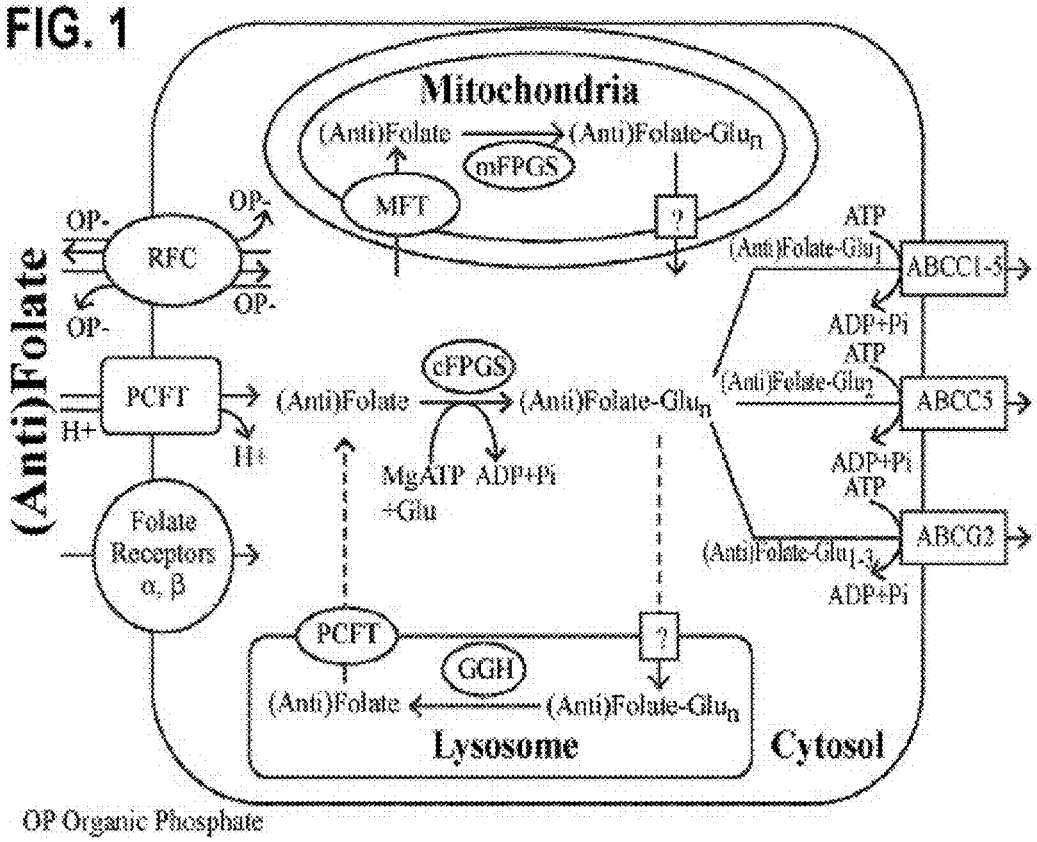
Figure 2:
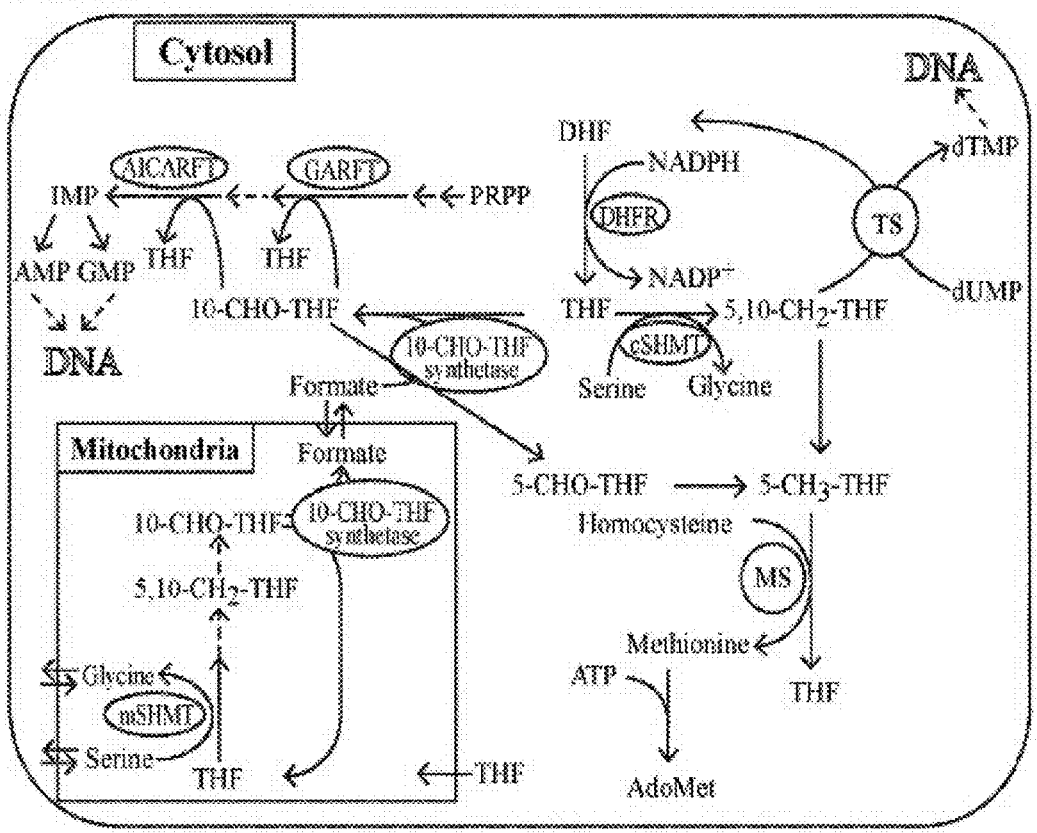
Figure 3A:
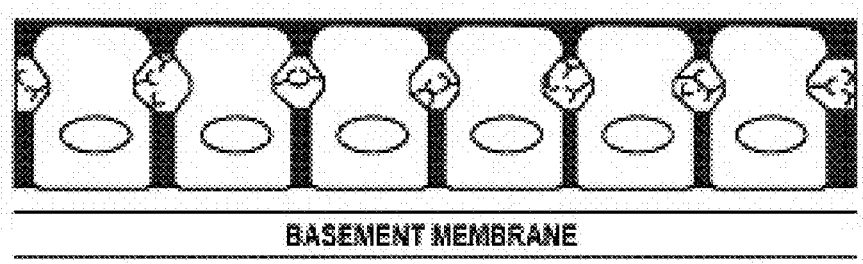
Figure 3B:
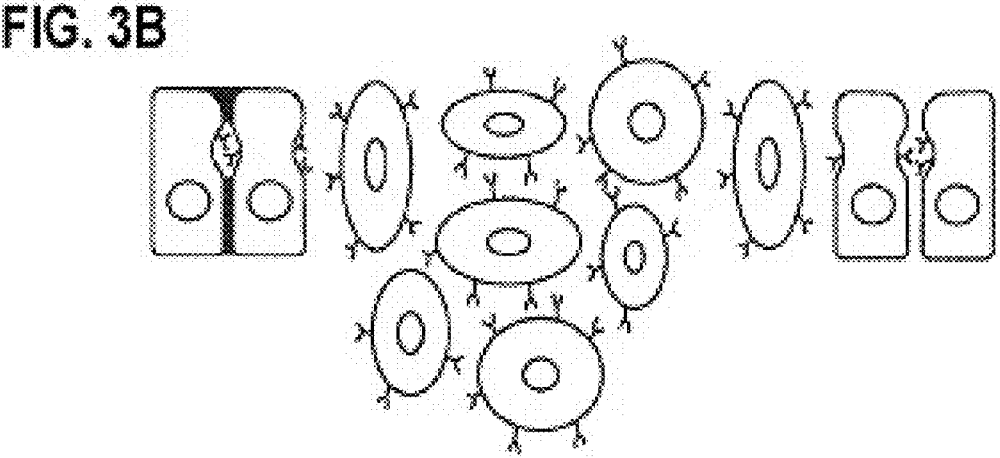
Figure 4:
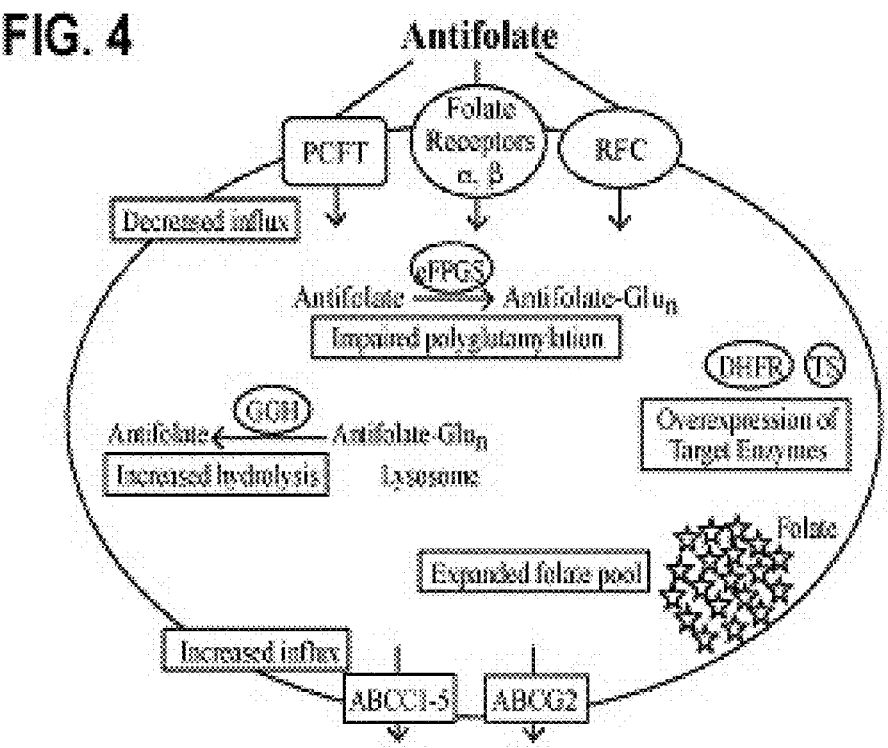
FIG. 4 shows molecular mechanisms underlying antifolate resistance in cancer.

Pemetrexed, for example, is a multitargeted antifolate that inhibits at least three enzymes involved in folate metabolism and purine and pyrimidine synthesis. These enzymes are thymidylate synthase (TS), dihydrofolate reductase (DHFR), and glycinamide ribonucleotide formyltransferase (GARFT) (see, FIG. 2). Pemetrexed is approved and remains an important treatment for mesothelioma and non-small-cell lung cancers.

In the treatment of mesothelioma and non-small cell lung cancer, pemetrexed is approved in combination with cisplatin for the therapy of malignant mesothelioma, and for the initial as well as maintenance treatment of patients with non-small-cell lung cancers. Pemetrexed has demonstrated equivalent efficacy to docetaxel, but with significantly less toxicity, in second-line treatment of non-small-cell lung cancer. The most common and serious toxicities of pemetrexed—myelosuppresion and mucositis—have been significantly ameliorated by folic acid and vitamin B12 supplementation, but undesirable toxicities remain. In some particular embodiments, the alpha (L-alpha or D-alpha) or D-gamma polyglutamated antifolate is polyglutamated pemetrexed (PMX). In further embodiments, the alpha or D-gamma polyglutamated antifolate is pentaglutamated PMX. In further embodiments, the alpha or D-gamma polyglutamated antifolate is hexaglutamated PMX.

These toxicities can be reduced, minimized and/or eliminated using a polyglutamated antifolate as described herein. In some particular embodiments described herein, the alpha (L-alpha or D-alpha) or D-gamma polyglutamated antifolate is polyglutamated pemetrexed (PMX). In further embodiments, the alpha or D-gamma polyglutamated antifolate is pentaglutamated PMX. In further embodiments, the alpha or D-gamma polyglutamated antifolate is hexaglutamated PMX.

In some particular embodiments, the alpha or D-gamma polyglutamated antifolate is polyglutamated raltitrexed (RTX). In further embodiments, the alpha or D-gamma polyglutamated antifolate is pentaglutamated RTX. In further embodiments, the alpha or D-gamma polyglutamated antifolate is hexaglutamated RTX.

Lometrexol was the first potent antifolate inhibitory to purine synthesis due to its direct suppression of glycinamide ribonucleotide transferase (GARFT) activity. In particular embodiments, the alpha (L-alpha or D-alpha) or D-gamma polyglutamated antifolate is polyglutamated lometrexol (LTX). In further embodiments, the alpha or D-gamma polyglutamated antifolate is pentaglutamated LTX). In further embodiments, the alpha or D-gamma polyglutamated antifolate is hexaglutamated LTX.

As discussed herein, the use of antifolates such as pemetrexed in clinical setting has led to a serious clinical dilemma. Fast renewing normal tissue cells such as bone marrow, GI tract and oral mucosa cells have been shown to be susceptible to the cytotoxic effect of this class of drugs, because they also replicate their DNA more frequently. Consequently, in clinical practice, use of antifolates has often resulted in severe and life-threatening hematologic and non-hematologic toxic side-effects. Furthermore, the toxicities were deemed on one hand to be dose-limiting and on the other hand to hamper the ability to achieve good efficacy. Due to their associated severe life-threatening toxicities, promising antifolates either failed during development e.g. lometrexol or have had limited use in clinical practice e.g. raltitrexed (TOMUDEX®) and pemetrexed (ALIMTA®).

The factors described herein are also at the core of the mechanisms of resistance to antifolates in general and those whose antitumor activity is potentiated by polyglutamation such as methotrexate, pemetrexed, lometrexol, and raltitrexed.

The disclosed polyglutamated antifolates provide a strategy for overcoming the pharmacological challenges associated with the dose limiting toxicities, associated with antifolate drugs. The provided methods deliver to tumor cells a previously undeliverable (due to lack of transport mechanisms) polyglutamate form of the antifolate payload while (1) minimizing/reducing exposure to normal tissue cells, (2) optimizing/improving the cytotoxic effect of the antifolate on cancer cells and (3) minimizing/reducing the impact of the efflux pumps.

The alpha (L-alpha or D-alpha) or D-gamma polyglutamated chemical entities provided herein achieve many advantages over counterpart antifolates that are not delivered to cells in a polyglutamated form. For example, the alpha or D-gamma polyglutamated antifolates are administered as a bolus that bypass the FPGS-induced polyglutamation activity required for antifolates such as PMX, MTX, RTX, and LTX to have increased activity (via increased binding affinity for folate-dependent enzymes) and cellular retention. As reflected in the figure s, disclosure, and examples, herein, retention of higher polyglutamates (e.g., drugs containing 4, 5, or more than 5 glutamate groups) in a cell is the direct function of their chain length. Thus, significant fractions of unbound MTX-Glu4 and most of MTX-Glu5 remain in the cells for at least 24 hours after removal of extracellular drug and continue to exert an inhibitory effect on DHFR, DNA synthesis, and cell viability.

The new chemical entities are designed not only to increase and/or maximize tumor intracellular concentration of polyglutamated form of antifolates by carefully leveraging cell and molecular biology of the folate pathways, but also by exploiting the differential cell polarity between tumor and normal tissue, where a cancer specific morphology has been unappreciated as useful to the goal to mitigating the clinical and pharmacological challenges associated with the use of antifolates for cancer treatment. Furthermore, the new chemical entities will minimize tumor cell resistance treatment that is mediated by cell efflux pumps.

By way of example and without limitation, a targeted liposomal polyglutamated antifolate composition may include a pegylated liposome including an entrapped and/or encapsulated alpha (L-alpha or D-alpha) or D-gamma polyglutamated antifolate; and a targeting moiety comprising an amino acid chain (e.g., an antibody or antibody fragment), the amino acid chain comprising a plurality of amino acids, the targeting moiety having a specific affinity for at least one type of folate receptor, the targeting moiety attached to one or both of a PEG and an exterior of the liposome. In a preferred embodiment, the liposome-encapsulated alpha or D-gamma polyglutamated antifolate (LPA) may be a pentaglutamate or hexaglutamate form of pemetrexed or pentaglutamate or hexaglutamate form of any suitable antifolate.

In some embodiments, the targeted, optionally pegylated, liposomal polyglutamated antifolate composition includes a pegylated liposome including an entrapped and/or encapsulated alpha (L-alpha or D-alpha) or D-gamma polyglutamated antifolate; and a targeting moiety comprising an amino acid chain (e.g., an antibody or antibody fragment), the amino acid chain comprising a plurality of amino acids, the targeting moiety having a specific affinity for at least one type of folate receptor. The specific affinity may be defined, for example, and without limitation, to include an equilibrium dissociation constant (Kd) in a range of $0.5 \times 10^{-10}$ to $10 \times 10^{-6}$ moles [0.05 nanoMole to 10 µMole] for at least one type of folate receptor, the targeting moiety attached to one or both of a PEG and an exterior of the liposome.

In some embodiments, the targeted, optionally pegylated, liposomal composition comprises a pegylated liposome including an entrapped (e.g., contained/encapsulated); and a targeting moiety comprising an amino acid chain (e.g., an antibody or antibody fragment), the amino acid chain comprising a plurality of amino acids, the targeting moiety having a specific affinity for at least one type of folate receptor. In some embodiments, the specific affinity of the targeting moiety is an equilibrium dissociation constant (Kd) in a range of $0.5 \times 10^{-10}$ to $10 \times 10^{-6}$ moles for at least one type of folate receptor. In further embodiments, the targeting moiety is attached to one or both of a PEG and an exterior of the liposome.

There are at least three primary limitations in the use of the free cytotoxic agents such as antifolates that require polyglutamation for enhanced activity. The new chemical entities contemplated and disclosed herein are designed to address these fundamental limitations. These limitations include the following. The first limitation is toxicity to normal tissue cells; this toxicity is due to cell uptake of the monoglutamate form, via RFCs or PCFTs for example, and its subsequent intracellular conversion by FPGS into the alpha (L-alpha or D-alpha) or D-gamma polyglutamated forms with enhanced cellular cytotoxicity coupled with prolonged cell retention in normal tissue cells. The second limitation is delivering adequate amount of the most active polyglutamate form of the drug because such compound cannot cross the cell membrane. Instead, its intracellular availability depends on the ability of the cell to polyglutamate the monoglutamate form of the drug transported from extracellular environment. The third limitation is retaining within the tumor cells adequate levels of the most cytotoxic forms such as the pentaglutamate or hexaglutamate forms of the antifolate. This is due to the cancer cells ability to downregulate FPGS leading to decreased polyglutamation and, in some instances, to increase the breakdown of polyglutamated forms by GGH as well as upregulation of efflux pumps (ATP-cassettes) which have the ability to pump out of the cell mono and other lower glutamated forms (1-, 2-, 3)-glutamates, but not the higher (e.g., pentaglutamated or hexaglutamated) forms of folates and their analogs.

The polyglumated antifolate new chemical entities contemplated and disclosed herein do not suffer from the above drawbacks and limitations, and are designed to address the three limitations described herein. Indeed, the new chemical entities will minimize the pharmacological challenges associated with systemic transport, cell uptake and intra tumor cell accumulation of the active form of the drug. The new chemical entities of the present disclosure preferentially target tumor cells for exposure to polyglutamated forms (e.g., pentaglutamated and hexaglutamated) of antifolate and/or minimizes exposure of such antifolate drug cocktail to normal cells, especially the high turnover (e.g., fast replicating) normal cells in the bone marrow and in the epithelial lining of the gastrointestinal tract.

In some embodiments, the disclosure provides a composition comprising an alpha (L-alpha or D-alpha) or D-gamma polyglutamated antifolate. In further embodiments, the composition comprises an alpha (L-alpha or D-alpha) or D-gamma pentaglutamated antifolate. In further embodiments, the composition comprises an alpha (L-alpha or D-alpha) or D-gamma hexaglutamated antifolate.

In some embodiments, the polyglutamated antifolate contains 1, 2, 3, 4, 5, 6, 7, 8, 9, or 1-10 alpha peptide linkages. In some embodiments, the polyglutamated antifolate contains 1, 2, 3, 4, 5, 6, 7, 8, 9, or 1-10 L-alpha peptide linkages. In some embodiments, the polyglutamated antifolate contains 11, 2, 3, 4, 5, 6, 7, 8, 9, or 1-10 D-alpha peptide linkages. In some embodiments, the polyglutamated antifolate contains 1, 2, 3, 4, 5, 6, 7, 8, 9, or 1-10, or 1-10 D-gamma peptide linkages. In some embodiments, the polyglutamated antifolate further contains 0, 1, 2, 3, 4, 5, 6, 8, 8, 9, or 1-10 L-gamma peptide linkages in addition to one or more of the above-described linkages. For example, in some embodiments, the polyglutamated antifolate contains 1, 2, 3, 4, 5, 6, 7, 8, 9, or 1-10 alpha peptide linkages and 1, 2, 3, 4, 5, 6, 7, 8, 9, or 1-10 L-gamma peptide linkages. In further embodiments, the polyglutamated antifolate contains 1, 2, 3, 4, 5, 6, 7, 8, 9, or 1-10 L-alpha peptide linkages and 11, 2, 3, 4, 5, 6, 7, 8, 9, or 1-10 L-gamma peptide linkages. Also, in further embodiments, the polyglutamated antifolate contains 1, 2, 3, 4, 5, 6, 7, 8, 9, or 1-10 D-alpha peptide linkages and 1, 2, 3, 4, 5, 6, 7, 8, 9, or 1-10 L-gamma peptide linkages. In additional embodiments, the polyglutamated antifolate contains 1, 2, 3, 4, 5, 6, 7, 8, 9, or 1-10 D-gamma peptide linkages and 1, 2, 3, 4, 5, 6, or 1-10 L-gamma peptide linkages. In additional embodiments, the polyglutamated antifolate contains 1, 2, 3, 4, 5, 6, 7, 8, 9, or 1-10 L-alpha peptide linkages and 1, 2, 3, 4, 5, 6, 7, 8, 9, or 1-10 D-alpha peptide linkages. In some embodiments, the polyglutamated antifolate contains 1, 2, 3, 4, 5 or 1-10 L-alpha peptide linkages and 1, 2, 3, 4, 5, 6, 7, 8, 9, or 1-10 D-gamma peptide linkages. In some embodiments, the polyglutamated antifolate contains 1, 2, 3, 4, 5, 6, 7, 8, 9, or 1-10 D-alpha peptide linkages and 1, 2, 3, 4, 5, 6, 7, 8, 9, or 1-10 D-gamma peptide linkages.

According to some embodiments, the alpha (L-alpha or D-alpha) or D-gamma polyglutamated antifolate is a member selected from the group consisting of: polyglutamated methotrexate (MTX), polyglutamated pemetrexed (PMX), polyglutamated lometrexol (LTX), polyglutamated AG2034, polyglutamated raltitrexed (RTX), polyglutamated piritrexim, polyglutamated pralatrexate, polyglutamated AG2034, polyglutamated GW1843, polyglutamated aminopterin, and polyglutamated LY309887. In further embodiments, the alpha or D-gamma polyglutamated member is pentaglutamated. In further embodiments, the alpha or D-gamma polyglutamated member is hexaglutamated In one embodiment, the composition comprises alpha or D-gamma polyglutamated PMX, MTX, RTX, or LTX. In a further embodiment the composition comprises alpha or D-gamma pentaglutamated PMX, MTX, RTX, or LTX.

In one embodiment, the composition comprises alpha or D-gamma polyglutamated PMX, MTX, RTX, or LTX. In a further embodiment the composition comprises alpha or D-gamma hexaglutamated PMX, MTX, RTX, or LTX.

In one embodiment, the composition comprises alpha or D-gamma polyglutamated PMX. In a further embodiment the composition comprises alpha or D-gamma pentaglutamated PMX.

In one embodiment, the composition comprises alpha or D-gamma polyglutamated PMX. In a further embodiment the composition comprises alpha or D-gamma hexaglutamated PMX.

In another embodiment, the composition comprises alpha or D-gamma polyglutamated MTX. In a further embodiment the composition comprises alpha or D-gamma pentaglutamated MTX.

In another embodiment, the composition comprises alpha or D-gamma polyglutamated MTX. In a further embodiment the composition comprises alpha or D-gamma hexaglutamated MTX.

In another embodiment, the composition comprises alpha or D-gamma polyglutamated RTX. In a further embodiment the composition comprises alpha or D-gamma pentaglutamated RTX.

In another embodiment, the composition comprises alpha or D-gamma polyglutamated RTX. In a further embodiment the composition comprises alpha or D-gamma hexaggutamated RTX.

In an additional embodiment, the composition comprises alpha or D-gamma polyglutamated LTX. In a further embodiment the composition comprises alpha or D-gamma pentaglutamated LTX.

(RTX), polyglutamated piritrexim, polyglutamated pralatrexate, polyglutamated AG2034, polyglutamated GW1843, polyglutamated aminopterin, and polyglutamated LY309887. In further embodiments, the alpha or D-gamma polyglutamated member is pentaglutamated. In further embodiments, the alpha or D-gamma polyglutamated member is hexaglutamated In one embodiment, the composition comprises alpha or D-gamma polyglutamated PMX, MTX, RTX, or LTX. In a further embodiment the composition comprises alpha or D-gamma pentaglutamated PMX, MTX, RTX, or LTX. In a further embodiment the composition comprises alpha or D-gamma hexaglutamated PMX, MTX, RTX, or LTX.

In one embodiment, the composition comprises alpha or D-gamma polyglutamated PMX. In a further embodiment the composition comprises alpha or D-gamma pentaglutamated PMX. In a further embodiment the composition comprises alpha or D-gamma hexaglutamated PMX.

In another embodiment, the composition comprises alpha or D-gamma polyglutamated MTX. In a further embodiment the composition comprises alpha or D-gamma pentaglutamated MTX. In a further embodiment the composition comprises alpha or D-gamma hexaglutamated MTX.

In another embodiment, the composition comprises alpha or D-gamma polyglutamated RTX. In a further embodiment the composition comprises alpha or D-gamma pentaglutamated RTX. In a further embodiment the composition comprises alpha or D-gamma hexaglutamated RTX.

In an additional embodiment, the composition comprises alpha or D-gamma polyglutamated LTX. In a further embodiment the composition comprises alpha or D-gamma pentaglutamated LTX. In a further embodiment the composition comprises alpha or D-gamma hexaglutamated LTX.

In one embodiment, the composition comprises L-alpha polyglutamated PMX, MTX, RTX, or LTX. In a further embodiment the composition comprises L-alpha pentaglutamated PMX, MTX, RTX, or LTX. In a further embodiment the composition comprises L-alpha hexaglutamated PMX, MTX, RTX, or LTX.

In one embodiment, the composition comprises L-alpha polyglutamated PMX. In a further embodiment the composition comprises L-alpha pentaglutamated PMX. In a further embodiment the composition comprises L-alpha hexaglutamated PMX.

In another embodiment, the composition comprises L-alpha polyglutamated MTX. In a further embodiment the composition comprises L-alpha pentaglutamated MTX. In a further embodiment the composition comprises L-alpha hexaglutamated MTX.

In another embodiment, the composition comprises L-alpha polyglutamated RTX. In a further embodiment the composition comprises L-alpha pentaglutamated RTX. In a further embodiment the composition comprises L-alpha hexaglutamated RTX.

In an additional embodiment, the composition comprises L-alpha polyglutamated LTX. In a further embodiment the composition comprises L-alpha pentaglutamated LTX. In a further embodiment the composition comprises L-alpha hexaglutamated LTX In one embodiment, the composition comprises D-alpha polyglutamated PMX, MTX, RTX, or LTX. In a further embodiment the composition comprises D-alpha pentaglutamated PMX, MTX, RTX, or LTX. In a further embodiment the composition comprises D-alpha hexaglutamated PMX, MTX, RTX, or LTX.

In one embodiment, the composition comprises D-alpha polyglutamated PMX. In a further embodiment the composition comprises D-alpha pentaglutamated PMX. In a further embodiment the composition comprises D-alpha hexaglutamated PMX.

In another embodiment, the composition comprises D-alpha polyglutamated MTX. In a further embodiment the composition comprises D-alpha pentaglutamated MTX. In a further embodiment the composition comprises D-alpha hexaglutamated MTX.

In another embodiment, the composition comprises D-alpha polyglutamated RTX. In a further embodiment the composition comprises D-alpha pentaglutamated RTX. In a further embodiment the composition comprises D-alpha hexaglutamated RTX.

In an additional embodiment, the composition comprises D-alpha polyglutamated LTX. In a further embodiment the composition comprises D-alpha pentaglutamated LTX. In a further embodiment the composition comprises D-alpha hexaglutamated LTX.

In one embodiment, the composition comprises D-gamma polyglutamated PMX, MTX, RTX, or LTX. In a further embodiment the composition comprises D-gamma pentaglutamated PMX, MTX, RTX, or LTX. In a further embodiment the composition comprises D-gamma hexaglutamated PMX, MTX, RTX, or LTX In one embodiment, the composition comprises D-gamma polyglutamated PMX. In a further embodiment the composition comprises D-gamma pentaglutamated PMX. In a further embodiment the composition comprises D-gamma hexaglutamated PMX.

In another embodiment, the composition comprises D-gamma polyglutamated MTX. In a further embodiment the composition comprises D-gamma pentaglutamated MTX. In a further embodiment the composition comprises D-gamma hexaglutamated MTX.

In another embodiment, the composition comprises D-gamma polyglutamated RTX. In a further embodiment the composition comprises D-gamma pentaglutamated RTX. In a further embodiment the composition comprises D-gamma hexaglutamated RTX.

In an additional embodiment, the composition comprises D-gamma polyglutamated LTX. In a further embodiment the composition comprises D-gamma pentaglutamated LTX. In a further embodiment the composition comprises D-gamma hexaglutamated LTX.

In additional embodiments, the disclosure provides a liposomal alpha (L-alpha or D-alpha) or D-gamma polyglutamated antifolate composition comprising a polyglutamated antifolate. In some embodiments, the liposome is optionally pegylated (PLPA). In some embodiments, the PLPA composition comprises a pentaglutamated antifolate. In some embodiments, the PLPA composition comprises a hexaglutamated antifolate. In some embodiments, the PLPA liposome is anionic or neutral. In other embodiments, the PLPA liposome is cationic. In some embodiments, the PLPA composition comprises at least 10% liposome entrapped comprises alpha or D-gamma polyglutamated antifolate. In some embodiments, the PLPA liposomes have a diameter in the range of 20 nm to 200 nm. In further embodiments, the liposomes have a diameter in the range of 80 nm to 120 nm.

According to some embodiments, the PLPA comprises an alpha (L-alpha or D-alpha) or D-gamma polyglutamated antifolate selected from the group consisting of: polyglutamated MTX, polyglutamated PMX, polyglutamated LTX, polyglutamated AG2034, polyglutamated RTX, polyglutamated piritrexim, polyglutamated pralatrexate, polyglutamated AG2034, polyglutamated GW1843, polyglutamated aminopterin, and polyglutamated LY309887. In further embodiments, the alpha or D-gamma polyglutamated antifolate is pentaglutamated. In further embodiments, the alpha or D-gamma polyglutamated antifolate is hexaglutamated.

In one embodiment, the PLPA comprises an alpha (L-alpha or D-alpha) or D-gamma polyglutamated PMX, MTX, RTX, or LTX. In a further embodiment the PLPA comprises alpha or D-gamma pentaglutamated PMX, MTX, RTX, or LTX. In a further embodiment the PLPA comprises alpha or D-gamma hexaglutamated PMX, MTX, RTX, or LTX.

In one embodiment, the PLPA comprises alpha (L-alpha or D-alpha) or D-gamma polyglutamated PMX. In a further embodiment the PLPA comprises alpha or D-gamma pentaglutamated PMX. In a further embodiment the PLPA comprises alpha or D-gamma hexaglutamated PMX.

In another embodiment, the PLPA comprises alpha (L-alpha or D-alpha) or D-gamma polyglutamated MTX. In a further embodiment the PLPA comprises alpha or D-gamma pentaglutamated MTX. In a further embodiment the PLPA comprises alpha or D-gamma hexaglutamated MTX.

In another embodiment, the PLPA comprises alpha (L-alpha or D-alpha) or D-gamma polyglutamated RTX. In a further embodiment the PLPA comprises alpha or D-gamma pentaglutamated RTX. In a further embodiment the PLPA comprises alpha or D-gamma hexaglutamated RTX.

In an additional embodiment, the PLPA comprises alpha (L-alpha or D-alpha) or D-gamma polyglutamated LTX. In a further embodiment the PLPA comprises alpha or D-gamma pentaglutamated LTX. In a further embodiment the PLPA comprises alpha or D-gamma hexaglutamated LTX.

According to some embodiments, the PLPA comprises an alpha (L-alpha or D-alpha) polyglutamated antifolate selected from the group consisting of: polyglutamated MTX, polyglutamated PMX, polyglutamated LTX, polyglutamated AG2034, polyglutamated RTX, polyglutamated piritrexim, polyglutamated pralatrexate, polyglutamated AG2034, polyglutamated GW1843, polyglutamated aminopterin, and polyglutamated LY309887. In further embodiments, the alpha polyglutamated antifolate is pentaglutamated. In additional embodiments, the alpha polyglutamated antifolate is hexaglutamated.

In one embodiment, the PLPA comprises an alpha (L-alpha or D-alpha) polyglutamated PMX, MTX, RTX, or LTX. In a further embodiment the PLPA comprises alpha pentaglutamated PMX, MTX, RTX, or LTX. In a further embodiment the PLPA comprises alpha hexaglutamated PMX, MTX, RTX, or LTX In one embodiment, the PLPA comprises alpha (L-alpha or D-alpha) polyglutamated PMX. In a further embodiment the PLPA comprises alpha pentaglutamated PMX. In a further embodiment the PLPA comprises alpha hexaglutamated PMX.

In another embodiment, the PLPA comprises alpha (L-alpha or D-alpha) polyglutamated MTX. In a further embodiment the PLPA comprises alpha pentaglutamated MTX. In a further embodiment the PLPA comprises alpha hexaglutamated MTX.

In another embodiment, the PLPA comprises alpha (L-alpha or D-alpha) polyglutamated RTX. In a further embodiment the PLPA comprises alpha pentaglutamated RTX. In a further embodiment the PLPA comprises alpha hexaglutamated RTX.

In an additional embodiment, the PLPA comprises alpha (L-alpha or D-alpha) polyglutamated LTX. In a further embodiment the PLPA comprises alpha pentaglutamated LTX. In a further embodiment the PLPA comprises alpha hexaglutamated LTX.

According to some embodiments, the PLPA comprises L-alpha polyglutamated antifolate selected from the group consisting of: polyglutamated MTX, polyglutamated PMX, polyglutamated LTX, polyglutamated AG2034, polyglutamated RTX, polyglutamated piritrexim, polyglutamated pralatrexate, polyglutamated AG2034, polyglutamated GW1843, polyglutamated aminopterin, and polyglutamated LY309887. In further embodiments, the L-alpha polyglutamated antifolate is pentaglutamated. In further embodiments, the L-alpha polyglutamated antifolate is hexaglutamated.

In one embodiment, the PLPA comprises L-alpha polyglutamated PMX, MTX, RTX, or LTX. In a further embodiment the PLPA comprises L-alpha pentaglutamated PMX, MTX, RTX, or LTX. In a further embodiment the PLPA comprises L-alpha hexaglutamated PMX, MTX, RTX, or LTX In one embodiment, the PLPA comprises L-alpha polyglutamated PMX. In a further embodiment the PLPA comprises L-alpha pentaglutamated PMX. In a further embodiment the PLPA comprises L-alpha hexaglutamated PMX.

In another embodiment, the PLPA comprises L-alpha polyglutamated MTX. In a further embodiment the PLPA comprises L-alpha pentaglutamated MTX. In a further embodiment the PLPA comprises L-alpha hexaglutamated MTX.

In another embodiment, the PLPA comprises L-alpha polyglutamated RTX. In a further embodiment the PLPA comprises L-alpha pentaglutamated RTX. In a further embodiment the PLPA comprises L-alpha hexaglutamated RTX.

In an additional embodiment, the PLPA comprises L-alpha polyglutamated LTX. In a further embodiment the PLPA comprises L-alpha pentaglutamated LTX. In a further embodiment the PLPA comprises L-alpha hexaglutamated LTX.

According to some embodiments, the PLPA comprises D-alpha polyglutamated antifolate selected from the group consisting of: polyglutamated MTX, polyglutamated PMX, polyglutamated LTX, polyglutamated AG2034, polyglutamated RTX, polyglutamated piritrexim, polyglutamated pralatrexate, polyglutamated AG2034, polyglutamated GW1843, polyglutamated aminopterin, and polyglutamated LY309887. In further embodiments, the D-alpha polyglutamated antifolate is pentaglutamated. In further embodiments, the D-alpha polyglutamated antifolate is hexaglutamated.

In one embodiment, the PLPA comprises D-alpha polyglutamated PMX, MTX, RTX, or LTX. In a further embodiment the PLPA comprises D-alpha pentaglutamated PMX, MTX, RTX, or LTX. In a further embodiment the PLPA comprises D-alpha hexaglutamated PMX, MTX, RTX, or LTX.

In one embodiment, the PLPA comprises alpha D-alpha polyglutamated PMX. In a further embodiment the PLPA comprises D-alpha pentaglutamated PMX. In a further embodiment the PLPA comprises D-alpha hexaglutamated PMX.

In another embodiment, the PLPA comprises D-alpha polyglutamated MTX. In a further embodiment the PLPA comprises D-alpha pentaglutamated MTX. In a further embodiment the PLPA comprises D-alpha hexaglutamated MTX.

In another embodiment, the PLPA comprises D-alpha polyglutamated RTX. In a further embodiment the PLPA comprises D-alpha pentaglutamated RTX. In a further embodiment the PLPA comprises D-alpha hexaglutamated RTX.

In an additional embodiment, the PLPA comprises D-alpha polyglutamated LTX. In a further embodiment the PLPA comprises D-alpha pentaglutamated LTX. In a further embodiment the PLPA comprises D-alpha hexaglutamated LTX.

According to some embodiments, the PLPA comprises D-gamma polyglutamated antifolate selected from the group consisting of: polyglutamated MTX, polyglutamated PMX, polyglutamated LTX, polyglutamated AG2034, polyglutamated RTX, polyglutamated piritrexim, polyglutamated pralatrexate, polyglutamated AG2034, polyglutamated GW1843, polyglutamated aminopterin, and polyglutamated LY309887. In further embodiments, the D-gamma polyglutamated antifolate is pentaglutamated. In further embodiments, the D-gamma polyglutamated antifolate is hexaglutamated.

In one embodiment, the PLPA comprises D-gamma polyglutamated PMX, MTX, RTX, or LTX. In a further embodiment the PLPA comprises D-gamma pentaglutamated PMX, MTX, RTX, or LTX. In a further embodiment the PLPA comprises D-gamma hexaglutamated PMX, MTX, RTX, or LTX.

In one embodiment, the PLPA comprises D-gamma polyglutamated PMX. In a further embodiment the PLPA comprises D-gamma pentaglutamated PMX. In a further embodiment the PLPA comprises D-gamma hexaglutamated PMX.

In another embodiment, the PLPA comprises D-gamma polyglutamated MTX. In a further embodiment the PLPA comprises D-gamma pentaglutamated MTX. In a further embodiment the PLPA comprises D-gamma hexaglutamated MTX.

In another embodiment, the PLPA comprises D-gamma polyglutamated RTX. In a further embodiment the PLPA comprises D-gamma pentaglutamated RTX. In a further embodiment the PLPA comprises D-gamma hexaglutamated RTX.

In an additional embodiment, the PLPA comprises D-gamma polyglutamated LTX. In a further embodiment the PLPA comprises D-gamma pentaglutamated LTX. In a further embodiment the PLPA comprises D-gamma hexaglutamated LTX.

Liposome

In some embodiments, an untargeted or targeted pegylated liposomal alpha (L-alpha or D-alpha) or D-gamma polyglutamated antifolate is provided. In some embodiments, the targeted pegylated liposomal polyglutamated antifolate may comprise a liposome including an interior space; an alpha (L-alpha or D-alpha) or D-gamma polyglutamated antifolate disposed within the interior space; a PEG molecule attached to an exterior of the liposome; and a targeting moiety comprising a protein (e.g., an antibody or antibody fragment) with specific affinity for at least one antigen expressed on the surface of the cancer cell (e.gs., a folate receptor (e.g., FR-$\alpha$, FR-$\beta$ and/or FR-$\delta$)) the targeting moiety attached to at least one of the PEG and the exterior of the liposome.

The liposomes contained in the disclosed liposome composition can be any liposome known in the art. However, it will be understood by one skilled in the art that liposomal encapsulation of any particular drug, such as, and without limitation, the alpha (L-alpha or D-alpha) or D-gamma polyglutamated antifolates discussed herein, may involve substantial routine experimentation to achieve a useful and functional liposomal formulation. In general, the provided liposomes may have any liposome structure, e.g., structures having an inner space sequestered from the outer medium by one or more lipid bilayers, or any microcapsule that has a semi-permeable membrane with a lipophilic central part where the membrane sequesters an interior. The lipid bilayer can be any arrangement of amphiphilic molecules characterized by a hydrophilic part (hydrophilic moiety) and a hydrophobic part (hydrophobic moiety). Usually amphiphilic molecules in a bilayer are arranged into two dimensional sheets in which hydrophobic moieties are oriented inward the sheet while hydrophilic moieties are oriented outward. Amphiphilic molecules forming the provided liposomes can be any known or later discovered amphiphilic molecules, e.g., lipids of synthetic or natural origin or biocompatible lipids. The liposomes can also be formed by amphiphilic polymers and surfactants, e.g., polymerosomes and niosomes. For the purpose of this disclosure, without limitation, these liposome-forming materials also are referred to as "lipids".

The liposome composition formulations provided herein can be in liquid or dry form such as a dry powder or dry cake. The dry powder or dry cake may have undergone primary drying under, for example, lyophilization conditions or optionally, the dry cake or dry powder may have undergone both primary drying only or both primary drying and secondary drying. In the dry form, the powder or cake may, for example, have between 1% to 6% moisture, for example, such as between 2% to 5% moisture or between 2% to 4% moisture. One example method of drying is lyophilization (also called freeze-drying, or cyrodessication). Any of the compositions and methods of the disclosure may include liposomes, lyophilized liposomes or liposomes reconstituted from lyophilized liposomes. In some embodiments, the disclosed compositions and methods include one or more lyoprotectants or cryoprotectants. These protectants are typically polyhydroxy compounds such as sugars (mono-, di-, and polysaccharides), polyalcohols, and their derivatives, glycerol, or polyethyleneglycol, trehalose, maltose, sucrose, glucose, lactose, dextran, glycerol, or aminoglycosides. In further embodiments, the lyoprotectants or cryoprotectants comprise up to 10% or up to 20% of a solution outside the liposome, inside the liposome, or both outside and inside the liposome.

In some embodiments, the liposomes include a steric stabilizer that increases their longevity in circulation. One or more steric stabilizers such as a hydrophilic polymer (Polyethylene glycol (PEG)), a glycolipid (monosialoganglioside (GM1)) or others occupies the space immediately adjacent to the liposome surface and excludes other macromolecules from this space. Consequently, access and binding of blood plasma opsonins to the liposome surface are hindered, and thus interactions of macrophages with such liposomes, or any other clearing mechanism, are inhibited and longevity of the liposome in circulation is enhanced. In some embodiments, the steric stabilizer or the population of steric stabilizers is a PEG or a combination comprising PEG. In further embodiments, the steric stabilizer is a PEG or a combination comprising PEG with a number average molecular weight (Mn) of 200 to 5000 daltons. These PEG(s) can be of any structure such as linear, branched, star or comb structure and are commercially available.

The diameter of the disclosed liposomes is not particularly limited. In some embodiments, the liposomes have a diameter in the range of for example, 30-150 nm (nanometer). In other embodiments, the liposomes have a diameter in the range of 40-70 nm.

The properties of liposomes are influenced by the nature of lipids used to make the liposomes. A wide variety of lipids have been used to make liposomes. These include cationic, anionic and neutral lipids. In some embodiments, the liposomes comprising the alpha (L-alpha or D-alpha) or D-gamma polyglutamated antifolate are anionic or neutral. In other embodiments, the provided liposomes are cationic. The determination of the charge (e.g., anionic, neutral or cationic) can routinely be determined by measuring the zeta potential of the liposome. The zeta potential of the liposome can be positive, zero or negative. In some embodiments, the zeta potential of the liposome is less than or equal to zero. In some embodiments, the zeta potential of the liposome is in a range of 0 to −150 mV. In another embodiment, the zeta potential of the liposome is in the range of −30 to −50 mV.

In some embodiments, cationic lipids are used to make cationic liposomes which are commonly used as gene transfection agents. The positive charge on cationic liposomes enables interaction with the negative charge on cell surfaces. Following binding of the cationic liposomes to the cell, the liposome is transported inside the cell through endocytosis.

In some preferred embodiments, a neutral to anionic liposome is used. In a preferred embodiment, an anionic liposome is used. Using a mixture of, for example, neutral lipids such as HSPC and anionic lipids such as PEG-DSPE results in the formation of anionic liposomes which are less likely to non-specifically bind to normal cells. Specific binding to tumor cells can be achieved by using a tumor targeting antibody such as, for example, a folate receptor antibody, including, for example, folate receptor alpha antibody, folate receptor beta antibody and/or folate receptor delta antibody.

As an example, at least one (or some) of the lipids is/are amphipathic lipids, defined as having a hydrophilic and a hydrophobic portions (typically a hydrophilic head and a hydrophobic tail). The hydrophobic portion typically orients into a hydrophobic phase (e.g., within the bilayer), while the hydrophilic portion typically orients toward the aqueous phase (e.g., outside the bilayer). The hydrophilic portion can comprise polar or charged groups such as carbohydrates, phosphate, carboxylic, sulfato, amino, sulfhydryl, nitro, hydroxy and other like groups. The hydrophobic portion can comprise apolar groups that include without limitation long chain saturated and unsaturated aliphatic hydrocarbon groups and groups substituted by one or more aromatic, cyclo-aliphatic or heterocyclic group(s). Examples of amphipathic compounds include, but are not limited to, phospholipids, aminolipids and sphingolipids.

Typically, for example, the lipids are phospholipids. Phospholipids include without limitation phosphatidylcholine, phosphatidylethanolamine, phosphatidylglycerol, phosphatidylinositol, phosphatidylserine, and the like. It is to be understood that other lipid membrane components, such as cholesterol, sphingomyelin, and cardiolipin, can be used.

The lipids comprising the liposomes provided herein can be anionic and neutral (including zwitterionic and polar) lipids including anionic and neutral phospholipids. Neutral lipids exist in an uncharged or neutral zwitterionic form at a selected pH. At physiological pH, such lipids include, for example, dioleoylphosphatidylglycerol (DOPG), diacylphosphatidylcholine, diacylphosphatidylethanolamine, ceramide, sphingomyelin, cephalin, cholesterol, cerebrosides and diacylglycerols. Examples of zwitterionic lipids include without limitation dioleoylphosphatidylcholine (DOPC), dimyristoylphosphatidylcholine (DMPC), and dioleoylphosphatidylserine (DOPS). Anionic lipids are negatively charged at physiological pH. These lipids include without limitation phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

Collectively, anionic and neutral lipids are referred to herein as non-cationic lipids. Such lipids may contain phosphorus but they are not so limited. Examples of non-cationic lipids include lecithin, lysolecithin, phosphatidylethanolamine, lysophosphatidylethanolamine, dioleoylphosphati-dylethanolamine (DOPE), dipalmitoyl phosphatidyl ethanolamine (DPPE), dimyristoylphosphoethanolamine (DMPE), distearoyl-phosphatidy 1-ethanolamine (DSPE), palmitoyloleoyl-phosphatidylethanolamine (POPE) palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), palmitoyloleyolphosphatidylglycerol (POPG), 16-0-monomethyl PE, 16-0-dimethyl PE, 18-1-trans PE, palmitoyloleoyl-phosphatidylethanolamine (POPE), 1-stearoyl-2-oleoylphosphatidyethanolamine (SOPE), phosphatidylserine, phosphatidylinositol, sphingomyelin, cephalin, cardiolipin, phosphatidic acid, cerebrosides, dicetylphosphate, and cholesterol.

The liposomes may be assembled using any liposomal assembly method using liposomal components (also referred to as liposome components) known in the art. Liposomal components include, for example, lipids such as DSPE, HSPC, cholesterol and derivatives of these components. Other suitable lipids are commercially available for example, by Avanti Polar Lipids, Inc. (Alabaster, Alabama, U.S.A.). A partial listing of available negatively or neutrally charged lipids suitable for making anionic liposomes, can be, for example, at least one of the following: DLPC, DMPC, DPPC, DSPC, DOPC, DMPE, DPPE, DOPE, DMPA•Na, DPPA•Na, DOPA•Na, DMPG•Na, DPPG•Na, DOPG•Na, DMPS•Na, DPPS•Na, DOPS•Na, DOPE-Glutaryl•(Na)2, Tetramyristoyl Cardiolipin•(Na)2, DSPE-mPEG-2000•Na, DSPE-mPEG-5000•Na, and DSPE-Maleimide PEG-2000•Na.

Lipid derivatives can include, for example, at least, the bonding (preferably covalent bonding) of one or more steric stabilizers and/or functional groups to the liposomal component after which the steric stabilizers and/or functional groups should be considered part of the liposomal components. Functional groups comprises groups that can be used to attach a liposomal component to another moiety such as a protein. Such functional groups include, at least, maleimide. These steric stabilizers include at least one from the group consisting of polyethylene glycol (PEG); poly-L-lysine (PLL); monosialoganglioside (GM1); poly(vinyl pyrrolidone) (PVP); poly(acrylamide) (PAA); poly(2-methyl-2-oxazoline); poly(2-ethyl-2-oxazoline); phosphatidyl polyglycerol; poly[N-(2-hydroxypropyl) methacrylamide]; amphiphilic poly-N-vinylpyrrolidones; L-amino-acid-based polymer; and polyvinyl alcohol.

Since the components of a liposome can include any molecule(s) (i.e., chemical/reagent/protein) that is bound to it, in some embodiments, the components of the provided liposomes include, at least, a member selected from the group DSPE, DSPE-PEG, DSPE-maleimide, HSPC; HSPC-PEG; HSPC-maleimide; cholesterol; cholesterol-PEG; and cholesterol-maleimide. In some embodiments, the components of the provided liposomes include DSPE, DSPE-PEG, DSPE-maleimide, HSPC; HSPC-PEG; HSPC-maleimide; cholesterol; cholesterol-PEG; and cholesterol-maleimide. In a preferred embodiment, the liposomal components that make up the liposome comprises DSPE; DSPE-FITC; DSPE-maleimide; cholesterol; and HSPC.

In some embodiments, at least one component of the liposome lipid bilayer is functionalized (or reactive). As used herein, a functionalized component is a component that comprises a reactive group that can be used to crosslink reagents and moieties to the lipid. If the lipid is functionalized, any liposome that it forms is also functionalized. In some embodiments, the reactive group is one that will react with a crosslinker (or other moiety) to form crosslinks. The reactive group in the liposome lipid bilayer is located anywhere on the lipid that allows it to contact a crosslinker and be crosslinked to another moiety (e.g., a steric stabilizer or targeting moiety). In some embodiments, the reactive group is in the head group of the lipid, including for example a phospholipid. In some embodiments, the reactive group is a maleimide group. Maleimide groups can be crosslinked to each other in the presence of dithiol crosslinkers including but not limited to dithiolthrietol (DTT).

It is to be understood that the use of other functionalized lipids, other reactive groups, and other crosslinkers beyond those described above is further contemplated. In addition to the maleimide groups, other examples of contemplated reactive groups include but are not limited to other thiol reactive groups, amino groups such as primary and secondary amines, carboxyl groups, hydroxyl groups, aldehyde groups, alkyne groups, azide groups, carbonyls, halo acetyl (e.g., iodoacetyl) groups, imidoester groups, N-hydroxysuccinimide esters, sulfhydryl groups, and pyridyl disulfide groups.

Functionalized and non-functionalized lipids are available from a number of commercial sources including Avanti Polar 5 Lipids (Alabaster, Alabama).

In some embodiments, the provided liposomes further comprise an immunostimulatory agent, a detectable marker, or both disposed on its exterior. The immunostimulatory agent or detectable marker can be ionically bonded or covalently bonded to an exterior of the liposome, including, for example, optionally to a steric stabilizer component of the liposome.

The terms immunostimulatory agents, also known as immunostimulants, and immunostimulators, refer to substances that stimulate the immune system by inducing activation or increasing activity of any of its components. These immunostimulatory agents can include one or more of a hapten, an adjuvant, a protein immunostimulating agent, a nucleic acid immunostimulating agent, and a chemical immunostimulating agent. Many adjuvants contain a substance designed to stimulate immune responses, such as lipid A, Bortadella pertussis or *Mycobacterium tuberculosis* derived proteins. Certain adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, can also be used as adjuvants. In a preferred embodiment, the immunostimulant can be at least one selected from the group consisting of fluorescein, DNP, beta glucan, beta-1,3-glucan, beta-1,6-glucan.

A detectable marker may, for example, include, at least, a radioisotope, a fluorescent compound, a bioluminescent compound, chemiluminescent compound, a metal chelator, an enzyme, a dye, an ink, a magnetic compound, a biocatalyst or a pigment that is detectable by any suitable means known in the art, e.g., magnetic resonance imaging (MRI), optical imaging, fluorescent/luminescent imaging, or nuclear imaging techniques.

In some embodiments, the immunostimulatory agent and/or detectable marker is attached to the exterior by co-incubating it with the liposome. For example, the immunostimulatory agent and/or detectable marker may be associated with the liposomal membrane by hydrophobic interactions or by an ionic bond such as an avidin/biotin bond or a metal chelation bond (e.g., Ni-NTA). Alternatively, the immunostimulatory agent or detectable marker may be covalently bonded to the exterior of the liposome such as, for example, by being covalently bonded to a liposomal component or to the steric stabilizer which is the PEG.

One example reagent is fluorescein isothiocyanate (FITC) which, based on our experiments, surprisingly serves as both an immunostimulant and a detectable marker.

In further non-limiting embodiments, the provided liposomes enclose an interior space. In some embodiments, the interior space comprises, but is not limited to, an aqueous solution. In some embodiments, the interior space comprises a comprises an alpha or D-gamma polyglutamated antifolate as provided herein. In some embodiments, the interior space further comprises a pharmaceutically acceptable carrier such as trehalose. In an additional embodiment, the trehalose is present at about 5% to 20% weight percent of trehalose or any combination of one or more lyoprotectants or cryoprotectants at a total concentration of 5% to 20%. In some embodiments, the interior space comprises buffer. In further embodiments, the buffer is HEPES buffer or citrate buffer. In yet further embodiments, the citrate buffer is at a concentration of between 5 to 200 mM. In some embodiments, the interior space has a pH of between 2.8 to 6. In additional embodiments, the interior space of the liposome comprises sodium acetate and/or calcium acetate. In some embodiments, the interior space of the liposome comprises a total concentration of sodium acetate and calcium acetate of between 50 mM to 500 mM.

In some embodiments, the targeted pegylated liposomal polyglutamated (e.g., pentaglutamated or hexaglutamated) antifolate comprises a medium comprising a liposome including an interior space; an aqueous alpha (L-alpha or D-alpha) or D-gamma polyglutamated antifolate disposed within the interior space; and a targeting moiety comprising a protein with specific affinity for at least one folate receptor, and wherein the targeting moiety disposed at the exterior of the liposome. In some embodiments, the medium is an aqueous solution. In some embodiments, the interior space, the exterior space (e.g., the medium), or both the interior space and the medium contains one or more lyoprotectants or cryoprotectants which are listed above. In some embodiments, the cryoprotectant is mannitol, trehalose, sorbitol, or sucrose.

As discussed above, the liposomes may comprise a steric stabilizer that can increase their longevity in circulation. For those embodiments, which incorporate a steric stabilizer, the steric stabilizer may be at least one member selected from the group consisting of polyethylene glycol (PEG), poly-L-lysine (PLL), monosialoganglioside (GM1), poly(vinyl pyrolidone) (PVP), poly(acrylamide) (PAA), poly(2-methyl-2-oxazoline), poly(2-ethyl-2-oxazoline), phosphatidyl polyglycerol, poly[N-(2-hydroxypropyl) methacrylamide], amphiphilic poly-N-vinylpyrrolidones, L-amino-acid-based polymer, and polyvinyl alcohol. In some embodiments, the steric stabilizer or the population of steric stabilizer is PEG. In one embodiment, the steric stabilizer is a PEG. In a further embodiment, the PEG has a number average molecular weight (Mn) of 200 to 5000 daltons. These PEG(s) can be of any structure such as linear, branched, star or comb structure and are commercially available.

In some embodiments, the liposomal alpha (L-alpha or D-alpha) or D-gamma polyglutamated antifolate (LPA or PLPA) is water soluble. That is, the liposomal polyglutamated (e.g., pentaglutamated or hexaglutamated) antifolate is in the form of an aqueous solution. In some embodiments, the LPA or PLPA comprises an interior space that contains less than 200,000 molecules of the alpha (L-alpha or D-alpha) or D-gamma polyglutamated antifolate. In some embodiments, the LPA or PLPA contains between 10,000 to 100,000 molecules of the alpha (L-alpha or D-alpha) or D-gamma polyglutamated antifolate. In further embodiments, the LPA or PLPA contains between 10,000 to 100,000 molecules of the alpha (L-alpha or D-alpha) or D-gamma pentaglutamated antifolate. In further embodiments, the LPA or PLPA contains between 10,000 to 100,000 molecules of the alpha (L-alpha or D-alpha) or D-gamma hexaglutamated antifolate.

In some embodiments, the interior space of the LPA or PLPA contains less than 200,000 molecules of an alpha (L-alpha or D-alpha) or D-gamma polyglutamated antifolate selected from the group consisting of: polyglutamated MTX, polyglutamated PMX, polyglutamated LTX, polyglutamated AG2034, polyglutamated RTX, polyglutamated piritrexim, polyglutamated pralatrexate, polyglutamated AG2034, polyglutamated GW1843, polyglutamated aminopterin, and polyglutamated LY309887. In some embodiments, the liposome contains less than 200,000 molecules of alpha (L-alpha or D-alpha) or D-gamma polyglutamated PMX. In some embodiments, the liposome contains less than 200,000 molecules of alpha (L-alpha or D-alpha) or D-gamma polyglutamated MTX. In some embodiments, the liposome contains less than 200,000 molecules of alpha (L-alpha or D-alpha) or D-gamma polyglutamated RTX. In some embodiments, the liposome contains less than 200,000 molecules of molecules of alpha (L-alpha or D-alpha) or D-gamma pentaglutamated LTX. In some embodiments, the liposome contains less than 200,000 molecules of molecules of alpha (L-alpha or D-alpha) or D-gamma hexaglutamated LTX.

In some embodiments, the interior space of the LPA or PLPA contains between 10,000 to 100,000 molecules of an alpha (L-alpha or D-alpha) or D-gamma polyglutamated antifolate selected from the group consisting of: polyglutamated MTX, polyglutamated PMX, polyglutamated LTX, polyglutamated AG2034, polyglutamated RTX, polyglutamated piritrexim, polyglutamated pralatrexate, polyglutamated AG2034, polyglutamated GW1843, polyglutamated aminopterin, and polyglutamated LY309887. In some embodiments, the liposome contains between 10,000 to 100,000 molecules of alpha (L-alpha or D-alpha) or D-gamma polyglutamated PMX. In some embodiments, the liposome contains between 10,000 to 100,000 molecules of alpha (L-alpha or D-alpha) or D-gamma polyglutamated MTX. In some embodiments, the liposome contains between 10,000 to 100,000 molecules of alpha (L-alpha or D-alpha) or D-gamma polyglutamated RTX. In some embodiments, the liposome contains between 10,000 to 100,000 molecules of alpha (L-alpha or D-alpha) or D-gamma pentaglutamated LTX. In some embodiments, the liposome contains between 10,000 to 100,000 molecules of alpha (L-alpha or D-alpha) or D-gamma hexaglutamated LTX.

In some embodiments, the interior space of the LPA or PLPA contains less than 200,000 molecules of an alpha (L-alpha or D-alpha) or D-gamma pentaglutamated antifolate selected from the group consisting of pentaglutamated MTX, pentaglutamated PMX, pentaglutamated LTX, pentaglutamated AG2034, pentaglutamated RTX, pentaglutamated piritrexim, pentaglutamated pralatrexate, pentaglutamated AG2034, pentaglutamated GW1843, pentaglutamated aminopterin, and pentaglutamated LY309887. In some embodiments, the liposome contains less than 200,000 molecules of an alpha (L-alpha or D-alpha) or D-gamma pentaglutamated PMX. In some embodiments, the liposome contains less than 200,000 molecules of an alpha (L-alpha or D-alpha) or D-gamma pentaglutamated MTX. In some embodiments, the liposome contains less than 200,000 molecules of an alpha (L-alpha or D-alpha) or D-gamma pentaglutamated RTX. In some embodiments, the liposome contains less than 200,000 molecules of an alpha (L-alpha or D-alpha) or D-gamma pentaglutamated RTX.

In some embodiments, the interior space of the LPA or PLPA contains less than 200,000 molecules of an alpha (L-alpha or D-alpha) or D-gamma hexaglutamated antifolate selected from the group consisting of hexaglutamated MTX, hexaglutamated PMX, hexaglutamated LTX, hexaglutamated AG2034, hexaglutamated RTX, hexaglutamated piritrexim, hexaglutamated pralatrexate, hexaglutamated AG2034, hexaglutamated GW1843, hexaglutamated aminopterin, and hexaglutamated LY309887. In some embodiments, the liposome contains less than 200,000 molecules of an alpha (L-alpha or D-alpha) or D-gamma hexaglutamated PMX. In some embodiments, the liposome contains less than 200,000 molecules of an alpha (L-alpha or D-alpha) or D-gamma hexaglutamated MTX. In some embodiments, the liposome contains less than 200,000 molecules of an alpha (L-alpha or D-alpha) or D-gamma hexaglutamated RTX. In some embodiments, the liposome contains less than 200,000 molecules of an alpha (L-alpha or D-alpha) or D-gamma hexaglutamated RTX.

In some embodiments, the liposomal antifolate is pegylated (i.e., a pegylated liposomal alpha (L-alpha or D-alpha) or D-gamma polyglutamated (e.g., pentaglutamated or hexagluatamated) antifolate (PLPA or PLPA)). In some embodiments, the PLPA or PLPA is water soluble. That is, the PLPA or PLPA is in the form an aqueous solution. In some embodiments, the PLPA or PLPA comprises an interior space that contains less than 200,000 molecules of alpha (L-alpha or D-alpha) or D-gamma polyglutamated antifolate. In some embodiments, the PLPA or PLPA contains between 10,000 to 100,000 molecules of alpha (L-alpha or D-alpha) or D-gamma polyglutamated antifolate. In further embodiments, the PLPA or PLPA contains between 10,000 to 100,000 molecules of alpha (L-alpha or D-alpha) or D-gamma pentaglutamated antifolate. In some embodiments, the PLPA or PLPA contains between 10,000 to 100,000 molecules of alpha (L-alpha or D-alpha) or D-gamma polyglutamated antifolate. In further embodiments, the PLPA or PLPA contains between 10,000 to 100,000 molecules of alpha (L-alpha or D-alpha) or D-gamma hexaglutamated antifolate.

In some embodiments, the interior space of the PLPA or PLPA contains less than 200,000 molecules of alpha (L-alpha or D-alpha) or D-gamma polyglutamated antifolate selected from the group consisting of: polyglutamated MTX, polyglutamated PMX, polyglutamated LTX, polyglutamated AG2034, polyglutamated RTX, polyglutamated piritrexim, polyglutamated pralatrexate, polyglutamated AG2034, polyglutamated GW1843, polyglutamated aminopterin, and polyglutamated LY309887. In some embodiments, the liposome contains less than 200,000 molecules of alpha or D-gamma polyglutamated PMX. In some embodiments, the PLPA or PLPA contains less than 200,000 molecules of alpha or D-gamma polyglutamated MTX. In some embodiments, the PLPA or PLPA contains less than 200,000 molecules of alpha or D-gamma polyglutamated RTX. In some embodiments, the PLPA or PLPA contains less than 200,000 molecules of alpha or D-gamma pentaglutamated LTX. In some embodiments, the PLPA or PLPA contains less than 200,000 molecules of alpha or D-gamma hexaglutamated LTX.

In some embodiments, the interior space of the PLPA or PLPA contains between 10,000 to 100,000 molecules of alpha (L-alpha or D-alpha) or D-gamma polyglutamated antifolate selected from the group consisting of: polyglutamated MTX, polyglutamated PMX, polyglutamated LTX, polyglutamated AG2034, polyglutamated RTX, polyglutamated piritrexim, polyglutamated pralatrexate, polyglutamated AG2034, polyglutamated GW1843, polyglutamated aminopterin, and polyglutamated LY309887. In some embodiments, the liposome contains between 10,000 to 100,000 molecules of alpha (L-alpha or D-alpha) or D-gamma polyglutamated PMX. In some embodiments, the PLPA or PLPA contains between 10,000 to 100,000 molecules of alpha or D-gamma polyglutamated MTX. In some embodiments, the PLPA or PLPA contains between 10,000 to 100,000 molecules of alpha or D-gamma polyglutamated RTX. In some embodiments, the PLPA or PLPA contains between 10,000 to 100,000 molecules of alpha (L-alpha or D-alpha) or D-gamma pentaglutamated LTX. In some embodiments, the PLPA or PLPA contains between 10,000 to 100,000 molecules of alpha (L-alpha or D-alpha) or D-gamma hexaglutamated LTX.

In further embodiments, the interior space of the PLPA or PLPA contains less than 200,000 molecules of alpha (L-alpha or D-alpha) or D-gamma pentaglutamated antifolate selected from the group consisting of pentaglutamated MTX, pentaglutamated PMX, pentaglutamated LTX, pentaglutamated AG2034, pentaglutamated RTX, pentaglutamated piritrexim, pentaglutamated pralatrexate, pentaglutamated AG2034, pentaglutamated GW1843, pentaglutamated aminopterin, and pentaglutamated LY309887. In some embodiments, the PLPA or PLPA contains less than 200,000 molecules of pentaglutamated PMX. In some embodiments, the PLPA or PLPA contains less than 200,000 molecules of alpha (L-alpha or D-alpha) or D-gamma pentaglutamated MTX. In some embodiments, the PLPA or PLPA contains less than 200,000 molecules of alpha (L-alpha or D-alpha) or D-gamma pentaglutamated RTX. In some embodiments, the PLPA or PLPA contains less than 200,000 molecules of alpha (L-alpha or D-alpha) or D-gamma pentaglutamated RTX.

In further embodiments, the interior space of the PLPA or PLPA contains less than 200,000 molecules of alpha (L-alpha or D-alpha) or D-gamma hexaglutamated antifolate selected from the group consisting of hexaglutamated MTX, hexaglutamated PMX, hexaglutamated LTX, hexaglutamated AG2034, hexaglutamated RTX, hexaglutamated piritrexim, hexaglutamated pralatrexate, hexaglutamated AG2034, hexaglutamated GW1843, hexaglutamated aminopterin, and hexaglutamated LY309887. In some embodiments, the PLPA or PLPA contains less than 200,000 molecules of hexaglutamated PMX. In some embodiments, the PLPA or PLPA contains less than 200,000 molecules of alpha (L-alpha or D-alpha) or D-gamma hexaglutamated MTX. In some embodiments, the PLPA or PLPA contains less than 200,000 molecules of alpha (L-alpha or D-alpha) or D-gamma hexaglutamated RTX. In some embodiments, the PLPA or PLPA contains less than 200,000 molecules of alpha (L-alpha or D-alpha) or D-gamma hexaglutamated RTX.

In further embodiments, the interior space of the PLPA or PLPA contains between 10,000 to 100,000 molecules of alpha (L-alpha or D-alpha) or D-gamma pentaglutamated antifolate selected from the group consisting of pentaglutamated MTX, pentaglutamated PMX, pentaglutamated LTX, pentaglutamated AG2034, pentaglutamated RTX, pentaglutamated piritrexim, pentaglutamated pralatrexate, pentaglutamated AG2034, pentaglutamated GW1843, pentaglutamated aminopterin, and pentaglutamated LY309887. In some embodiments, the PLPA or PLPA contains between 10,000 to 100,000 molecules of alpha or D-gamma pentaglutamated PMX. In some embodiments, the PLPA or PLPA contains between 10,000 to 100,000 molecules of alpha or D-gamma pentaglutamated MTX. In some embodiments, the PLPA or PLPA contains between 10,000 to 100,000 molecules of pentaglutamated RTX. In some embodiments, the PLPA or PLPA contains between 10,000 to 100,000 molecules of alpha or D-gamma pentaglutamated RTX.

In further embodiments, the interior space of the PLPA or PLPA contains between 10,000 to 100,000 molecules of alpha (L-alpha or D-alpha) or D-gamma hexaglutamated antifolate selected from the group consisting of hexaglutamated MTX, hexaglutamated PMX, hexaglutamated LTX, hexaglutamated AG2034, hexaglutamated RTX, hexaglutamated piritrexim, hexaglutamated pralatrexate, hexaglutamated AG2034, hexaglutamated GW1843, hexaglutamated aminopterin, and hexaglutamated LY309887. In some embodiments, the PLPA or PLPA contains between 10,000 to 100,000 molecules of alpha or D-gamma hexaglutamated PMX. In some embodiments, the PLPA or PLPA contains between 10,000 to 100,000 molecules of alpha or D-gamma hexaglutamated MTX. In some embodiments, the PLPA or PLPA contains between 10,000 to 100,000 molecules of hexaglutamated RTX. In some embodiments, the PLPA or PLPA contains between 10,000 to 100,000 molecules of alpha or D-gamma hexaglutamated RTX.

In some embodiments, the pH of solutions comprising the liposome composition is from pH 5 to 8 or from pH 2 to 6.

Targeted Liposomes

In some embodiments, the disclosure provides a liposomal polyglutamated antifolate composition wherein the liposome is pegylated and comprises an alpha (L-alpha or D-alpha) or D-gamma polyglutamated antifolate and targeting moiety attached to one or both of a PEG and the exterior of the liposome, and wherein the targeting moiety has a specific affinity for a surface antigen on a target cell of interest. Such liposomes may generally be referred to herein as "targeted liposomes," e.g., liposomes including one or more targeting moieties or biodistribution modifiers on the surface of, or otherwise attached to, the liposomes. The targeting moiety of the targeted liposomes can be any moiety or agent that is capable of specifically binding a desired target (e.g., an antigen target expressed on the surface of a target cell of interest). In one embodiment, the targeted liposome specifically and preferentially binds to a target on the surface of a target cell of interest that internalizes the targeted liposome into which the liposome encapsulated alpha or D-gamma polyglutamated cytotoxic agent (e.g., polyglutamated antifolates, such as pentaglutamated or hexaglutamated PMX, LTX, and MTX) exerts its cytotoxic effect. In further embodiments, the target cell is a cancer cell, a tumor cell or a metastatic cell. In some embodiments, the targeting liposomes are immunoliposomes.

The term attach or attached refers, for example, to any type of bonding such as covalent bonding, ionic bonding (e.g., avidin-biotin) bonding by hydrophobic interactions, and bonding via functional groups such as maleimide, or linkers such as PEG. For example, a detectable marker, a steric stabilizer, a liposome, a liposomal component, an immunostimulating agent may be attached to each other directly, by a maleimide functional group, or by a PEG-maleimide group.

In some embodiments, the targeting moiety attached to the liposome is a polypeptide. In further embodiments, the targeting moiety is an antibody or a fragment of an antibody. In additional embodiments, the targeting moiety comprises one or more of an antibody, a humanized antibody, an antigen binding fragment of an antibody, a single chain antibody, a single-domain antibody, a bi-specific antibody, a synthetic antibody, a pegylated antibody, and a multimeric antibody. In additional embodiments, the targeting moiety has the specific affinity for an epitope on a tumor cell surface antigen that is present on a tumor cell but absent or inaccessible on a non-tumor cell. In some embodiments, the targeting moiety further comprises one or more of an immunostimulatory agent, a detectable marker and a maleimide disposed on at least one of the PEG and the exterior of the liposome. In some embodiments, the targeting moiety of the liposomal alpha (L-alpha or D-alpha) or D-gamma polyglutamated antifolate (LPA) or a pegylated liposomal alpha (L-alpha or D-alpha) or D-gamma polyglutamated antifolate (PLPA) liposome is anionic or neutral. In other embodiments, the targeting moiety of the LPA or PLPA liposome is cationic. In some embodiments, the targeting moiety LPA or PLPA liposome composition comprises at least 10% liposome entrapped alpha (L-alpha or D-alpha) or D-gamma polyglutamated antifolate. In some embodiments, the targeting moiety-LPA or targeting moiety-PLPA liposomes have a diameter in the range of 20 nm to 200 nm. In further embodiments, the liposomes have a diameter in the range of 80 nm to 120 nm.

In some embodiments, the targeting moiety-LPA or targeting moiety-PLPA comprises a polypeptide targeting moiety such as an antibody or an antibody fragment and the targeting moiety binds a target antigen with an equilibrium dissociation constant (Kd) in a range of $0.5 \times 10^{-10}$ to $10 \times 10^{-6}$ as determined using BIACORE analysis. In further embodiments, the targeting moiety-LPA or targeting moiety-PLPA comprises a polypeptide targeting moiety.

In some embodiments, the targeting moiety-LPA or targeting moiety-PLPA comprises a polypeptide targeting moiety such as an antibody or an antibody fragment and the targeting moiety has a specific affinity for a target antigen selected from the group consisting of GONMB, CD56, TACSTD2 (TROP2), CEACAM5, Folate receptor-α, Folate receptor-β, Folate receptor-δ, Mucin 1, STEAP1, Mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P-Cadherin, Fibronectin Extra-domain B (ED-B), VEGFR2 (CD309), Tenascin, Collagen IV, Periostin, endothelin receptor, HER 2, EGFR, CD30, CD79b, CD19, CD138, CD74, CD37, CD19, CD22, CD33, and CD98.

In further embodiments, the targeting moiety comprises a polypeptide targeting moiety such as an antibody or an antibody fragment and the targeting moiety has binding specificity for a folate receptor. In some embodiments the targeting moiety binds a folate receptor with an equilibrium dissociation constant (Kd) in a range of $0.5 \times 10-10$ to $10 \times 10$ 6 as determined using BIACORE analysis. In some embodiments the folate receptor bound by the targeting moiety is one or more folate receptors selected from the group consisting of: folate receptor alpha (FR-α), folate receptor beta (FR-β), and folate receptor delta (FR-δ).

In some embodiments, the targeting moiety is an antibody or antigen binding portion of an antibody that specifically binds a target of interest expressed on the surface of a targeted cell of interest. In some embodiments, the targeting moiety is a full-length antibody. In some embodiments, the targeting moiety is an antigen binding portion of an antibody. In some embodiments, the targeting moiety comprises one or more complementarity determining regions (CDRs) of antibody origin. Examples of suitable proteins that can serve as targeting moieties for the disclosed targeted liposomes include a full-length human antibody, a humanized antibody, a chimeric antibody, an antigen binding fragment of an antibody, a single chain antibody, a single-domain antibody, a bi-specific antibody, a synthetic antibody, a pegylated antibody and a multimeric antibody. The antibody of the provided targeted liposomes can have a combination of the above characteristics. For example, a humanized antibody can be an antigen binding fragment and can be pegylated and multimerized as well.

The term "humanized antibody" refers to forms of non-human (e.g., murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g. mouse, rat, rabbit, and hamster) that have the desired specificity, affinity, and capability (Jones et al., Nature 321:522-525 (1986); Riechmann et al., Nature 332:323-327 (1988); Verhoeyen et al., Science 239:1534-1536 (1988)). In some instances, the Fv framework region (FR) residues of a human immunoglobulin are replaced with the corresponding residues in an antibody from a non-human species that has the desired specificity, affinity, and capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. Nos. 5,225,539 and 5,639,641.

A discussed herein, folate receptors (FRs) are distinct from reduced folate carriers (RFCs) and exploit different pathways for bringing folates and antifolates into cells. In some embodiments, the targeting moiety specifically binds a folate receptor. In further embodiments, the targeting moiety specifically binds a folate receptor selected from folate receptor alpha, folate receptor beta and folate receptor delta. Antibodies to folate receptor alpha can routinely be generated using techniques known in the art. Moreover, the sequences of numerous anti-folate receptor antibodies are in the public domain and/or commercially available and are readily obtainable.

Murine antibodies against folate receptor are examples of antibodies that can be used as targeting moieties of the disclosed targeted liposome is a murine antibody against folate receptor. The sequence of these antibodies are known and are described, for example, in U.S. Pat. Nos. 5,646,253; 8,388,972; 8,871,206; and 9,133,275 and in Intl. Appl. Nos. PCT/US2011/056966 and PCT/US2012/046672. For example, based on the sequences disclosed already in the public domain, the gene for the antibodies can be synthesized and placed into a transient expression vector and the antibody was produced in HEK-293 transient expression system. The antibody can be a complete antibody, a Fab, or any of the various antibody variations discussed herein or otherwise known in the art.

In some embodiments, the targeted liposomes comprise from 30 to 500 targeting moieties (e.g., 30 to 250 targeting moieties or 30-200 targeting moieties). In some embodiments, the provided targeted liposomes contain less than 220 targeting moieties, less than 200 targeting moieties, or less than targeting 175 moieties. In some embodiments, the targeting moiety is non-covalently bonded to the outside of the liposome (e.g., via ionic interaction or a GPI anchor).

In some embodiments, the molecules on the outside of the targeted liposome include a lipid, a targeting moiety, a steric stabilizer (e.g., a PEG), a maleimide, and a cholesterol. In some embodiments, the targeting moiety is covalently bound via a maleimide functional group. In some embodiments, the targeting moiety is covalently bound to a liposomal component or a steric stabilizer such as a PEG molecule. In some embodiments, all the targeting moieties are bound to one component of the liposome such as a PEG. In other embodiments, the targeting moieties are bound to different components of the liposome. For example, some targeting moieties may be bound to the lipid components or cholesterol, some targeting moieties may be bound to the steric stabilizer (e.g., PEG) and still other targeting moieties may be bound to a detectable marker or to another targeting moiety.

In some embodiments, the targeting moiety of the targeted liposome has affinity and specificity (i.e., specifically binds) for an antigen expressed on the surface of a cancer cell. In further some embodiments, the targeting moiety of the targeted liposome has affinity and specificity for one or more antigens selected from the group consisting of folate receptor alpha, folate receptor beta, and folate receptor delta. In one embodiment, the targeting moiety has specific affinity (i.e., specifically binds) an antigen selected from the group consisting of folate receptor alpha, folate receptor beta, and folate receptor delta. In a further embodiment, the targeting moiety has specific affinity for at least two antigens selected from the group consisting of folate receptor alpha, folate receptor beta, and folate receptor delta. In another embodiment, the targeting moiety has specific affinity for three antigens which are, for example, folate receptor alpha; folate receptor beta; and folate receptor delta. The targeting moiety may have affinity and specificity to an epitope of the antigen because sometimes a targeting moiety does not bind the complete antigen but just an epitope of many epitopes in an antigen.

The term "epitope" or "antigenic determinant" are used interchangeably herein and refer to that portion of an antigen capable of being recognized and specifically bound by a particular antibody or binding moiety. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

In some embodiments, the targeting moiety has specific affinity for an epitope on a tumor cell surface antigen that is present on a tumor cell but absent or inaccessible on a non-tumor cell. For example, in some situations, the tumor antigen is on the surface of both normal cells and malignant cancer cells but the tumor epitope is only exposed in a cancer cell. As a further example, a tumor antigen may experience a confirmation change in cancer causing cancer cell specific epitopes to be present. A targeting moiety with specific affinity to epitopes described herein are useful and are encompassed by the disclosed compositions and methods. In some embodiments, the tumor cell with the cancer cell specific epitope(s) is a cancer cell. Examples of such tumor cell surface antigens include, folate receptor alpha, folate receptor beta and folate receptor delta.

In some embodiments, the liposome composition is provided as a pharmaceutical composition containing the liposome and a carrier, e.g., a pharmaceutically acceptable carrier. Examples of pharmaceutically acceptable carriers contained in the provided pharmaceutical compositions include normal saline, isotonic dextrose, isotonic sucrose, Ringer's solution, and Hanks' solution. In some embodiments, a buffer substance is added to maintain an optimal pH for storage stability of the pharmaceutical composition. In some embodiments, the pH of the pharmaceutical composition is between 6.0 and 7.5. In some embodiments, the pH is between 6.3 and 7.0. In further embodiments, the pH is 6.5. Ideally the pH of the pharmaceutical composition allows for both stability of liposome membrane lipids and retention of the entrapped entities. Histidine, hydroxyethylpiperazine-ethylsulfonate (HEPES), morpholipoethylsulfonate (MES), succinate, tartrate, and citrate, typically at 2-20 mM concentration, are exemplary buffer substances. Other suitable carriers include, e.g., water, buffered aqueous solution, 0.4% NaCl, and 0.3% glycine. Protein, carbohydrate, or polymeric stabilizers and tonicity adjusters can be added, e.g., gelatin, albumin, dextran, or polyvinylpyrrolidone. The tonicity of the composition can be adjusted to the physiological level of 0.25-0.35 mol/kg with glucose or a more inert compound such as lactose, sucrose, mannitol, or dextrin. These compositions can routinely be sterilized using conventional, sterilization techniques known in the art (e.g., by filtration). The resulting aqueous solutions can be packaged for use or filtered under aseptic conditions and lyophilized, the lyophilized preparation being combined with a sterile aqueous medium prior to administration.

The provided pharmaceutical liposome compositions can also contain other pharmaceutically acceptable auxiliary substances as required to approximate physiological conditions, such as pH adjusting and buffering agents, and tonicity adjusting agents, for example, sodium acetate, sodium lactate, sodium chloride, potassium chloride, and calcium chloride. Additionally, the liposome suspension may include lipid-protective agents which protect lipids against free-radical and lipid-peroxidative damages on storage. Lipophilic free-radical quenchers, such as alpha-tocopherol and water-soluble iron-specific chelators, such as ferrioxamine, are suitable.

The liposome concentration in the provided fluid pharmaceutical formulations can vary widely depending upon need, e.g., from less than about 0.05% usually or at least about 2-10% to as much as 30 to 50% by weight and will be selected primarily by fluid volumes, and viscosities, in accordance with the particular mode of administration selected. For example, the concentration may be increased to lower the fluid load associated with treatment. This may be particularly desirable in patients having atherosclerosis-associated congestive heart failure or severe hypertension. Alternatively, liposome pharmaceutical compositions composed of irritating lipids may be diluted to low concentrations to lessen inflammation at the site of administration.

Some embodiments, relate to a method of delivering a targeted pegylated liposomal formulation of a alpha (L-alpha or D-alpha) or D-gamma polyglutamated antifolate, to a tumor expressing folate receptor on its surface. An exemplary method comprises the step of administering at least one of any of the compositions comprising a liposome in this disclosure in an amount to deliver a therapeutically effective dose of the targeted pegylated liposomal alpha (L-alpha or D-alpha) or D-gamma polyglutamated antifolate to the tumor.

The amount of liposome pharmaceutical composition administered will depend upon the particular polyglutamated antifolate therapeutic entity entrapped inside the liposomes, the disease state being treated, the type of liposomes being used, and the judgment of the clinician. Generally the amount of liposome pharmaceutical composition administered will be sufficient to deliver a therapeutically effective dose of the particular therapeutic entity.

The quantity of liposome pharmaceutical composition necessary to deliver a therapeutically effective dose can be determined by routine in vitro and in vivo methods, common in the art of drug testing. See, for example, D. B. Budman, A. H. Calvert, E. K. Rowinsky (editors). Handbook of Anticancer Drug Development, L W W, 2003. Therapeutically effective dosages for various therapeutic compositions are known to those skilled in the art. In some embodiments, a therapeutic entity delivered via the pharmaceutical liposome composition and provides at least the same or higher activity than the activity obtained by administering the same amount of the therapeutic entity in its routine non-liposome formulation. Typically the dosages for the liposome pharmaceutical composition is in a range for example, between about 0.005 and about 500 mg of the therapeutic entity per kilogram of body weight, most often, between about 0.1 and about 100 mg therapeutic entity/kg of body weight.

As used herein an "effective amount" refers to a dosage of an agent sufficient to provide a medically desirable result. The effective amount will vary with the desired outcome, the particular condition being treated or prevented, the age and physical condition of the subject being treated, the severity of the condition, the duration of the treatment, the nature of the concurrent or combination therapy (if any), the specific route of administration and like factors within the knowledge and expertise of the health practitioner. An "effective amount" can be determined empirically and in a routine manner, in relation to the stated purpose. In this disclosure, the term "subject" and "patient" is used interchangeably and has the same meaning. It is preferred generally that a maximum dose be used, that is, the highest safe dose according to sound medical judgment.

For example, if the subject has a tumor, an effective amount may be that amount of the agent (e.g., alpha (L-alpha or D-alpha) or D-gamma polyglutamated antifolate) that reduces the tumor volume or load (as for example determined by imaging the tumor). Effective amounts can also routinely be assessed by the presence and/or frequency of cancer cells in the blood or other body fluid or tissue (e.g., a biopsy). If the tumor is impacting the normal functioning of a tissue or organ, then the effective amount can routinely be assessed by measuring the normal functioning of the tissue or organ. In some instances the effective amount is the amount required to lessen or eliminate one or more, and preferably all, symptoms.

Terms such as "treating," or "treatment," or "to treat" refer to both (a) therapeutic measures that cure, slow down, lessen symptoms of, and/or halt progression of a diagnosed pathologic condition or disorder and (b) prophylactic or preventative measures that prevent and/or slow the development of a targeted disease or condition. Thus, subjects in need of treatment include those already with the cancer or condition; those at risk of having the cancer or condition; and those in whom the infection or condition is to be prevented. In certain embodiments, a subject is successfully "treated" according to the methods provided herein if the subject shows, e.g., total, partial, or transient amelioration or elimination of a symptom associated with the disease or condition (e.g., cancer, rheumatoid arthritis).

Pharmaceutical compositions comprising the provided alpha (L-alpha or D-alpha) or D-gamma polyglutamated antifolate compositions (e.g., liposomes containing a pentaglutamated or hexaglutamated antifolate) are also provided. Pharmaceutical compositions are sterile compositions that comprise a sample liposome and preferably antifolate(s), preferably in a pharmaceutically-acceptable carrier.

The term "delivery vehicle" refers generally to any compositions that acts to assist, promote or facilitate entry of polyglutamated antifolates into a cell, for example, viral sequences, viral material, or lipid or liposome formulations.

The term "pharmaceutically-acceptable carrier" refers to for example, one or more compatible solid or liquid filler, diluents or encapsulating substances which are suitable for administration to a human or other subject.

The term "carrier" denotes an organic or inorganic ingredient, natural or synthetic, with which liposome compositions are combined to facilitate administration. The components of the pharmaceutical compositions are comingled in a manner that precludes interaction that would substantially impair their desired pharmaceutical efficiency. Suitable buffering agents include acetic acid and a salt (1-2% W/V); citric acid and a salt (1-3% W/V); boric acid and a salt (0.5-2.5% W/V); and phosphoric acid and a salt (0.8-2% W/V). Suitable preservatives include benzalkonium chloride (0.003-0.03% W/V); chlorobutanol (0.3-0.9% W/V); and parabens (0.01-0.25% W/V).

Unless otherwise stated herein, a variety of administration routes are available. The particular mode selected will depend, upon the particular active agent selected, the particular condition being treated and the dosage required for therapeutic efficacy. The provided methods can be practiced using any known mode of administration that is medically acceptable and in accordance with good medical practice. In some embodiments, the administration route is an injection. In further embodiments, the injection is by a parenteral route elected from an intramuscular, subcutaneous, intravenous, intraarterial, intraperitoneal, intraarticular, intraepidural, intrathecal, intravenous, intramuscular, or intra sternal injection. In some embodiments, the administration route is an infusion. In additional embodiments, the administration route is oral, nasal, mucosal, sublingual, intratracheal, ophthalmic, rectal, vaginal, ocular, topical, transdermal, pulmonary, or inhalation.

In some embodiment, PLPAs and/or targeted-PLPA is prepared as an infusion composition, an injection composition, a parenteral composition, or a topical composition. In further embodiments, the injection includes one or more of: intraperitoneal injection, direct intratumor injection, intra-arterial injection, intravenous injection, subcutaneous injection, intramuscular injection, delivery via transcutaneous and intranasal route. In a further embodiment, the PLPA and/or targeted-PLPA is a liquid solution or a suspension. However, solid forms suitable for solution in, or suspension in, liquid vehicles prior to injection are also provided herein. In some embodiments, the targeted pegylated liposomal alpha (L-alpha or D-alpha) or D-gamma polyglutamated antifolate is formulated as an enteric-coated tablet or gel capsule according to methods known in the art.

In some embodiments, the targeted pegylated liposomal alpha (L-alpha or D-alpha) or D-gamma polyglutamated antifolate foimulations are administered to a tumor of the central nervous system using a slow, sustained intracranial infusion of the liposomes directly into the tumor (e.g., a convection-enhanced delivery (CED)). See, Saito et al., Cancer Research 64:2572-2579 (2004); Mamot et al., J. Neuro-Oncology 68:1-9 (2004). In other embodiments, the formulations are directly applied to tissue surfaces. Sustained release, pH dependent release, and other specific chemical or environmental condition-mediated release administration of the pegylated liposomal an alpha (L-alpha or D-alpha) or D-gamma polyglutamated antifolates (e.g., depot injections and erodible implants) are also provided. Examples of such release-mediating compositions are further described herein or otherwise known in the art.

For administration by inhalation, the compositions can be conveniently delivered in the form of an aerosol spray presentation from pressurized packs or a nebulizer, with the use of a suitable propellant, e.g., dichlorodifluoromethane, trichlorofluoromethane, ichlorotetrafluoroethane, carbon dioxide or other suitable gas. In the case of a pressurized aerosol, the dosage unit can be determined by providing a valve to deliver a metered amount.

When it is desirable to deliver the compositions systemically, they can formulated for parenteral administration by injection, e.g., by bolus injection or continuous infusion. Formulations for injection can be presented in unit dosage form, e.g., in ampoules or in multi-dose containers. Pharmaceutical parenteral formulations include aqueous solutions of the ingredients. Aqueous injection suspensions can contain substances which increase the viscosity of the suspension, such as sodium carboxymethyl cellulose, sorbitol, or dextran. Alternatively, suspensions of liposomes can be prepared as oil-based suspensions. Suitable lipophilic solvents or vehicles include fatty oils such as sesame oil, or synthetic fatty acid esters, such as ethyl oleate or triglycerides.

Alternatively, the non-targeted or targeted pegylated liposomal alpha (L-alpha or D-alpha) or D-gamma polyglutamated antifolates can be in powder form or lyophilized form for constitution with a suitable vehicle, e.g., sterile pyrogen-free water, before use.

The provided compositions (e.g., alpha (L-alpha or D-alpha) or D-gamma polyglutamated antifolates and liposomes containing the alpha (L-alpha or D-alpha) or D-gamma polyglutamated antifolates) can also be formulated in rectal or vaginal compositions such as suppositories or retention enemas, e.g., containing conventional suppository bases such as cocoa butter or other glycerides.

The provided compositions have applications, in vivo, ex vivo and in vitro. In some embodiments, the compositions have in vitro applications. In vitro use may include uses such as cell culturing and tissue engineering where selective treatment of a subpopulation of cells is desired. For example, during the culture of stem cells from a normal patient or a patient suffering from cancer, the cells can be treated with a sample composition or sample liposome as discussed to address cancerous subpopulations of cells. The cancerous subpopulation may arise because the donor originally has cancer or because the cells spontaneously transform during in vitro procedures.

In some embodiments, the liposome compositions are provided in a kit comprising a container with the liposomes, and optionally, a container with the entity (antigen) targeted or preferentially bound by liposomes, and an instruction, e.g., procedures or information related to using the liposome composition in one or more applications. Such instruction can be provided via any medium, e.g., hard paper copy, electronic medium, or access to a database or website containing the instruction.

In some embodiments, the disclosure provides a method of killing a hyperproliferative cell that comprises contacting a hyperproliferative cell with a delivery vehicle (e.g., liposome) comprising alpha (L-alpha or D-alpha) or D-gamma polyglutamated (e.g., pentaglutamated or hexaglutamated) antifolate. In some embodiments, the delivery vehicle is a liposome that comprises alpha polyglutamated antifolate. In some embodiments, the delivery vehicle is a liposome that comprises L-alpha polyglutamated antifolate. In some embodiments, the delivery vehicle is a liposome that comprises D-alpha polyglutamated antifolate. In some embodiments, the delivery vehicle is a liposome that comprises D-gamma polyglutamated antifolate. In some embodiments, the alpha or D-gamma polyglutamated antifolate is a member selected from the group consisting of: polyglutamated methotrexate (MTX), polyglutamated pemetrexed (PMX), polyglutamated lometrexol (LTX), polyglutamated AG2034, polyglutamated raltitrexed (RTX), polyglutamated piritrexim, polyglutamated pralatrexate, polyglutamated AG2034, polyglutamated GW1843, polyglutamated aminopterin, and polyglutamated LY309887. In some embodiments, the alpha or D-gamma polyglutamated antifolate comprises a pentaglutamated antifolate selected from the group consisting of pentaglutamated MTX, pentaglutamated PMX, pentaglutamated LTX, pentaglutamated AG2034, pentaglutamated RTX, pentaglutamated piritrexim, pentaglutamated pralatrexate, pentaglutamated AG2034, pentaglutamated GW1843, pentaglutamated aminopterin, and pentaglutamated LY309887. In some embodiments, the alpha or D-gamma polyglutamated antifolate comprises pentaglutamated PMX. In some embodiments, the alpha or D-gamma polyglutamated antifolate comprises pentaglutamated MTX. In some embodiments, the alpha or D-gamma polyglutamated antifolate comprises pentaglutamated RTX. In some embodiments, the alpha or D-gamma polyglutamated antifolate comprises pentaglutamated LTX. In some embodiments, the alpha or D-gamma polyglutamated antifolate comprises a hexaglutamated antifolate selected from the group consisting of hexaglutamated MTX, hexaglutamated PMX, hexaglutamated LTX, hexaglutamated AG2034, hexaglutamated RTX, hexaglutamated piritrexim, hexaglutamated pralatrexate, hexaglutamated AG2034, hexaglutamated GW1843, hexaglutamated aminopterin, and hexaglutamated LY309887. In some embodiments, the alpha or D-gamma polyglutamated antifolate comprises hexaglutamated PMX. In some embodiments, the alpha or D-gamma polyglutamated antifolate comprises hexaglutamated MTX. In some embodiments, the alpha or D-gamma polyglutamated antifolate comprises hexaglutamated RTX. In some embodiments, the alpha or D-gamma polyglutamated antifolate comprises hexaglutamated LTX. In some embodiments, the delivery vehicle is a liposome. In further embodiments, the liposome is pegylated. In additional embodiments, the delivery vehicle comprises a targeting moiety on its surface that specifically binds an antigen on the surface of the hyperproliferative cell. In further embodiments, the delivery vehicle comprises a targeting moiety that specifically binds a cell surface antigen on the surface of the hyperproliferative cell selected from the group consisting of GONMB, CD56, TACSTD2 (TROP2), CEACAM5, Folate receptor-α, Folate receptor-β, Folate receptor-δ, Mucin 1, STEAP1, Mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P-Cadherin, Fibronectin Extra-domain B (ED-B), VEGFR2 (CD309), Tenascin, Collagen IV, Periostin, endothelin receptor, HER 2, EGFR, CD30, CD79b, CD19, CD138, CD74, CD37, CD19, CD22, CD33, and CD98. In further embodiments, the delivery vehicle is a liposome, and the liposome comprises a targeting moiety that specifically binds comprises a targeting moiety that specifically binds a cell surface antigen on the surface of the hyperproliferative cell selected from the group consisting of GONMB, CD56, TACSTD2 (TROP2), CEACAM5, Folate receptor-α, Folate receptor-β, Folate receptor-δ, Mucin 1, STEAP1, Mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P-Cadherin, Fibronectin Extra-domain B (ED-B), VEGFR2 (CD309), Tenascin, Collagen IV, Periostin, endothelin receptor, HER 2, EGFR, CD30, CD79b, CD19, CD138, CD74, CD37, CD19, CD22, CD33, and CD98. In some embodiments, the disclosure provides a method of inhibiting the proliferation of a tumor cell that comprises contacting the tumor cell with a delivery vehicle (e.g., liposome) comprising a polyglutamated (e.g., pentaglutamated or hexaglutamated) antifolate. In some embodiments, the alpha (L-alpha or D-alpha) or D-gamma polyglutamated antifolate is a member selected from the group consisting of: polyglutamated methotrexate (MTX), polyglutamated pemetrexed (PMX), polyglutamated lometrexol (LTX), polyglutamated AG2034, polyglutamated raltitrexed (RTX), polyglutamated piritrexim, polyglutamated pralatrexate, polyglutamated AG2034, polyglutamated GW1843, polyglutamated aminopterin, and polyglutamated LY309887. In some embodiments, the alpha (L-alpha or D-alpha) or D-gamma polyglutamated antifolate comprises a pentaglutamated antifolate selected from the group consisting of pentaglutamated MTX, pentaglutamated PMX, pentaglutamated LTX, pentaglutamated AG2034, pentaglutamated RTX, pentaglutamated piritrexim, pentaglutamated pralatrexate, pentaglutamated AG2034, pentaglutamated GW1843, pentaglutamated aminopterin, and pentaglutamated LY309887. In some embodiments, the alpha (L-alpha or D-alpha) or D-gamma polyglutamated antifolate comprises pentaglutamated PMX. In some embodiments, the alpha (L-alpha or D-alpha) or D-gamma polyglutamated antifolate comprises pentaglutamated MTX. In some embodiments, the alpha (L-alpha or D-alpha) or D-gamma polyglutamated antifolate comprises pentaglutamated RTX. In some embodiments, the alpha (L-alpha or D-alpha) or D-gamma polyglutamated antifolate comprises pentaglutamated LTX. In some embodiments, the alpha (L-alpha or D-alpha) or D-gamma polyglutamated antifolate comprises a hexaglutamated antifolate selected from the group consisting of hexaglutamated MTX, hexaglutamated PMX, hexaglutamated LTX, hexaglutamated AG2034, hexaglutamated RTX, hexaglutamated piritrexim, hexaglutamated pralatrexate, hexaglutamated AG2034, hexaglutamated GW1843, hexaglutamated aminopterin, and hexaglutamated LY309887. In some embodiments, the alpha (L-alpha or D-alpha) or D-gamma polyglutamated antifolate comprises hexaglutamated PMX. In some embodiments, the alpha (L-alpha or D-alpha) or D-gamma polyglutamated antifolate comprises hexaglutamated MTX. In some embodiments, the alpha (L-alpha or D-alpha) or D-gamma polyglutamated antifolate comprises hexaglutamated RTX. In some embodiments, the alpha (L-alpha or D-alpha) or D-gamma polyglutamated antifolate comprises hexaglutamated LTX. In some embodiments, the delivery vehicle is a liposome. In further embodiments, the liposome is pegylated. In additional embodiments, the delivery vehicle comprises a targeting moiety on its surface that specifically binds an antigen on the surface of the hyperproliferative cell. In further embodiments, the delivery vehicle comprises a targeting moiety that specifically binds a cell surface antigen on the surface of the tumor cell selected from the group consisting of GONMB, CD56, TACSTD2 (TROP2), CEACAM5, Folate receptor-α, Folate receptor-β, Folate receptor-δ, Mucin 1, STEAP1, Mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P-Cadherin, Fibronectin Extra-domain B (ED-B), VEGFR2 (CD309), Tenascin, Collagen IV, Periostin, endothelin receptor, HER 2, EGFR, CD30, CD79b, CD19, CD138, CD74, CD37, CD19, CD22, CD33, and CD98. In further embodiments, the delivery vehicle is a liposome, and the liposome comprises a targeting moiety that specifically binds comprises a targeting moiety that specifically binds a cell surface antigen on the surface of the tumor cell selected from the group consisting of GONMB, CD56, TACSTD2 (TROP2), CEACAM5, Folate receptor-α, Folate receptor-β, Folate receptor-δ, Mucin 1, STEAP1, Mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P-Cadherin, Fibronectin Extra-domain B (ED-B), VEGFR2 (CD309), Tenascin, Collagen W, Periostin, endothelin receptor, HER 2, EGFR, CD30, CD79b, CD19, CD138, CD74, CD37, CD19, CD22, CD33, and CD98.

In some embodiments, the disclosure provides a method for treating a hyperproliferative disease that comprises administering an effective amount of a delivery vehicle (e.g., liposome) comprising alpha (L-alpha or D-alpha) or D-gamma polyglutamated (e.g., pentaglutamated or hexaglutamated) antifolate to a subject having or at risk of having a hyperproliferative disease. In some embodiments, the administered delivery vehicle is a liposome that comprises alpha polyglutamated antifolate. In some embodiments, the administered delivery vehicle is a liposome that comprises L-alpha polyglutamated antifolate. In some embodiments, the administered delivery vehicle is a liposome that comprises D-alpha polyglutamated antifolate. In some embodiments, the administered delivery vehicle is a liposome that comprises D-gamma polyglutamated antifolate. In some embodiments, the administered alpha or D-gamma polyglutamated antifolate is a member selected from the group consisting of: polyglutamated methotrexate (MTX), polyglutamated pemetrexed (PMX), polyglutamated lometrexol (LTX), polyglutamated AG2034, polyglutamated raltitrexed (RTX), polyglutamated piritrexim, polyglutamated pralatrexate, polyglutamated AG2034, polyglutamated GW1843, polyglutamated aminopterin, and polyglutamated LY309887. In some embodiments, the administered alpha or D-gamma polyglutamated antifolate comprises a pentaglutamated antifolate selected from the group consisting of pentaglutamated MTX, pentaglutamated PMX, pentaglutamated LTX, pentaglutamated AG2034, pentaglutamated RTX, pentaglutamated piritrexim, pentaglutamated pralatrexate, pentaglutamated AG2034, pentaglutamated GW1843, pentaglutamated aminopterin, and pentaglutamated LY309887. In some embodiments, the administered alpha or D-gamma polyglutamated antifolate comprises pentaglutamated PMX. In some embodiments, the administered alpha or D-gamma polyglutamated antifolate comprises pentaglutamated MTX. In some embodiments, the administered the alpha or D-gamma polyglutamated antifolate comprises pentaglutamated RTX. In some embodiments, the administered alpha or D-gamma polyglutamated antifolate comprises pentaglutamated LTX. In some embodiments, the administered alpha or D-gamma polyglutamated antifolate comprises a hexaglutamated antifolate selected from the group consisting of hexaglutamated MTX, hexaglutamated PMX, hexaglutamated LTX, hexaglutamated AG2034, hexaglutamated RTX, hexaglutamated piritrexim, hexaglutamated pralatrexate, hexaglutamated AG2034, hexaglutamated GW1843, hexaglutamated aminopterin, and hexaglutamated LY309887. In some embodiments, the administered alpha or D-gamma polyglutamated antifolate comprises hexaglutamated PMX. In some embodiments, the administered alpha or D-gamma polyglutamated antifolate comprises hexaglutamated MTX. In some embodiments, the administered the alpha or D-gamma polyglutamated antifolate comprises hexaglutamated RTX. In some embodiments, the administered alpha or D-gamma polyglutamated antifolate comprises hexaglutamated LTX. In some embodiments, the administered delivery vehicle is a liposome. In further embodiments, the liposome is pegylated. In additional embodiments, the delivery vehicle comprises a targeting moiety on its surface that specifically binds an antigen on the surface of a target cell of interest. In further embodiments, the delivery vehicle comprises a targeting moiety that specifically binds a cell surface antigen selected from the group consisting of GONMB, CD56, TACSTD2 (TROP2), CEACAM5, Folate receptor-α, Folate receptor-β, Folate receptor-δ, Mucin 1, STEAP1, Mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P-Cadherin, Fibronectin Extra-domain B (ED-B), VEGFR2 (CD309), Tenascin, Collagen IV, Periostin, endothelin receptor, HER 2, EGFR, CD30, CD79b, CD19, CD138, CD74, CD37, CD19, CD22, CD33, and CD98. In further embodiments, the delivery vehicle is a liposome, and the liposome comprises a targeting moiety that specifically binds a cell surface antigen selected from the group consisting of GONMB, CD56, TACSTD2 (TROP2), CEACAM5, Folate receptor-α, Folate receptor-β, Folate receptor-δ, Mucin 1, STEAP1, Mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P-Cadherin, Fibronectin Extra-domain B (ED-B), VEGFR2 (CD309), Tenascin, Collagen IV, Periostin, endothelin receptor, HER 2, EGFR, CD30, CD79b, CD19, CD138, CD74, CD37, CD19, CD22, CD33, and CD98.

In some embodiments, the disclosure provides a method for treating a disorder of the immune system (e.g., an autoimmune disease such as rheumatoid arthritis) that comprises administering an effective amount of a delivery vehicle (e.g., liposome) comprising alpha (L-alpha or D-alpha) or D-gamma polyglutamated (e.g., pentaglutamated or hexaglutamated) antifolate to a subject having or at risk of having an autoimmune disease. In some embodiments, the disorder of the immune system is an autoimmune disease. In further embodiments, the disorder of the immune system is rheumatoid arthritis. In some embodiments, the administered delivery vehicle is a liposome that comprises alpha polyglutamated antifolate. In some embodiments, the administered delivery vehicle is a liposome that comprises L-alpha polyglutamated antifolate. In some embodiments, the administered delivery vehicle is a liposome that comprises D-alpha polyglutamated antifolate. In some embodiments, the administered delivery vehicle is a liposome that comprises D-gamma polyglutamated antifolate. In some embodiments, the administered alpha or D-gamma polyglutamated antifolate is a member selected from the group consisting of: polyglutamated methotrexate (MTX), polyglutamated pemetrexed (PMX), polyglutamated lometrexol (LTX), polyglutamated AG2034, polyglutamated raltitrexed (RTX), polyglutamated piritrexim, polyglutamated pralatrexate, polyglutamated AG2034, polyglutamated GW1843, polyglutamated aminopterin, and polyglutamated LY309887. In some embodiments, the administered polyglutamated antifolate comprises an alpha (L-alpha or D-alpha) or D-gamma pentaglutamated antifolate selected from the group consisting of pentaglutamated MTX, pentaglutamated PMX, pentaglutamated LTX, pentaglutamated AG2034, pentaglutamated RTX, pentaglutamated piritrexim, pentaglutamated pralatrexate, pentaglutamated AG2034, pentaglutamated GW1843, pentaglutamated aminopterin, and pentaglutamated LY309887. In some embodiments, the administered alpha or D-gamma polyglutamated antifolate comprises a hexaglutamated PMX. In some embodiments, the administered polyglutamated antifolate comprises an alpha (L-alpha or D-alpha) or D-gamma hexaglutamated antifolate selected from the group consisting of hexaglutamated MTX, hexaglutamated PMX, hexaglutamated LTX, hexaglutamated AG2034, hexaglutamated RTX, hexaglutamated piritrexim, hexaglutamated pralatrexate, hexaglutamated AG2034, hexaglutamated GW1843, hexaglutamated aminopterin, and hexaglutamated LY309887. In some embodiments, the administered alpha or D-gamma polyglutamated antifolate comprises a hexaglutamated PMX. In some embodiments, the administered alpha (L-alpha or D-alpha) or D-gamma polyglutamated antifolate comprises alpha or D-gamma pentaglutamated MTX. In some embodiments, the administered alpha (L-alpha or D-alpha) or D-gamma polyglutamated antifolate comprises alpha or D-gamma hexaglutamated MTX. In some embodiments, administered alpha (L-alpha or D-alpha) or D-gamma polyglutamated antifolate comprises a pentaglutamated RTX. In some embodiments, administered alpha (L-alpha or D-alpha) or D-gamma polyglutamated antifolate comprises a hexaglutamated RTX. In some embodiments, the administered alpha or D-gamma polyglutamated antifolate comprises pentaglutamated pralatrexate (PTX). In some embodiments, the administered alpha or D-gamma polyglutamated antifolate comprises hexaglutamated pralatrexate (PTX). In some embodiments, the administered alpha or D-gamma polyglutamated antifolate comprises lometrexol (LTX). In some embodiments, the administered alpha or D-gamma polyglutamated antifolate comprises lometrexol (LTX). In some embodiments, the administered alpha or D-gamma polyglutamated antifolate comprises pentaglutamated lometrexol (LTX). In some embodiments, the administered alpha or D-gamma polyglutamated antifolate comprises hexaglutamated lometrexol (LTX).

In some embodiments, the administered delivery vehicle is a liposome. In further embodiments, the liposome is pegylated. In additional embodiments, the delivery vehicle comprises a targeting moiety on its surface that specifically binds an antigen on the surface of a target cell of interest. In further embodiments, the delivery vehicle comprises a targeting moiety that specifically binds a cell surface antigen selected from the group consisting of GONMB, CD56, TACSTD2 (TROP2), CEACAM5, Folate receptor-α, Folate receptor-β, Folate receptor-δ, Mucin 1, STEAP1, Mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P-Cadherin, Fibronectin Extra-domain B (ED-B), VEGFR2 (CD309), Tenascin, Collagen IV, Periostin, endothelin receptor, HER 2, EGFR, CD30, CD79b, CD19, CD138, CD74, CD37, CD19, CD22, CD33, and CD98. In further embodiments, the delivery vehicle is a liposome, and the liposome comprises a targeting moiety that specifically binds a cell surface antigen selected from the group consisting of GONMB, CD56, TACSTD2 (TROP2), CEACAM5, Folate receptor-α, Folate receptor-β, Folate receptor-δ, Mucin 1, STEAP1, Mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P-Cadherin, Fibronectin Extra-domain B (ED-B), VEGFR2 (CD309), Tenascin, Collagen W, Periostin, endothelin receptor, HER 2, EGFR, CD30, CD79b, CD19, CD138, CD74, CD37, CD19, CD22, CD33, and CD98.

In some embodiments, the disclosure provides a method for treating cancer that comprises administering an effective amount of a delivery vehicle (e.g., liposome) comprising alpha (L-alpha or D-alpha) or D-gamma polyglutamated (e.g., pentaglutamated or hexaglutamated) antifolate to a subject having or at risk of having cancer. In some embodiments, the cancer is a cancer selected from the group consisting of: lung (e.g., non-small lung cancer), pancreatic, breast cancer, ovarian, lung, prostate, head and neck, gastric, gastrointestinal, colon, esophageal, cervical, kidney, biliary duct, gallbladder, and a hematologic malignancy (e.g., a leukemia or lymphoma). In some embodiments, the administered delivery vehicle is a liposome that comprises alpha polyglutamated antifolate. In some embodiments, the administered delivery vehicle is a liposome that comprises L-alpha polyglutamated antifolate. In some embodiments, the administered delivery vehicle is a liposome that comprises D-alpha polyglutamated antifolate. In some embodiments, the administered delivery vehicle is a liposome that comprises D-gamma polyglutamated antifolate. In some embodiments, the administered alpha (L-alpha or D-alpha) or D-gamma polyglutamated antifolate is a member selected from the group consisting of: polyglutamated methotrexate (MTX), polyglutamated pemetrexed (PMX), polyglutamated lometrexol (LTX), polyglutamated AG2034, polyglutamated raltitrexed (RTX), polyglutamated piritrexim, polyglutamated pralatrexate, polyglutamated AG2034, polyglutamated GW1843, polyglutamated aminopterin, and polyglutamated LY309887. In some embodiments, the administered alpha (L-alpha or D-alpha) or D-gamma polyglutamated antifolate comprises a pentaglutamated antifolate selected from the group consisting of pentaglutamated MTX, pentaglutamated PMX, pentaglutamated LTX, pentaglutamated AG2034, pentaglutamated RTX, pentaglutamated piritrexim, pentaglutamated pralatrexate, pentaglutamated AG2034, pentaglutamated GW1843, pentaglutamated aminopterin, and pentaglutamated LY309887. In some embodiments, the administered alpha (L-alpha or D-alpha) or D-gamma polyglutamated antifolate comprises a hexaglutamated antifolate selected from the group consisting of hexaglutamated MTX, hexaglutamated PMX, hexaglutamated LTX, hexaglutamated AG2034, hexaglutamated RTX, hexaglutamated piritrexim, hexaglutamated pralatrexate, hexaglutamated AG2034, hexaglutamated GW1843, hexaglutamated aminopterin, and hexaglutamated LY309887. In some embodiments, the administered alpha (L-alpha or D-alpha) or D-gamma polyglutamated antifolate comprises pentaglutamated PMX. In some embodiments, the administered alpha (L-alpha or D-alpha) or D-gamma polyglutamated antifolate comprises hexaglutamated PMX. In some embodiments, the administered alpha (L-alpha or D-alpha) or D-gamma polyglutamated antifolate comprises pentaglutamated MTX. In some embodiments, the administered alpha (L-alpha or D-alpha) or D-gamma polyglutamated antifolate comprises hexaglutamated MTX. In some embodiments, the administered alpha (L-alpha or D-alpha) or D-gamma polyglutamated antifolate comprises pentaglutamated RTX. In some embodiments, the administered alpha (L-alpha or D-alpha) or D-gamma polyglutamated antifolate comprises hexaglutamated RTX. In some embodiments, the administered alpha (L-alpha or D-alpha) or D-gamma polyglutamated antifolate comprises pentaglutamated LTX. In some embodiments, the administered alpha (L-alpha or D-alpha) or D-gamma polyglutamated antifolate comprises hexaglutamated LTX.

In some embodiments, the administered delivery vehicle is a liposome. In further embodiments, the liposome is pegylated. In additional embodiments, the delivery vehicle comprises a targeting moiety on its surface that specifically binds an antigen on the surface of a target cell of interest. In further embodiments, the delivery vehicle comprises a targeting moiety that specifically binds a cell surface antigen selected from the group consisting of GONMB, CD56, TACSTD2 (TROP2), CEACAM5, Folate receptor-α, Folate receptor-β, Folate receptor-δ, Mucin 1, STEAP1, Mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P-Cadherin, Fibronectin Extra-domain B (ED-B), VEGFR2 (CD309), Tenascin, Collagen IV, Periostin, endothelin receptor, HER 2, EGFR, CD30, CD79b, CD19, CD138, CD74, CD37, CD19, CD22, CD33, and CD98. In further embodiments, the delivery vehicle is a liposome, and the liposome comprises a targeting moiety that specifically binds a cell surface antigen selected from the group consisting of GONMB, CD56, TACSTD2 (TROP2), CEACAM5, Folate receptor-α, Folate receptor-β, Folate receptor-δ, Mucin 1, STEAP1, Mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P-Cadherin, Fibronectin Extra-domain B (ED-B), VEGFR2 (CD309), Tenascin, Collagen IV, Periostin, endothelin receptor, HER 2, EGFR, CD30, CD79b, CD19, CD138, CD74, CD37, CD19, CD22, CD33, and CD98. In some embodiments, the delivery vehicle is a liposome that comprises alpha polyglutamated antifolate. In some embodiments, the administered delivery vehicle is a liposome that comprises L-alpha polyglutamated antifolate. In some embodiments, the administered delivery vehicle is a liposome that comprises D-alpha polyglutamated antifolate. In some embodiments, the administered delivery vehicle is a liposome that comprises D-gamma polyglutamated antifolate.

In some embodiments, the disclosure provides a method for treating lung cancer (e.g., non-small lung cancer) that comprises administering an effective amount of a delivery vehicle (e.g., liposome) comprising alpha (L-alpha or D-alpha) or D-gamma polyglutamated (e.g., pentaglutamated or hexaglutamated) antifolate to a subject having or at risk of having lung cancer. In particular embodiments, the cancer is non-small cell lung cancer. In some embodiments, the administered delivery vehicle is a liposome that comprises alpha polyglutamated antifolate. In some embodiments, the administered delivery vehicle is a liposome that comprises L-alpha polyglutamated antifolate. In some embodiments, the administered delivery vehicle is a liposome that comprises D-alpha polyglutamated antifolate. In some embodiments, the administered delivery vehicle is a liposome that comprises D-gamma polyglutamated antifolate. In some embodiments, the administered alpha or D-gamma polyglutamated antifolate is a member selected from the group consisting of: polyglutamated methotrexate (MTX), polyglutamated pemetrexed (PMX), polyglutamated lometrexol (LTX), polyglutamated AG2034, polyglutamated raltitrexed (RTX), polyglutamated piritrexim, polyglutamated pralatrexate, polyglutamated AG2034, polyglutamated GW1843, polyglutamated aminopterin, and polyglutamated LY309887. In some embodiments, the administered alpha or D-gamma polyglutamated antifolate comprises a pentaglutamated antifolate selected from the group consisting of pentaglutamated MTX, pentaglutamated PMX, pentaglutamated LTX, pentaglutamated AG2034, pentaglutamated RTX, pentaglutamated piritrexim, pentaglutamated pralatrexate, pentaglutamated AG2034, pentaglutamated GW1843, pentaglutamated aminopterin, and pentaglutamated LY309887. In some embodiments, the administered alpha or D-gamma polyglutamated antifolate comprises a hexaglutamated antifolate selected from the group consisting of hexaglutamated MTX, hexaglutamated PMX, hexaglutamated LTX, hexaglutamated AG2034, hexaglutamated RTX, hexaglutamated piritrexim, hexaglutamated pralatrexate, hexaglutamated AG2034, hexaglutamated GW1843, hexaglutamated aminopterin, and hexaglutamated LY309887. In particular embodiments, the administered alpha or D-gamma polyglutamated antifolate comprises pentaglutamated PMX. In particular embodiments, the administered alpha or D-gamma polyglutamated antifolate comprises hexaglutamated PMX. In some embodiments, the administered alpha or D-gamma polyglutamated antifolate comprises pentaglutamated MTX. In some embodiments, the administered alpha or D-gamma polyglutamated antifolate comprises hexaglutamated MTX. In some embodiments, the administered alpha or D-gamma polyglutamated antifolate comprises pentaglutamated RTX. In some embodiments, the administered alpha or D-gamma polyglutamated antifolate comprises hexaglutamated RTX. In some embodiments, the administered alpha or D-gamma polyglutamated antifolate comprises pentaglutamated LTX. In some embodiments, the administered alpha or D-gamma polyglutamated antifolate comprises hexaglutamated LTX. In some embodiments, the administered delivery vehicle is a liposome. In further embodiments, the liposome is pegylated. In additional embodiments, the delivery vehicle comprises a targeting moiety on its surface that specifically binds an antigen on the surface of a lung cancer (e.g., non-small cell lung cancer) cell. In further embodiments, the delivery vehicle comprises a targeting moiety that specifically binds a cell surface antigen selected from the group consisting of Mucin 1, Nectin 4, NaPi2b, CD56, EGFR, and SC-16. In further embodiments, the delivery vehicle is a liposome, and the liposome comprises a targeting moiety that specifically binds a cell surface antigen selected from the group consisting of Mucin 1, Nectin 4, NaPi2b, CD56, EGFR, and SC-16.

In some embodiments, the disclosure provides a method for treating pancreatic cancer that comprises administering an effective amount of a delivery vehicle (e.g., liposome) comprising alpha or D-gamma polyglutamated (e.g., pentaglutamated or hexaglutamated) antifolate to a subject having or at risk of having pancreatic cancer. In some embodiments, the administered delivery vehicle is a liposome that comprises alpha polyglutamated antifolate. In some embodiments, the administered delivery vehicle is a liposome that comprises L-alpha polyglutamated antifolate. In some embodiments, the administered delivery vehicle is a liposome that comprises D-alpha polyglutamated antifolate. In some embodiments, the administered delivery vehicle is a liposome that comprises D-gamma polyglutamated antifolate. In some embodiments, the administered alpha or D-gamma polyglutamated antifolate is a member selected from the group consisting of: polyglutamated methotrexate (MTX), polyglutamated pemetrexed (PMX), polyglutamated lometrexol (LTX), polyglutamated AG2034, polyglutamated raltitrexed (RTX), polyglutamated piritrexim, polyglutamated pralatrexate, polyglutamated AG2034, polyglutamated GW1843, polyglutamated aminopterin, and polyglutamated LY309887. In some embodiments, the administered alpha or D-gamma polyglutamated antifolate comprises a pentaglutamated antifolate selected from the group consisting of pentaglutamated MTX, pentaglutamated PMX, pentaglutamated LTX, pentaglutamated AG2034, pentaglutamated RTX, pentaglutamated piritrexim, pentaglutamated pralatrexate, pentaglutamated AG2034, pentaglutamated GW1843, pentaglutamated aminopterin, and pentaglutamated LY309887. In some embodiments, the administered alpha or D-gamma polyglutamated antifolate comprises a hexaglutamated antifolate selected from the group consisting of hexaglutamated MTX, hexaglutamated PMX, hexaglutamated LTX, hexaglutamated AG2034, hexaglutamated RTX, hexaglutamated piritrexim, hexaglutamated pralatrexate, hexaglutamated AG2034, hexaglutamated GW1843, hexaglutamated aminopterin, and hexaglutamated LY309887. In particular embodiments, the administered alpha (L-alpha or D-alpha) or D-gamma polyglutamated antifolate comprises pentaglutamated PMX. In particular embodiments, the administered alpha (L-alpha or D-alpha) or D-gamma polyglutamated antifolate comprises hexaglutamated PMX. In some embodiments, the administered alpha (L-alpha or D-alpha) or D-gamma polyglutamated antifolate comprises pentaglutamated MTX. In some embodiments, the administered alpha (L-alpha or D-alpha) or D-gamma polyglutamated antifolate comprises hexaglutamated MTX. In some embodiments, the administered alpha (L-alpha or D-alpha) or D-gamma polyglutamated antifolate comprises pentaglutamated RTX. In some embodiments, the administered alpha (L-alpha or D-alpha) or D-gamma polyglutamated antifolate comprises hexaglutamated RTX. In some embodiments, the administered alpha (L-alpha or D-alpha) or D-gamma polyglutamated antifolate comprises pentaglutamated LTX. In some embodiments, the administered alpha (L-alpha or D-alpha) or D-gamma polyglutamated antifolate comprises hexaglutamated LTX. In some embodiments, the administered delivery vehicle is a liposome. In further embodiments, the liposome is pegylated. In additional embodiments, the delivery vehicle comprises a targeting moiety on its surface that specifically binds an antigen on the surface of a pancreatic cancer cell. In further embodiments, the delivery vehicle comprises a targeting moiety that specifically binds a cell surface antigen selected from the group consisting of TACSTD2 (TROP2), Mucin 1, Mesothelin, Guanylyl cyclase C (GCC), SLC44A4, and Nectin 4. In further embodiments, the delivery vehicle is a liposome, and the liposome comprises a targeting moiety that specifically binds a cell surface antigen selected from the group consisting of TACSTD2 (TROP2), Mucin 1, Mesothelin, Guanylyl cyclase C (GCC), SLC44A4, and Nectin 4.

In additional embodiments, the disclosure provides a method for treating breast cancer (e.g., triple negative breast cancer (estrogen receptor$^-$, progesterone receptor$^-$, and HER2) that comprises administering an effective amount of a delivery vehicle (e.g., liposome) comprising alpha (L-alpha or D-alpha) or D-gamma polyglutamated (e.g., pentaglutamated or hexaglutamated) antifolate to a subject having or at risk of having breast cancer. In some embodiments, the administered delivery vehicle is a liposome that comprises alpha polyglutamated antifolate. In some embodiments, the administered delivery vehicle is a liposome that comprises L-alpha polyglutamated antifolate. In some embodiments, the administered delivery vehicle is a liposome that comprises D-alpha polyglutamated antifolate. In some embodiments, the administered delivery vehicle is a liposome that comprises D-gamma polyglutamated antifolate. In some embodiments, the administered alpha (L-alpha or D-alpha) or D-gamma polyglutamated antifolate is a member selected from the group consisting of: polyglutamated methotrexate (MTX), polyglutamated pemetrexed (PMX), polyglutamated lometrexol (LTX), polyglutamated AG2034, polyglutamated raltitrexed (RTX), polyglutamated piritrexim, polyglutamated pralatrexate, polyglutamated AG2034, polyglutamated GW1843, polyglutamated aminopterin, and polyglutamated LY309887. In some embodiments, the administered alpha (L-alpha or D-alpha) or D-gamma polyglutamated antifolate comprises a pentaglutamated antifolate selected from the group consisting of pentaglutamated MTX, pentaglutamated PMX, pentaglutamated LTX, pentaglutamated AG2034, pentaglutamated RTX, pentaglutamated piritrexim, pentaglutamated pralatrexate, pentaglutamated AG2034, pentaglutamated GW1843, pentaglutamated aminopterin, and pentaglutamated LY309887. In some embodiments, the administered alpha (L-alpha or D-alpha) or D-gamma polyglutamated antifolate comprises a pentaglutamated antifolate selected from the group consisting of hexaglutamated MTX, hexaglutamated PMX, hexaglutamated LTX, hexaglutamated AG2034, hexaglutamated RTX, hexaglutamated piritrexim, hexaglutamated pralatrexate, hexaglutamated AG2034, hexaglutamated GW1843, hexaglutamated aminopterin, and hexaglutamated LY309887. In particular embodiments, the administered alpha (L-alpha or D-alpha) or D-gamma polyglutamated antifolate comprises pentaglutamated PMX. In particular embodiments, the administered alpha (L-alpha or D-alpha) or D-gamma polyglutamated antifolate comprises hexaglutamated PMX. In some embodiments, the administered alpha (L-alpha or D-alpha) or D-gamma polyglutamated antifolate comprises pentaglutamated MTX. In some embodiments, the administered alpha (L-alpha or D-alpha) or D-gamma polyglutamated antifolate comprises hexaglutamated MTX. In some embodiments, the administered alpha (L-alpha or D-alpha) or D-gamma polyglutamated antifolate comprises pentaglutamated RTX. In some embodiments, the administered alpha (L-alpha or D-alpha) or D-gamma polyglutamated antifolate comprises hexaglutamated RTX. In some embodiments, the administered alpha (L-alpha or D-alpha) or D-gamma polyglutamated antifolate comprises pentaglutamated LTX. In some embodiments, the administered alpha (L-alpha or D-alpha) or D-gamma polyglutamated antifolate comprises hexaglutamated LTX. In some embodiments, the administered delivery vehicle is a liposome. In further embodiments, the liposome is pegylated. In additional embodiments, the delivery vehicle comprises a targeting moiety on its surface that specifically binds an antigen on the surface of a breast cancer cell. In further embodiments, the delivery vehicle comprises a targeting moiety that specifically binds a cell surface antigen selected from the group consisting of LIV-1 (ZIP6), EGFR, HER2, HER3, Mucin 1, GONMB, and Nectin 4. In further embodiments, the delivery vehicle is a liposome, and the liposome comprises a targeting moiety that specifically binds a cell surface antigen selected from the group consisting of: LIV-1 (ZIP6), EGFR, HER2, HER3, Mucin 1, GONMB, and Nectin 4.

In some embodiments, the provided compositions (e.g., liposomes containing alpha (L-alpha or D-alpha) or D-gamma polyglutamated antifolates) are administered to subjects having or at risk of having a hematological cancer that is distinguishable by the expression of a tumor specific antigen or tumor associated antigen on its cell surface. Thus, in some embodiments, the disclosure provides a method for treating cancer that comprises administering an effective amount of a delivery vehicle (e.g., liposome) comprising a targeting moiety and an alpha (L-alpha or D-alpha) or D-gamma polyglutamated (e.g., pentaglutamated or hexaglutamated) antifolate to a subject having or at risk of having a cancer, solid tumor, and/or metastasis that is distinguishable by the expression of a tumor specific antigen or tumor associated antigen on its cell surface cancer, and wherein the targeting moiety is expressed on the surface of the delivery vehicle and specifically binds the tumor specific antigen or tumor associated antigen. In some embodiments, the administered delivery vehicle is a liposome that comprises alpha polyglutamated antifolate. In some embodiments, the administered delivery vehicle is a liposome that comprises L-alpha polyglutamated antifolate. In some embodiments, the administered delivery vehicle is a liposome that comprises D-alpha polyglutamated antifolate. In some embodiments, the administered delivery vehicle is a liposome that comprises D-gamma polyglutamated antifolate. In some embodiments, the administered alpha or D-gamma polyglutamated antifolate is a member selected from the group consisting of: polyglutamated methotrexate (MTX), polyglutamated pemetrexed (PMX), polyglutamated lometrexol (LTX), polyglutamated AG2034, polyglutamated raltitrexed (RTX), polyglutamated piritrexim, polyglutamated pralatrexate, polyglutamated AG2034, polyglutamated GW1843, polyglutamated aminopterin, and polyglutamated LY309887. In some embodiments, the administered alpha or D-gamma polyglutamated antifolate comprises a pentaglutamated antifolate selected from the group consisting of pentaglutamated MTX, pentaglutamated PMX, pentaglutamated LTX, pentaglutamated AG2034, pentaglutamated RTX, pentaglutamated piritrexim, pentaglutamated pralatrexate, pentaglutamated AG2034, pentaglutamated GW1843, pentaglutamated aminopterin, and pentaglutamated LY309887. In some embodiments, the administered alpha or D-gamma polyglutamated antifolate comprises a hexaglutamated antifolate selected from the group consisting of hexaglutamated MTX, hexaglutamated PMX, hexaglutamated LTX, hexaglutamated AG2034, hexaglutamated RTX, hexaglutamated piritrexim, hexaglutamated pralatrexate, hexaglutamated AG2034, hexaglutamated GW1843, hexaglutamated aminopterin, and hexaglutamated LY309887. In particular embodiments, the administered alpha or D-gamma polyglutamated antifolate comprises pentaglutamated PMX. In particular embodiments, the administered alpha or D-gamma polyglutamated antifolate comprises hexaglutamated PMX. In some embodiments, the administered alpha or D-gamma polyglutamated antifolate comprises pentaglutamated MTX. In some embodiments, the administered alpha or D-gamma polyglutamated antifolate comprises hexaglutamated MTX. In some embodiments, the administered alpha or D-gamma polyglutamated antifolate comprises pentaglutamated RTX. In some embodiments, the administered alpha or D-gamma polyglutamated antifolate comprises hexaglutamated RTX. In some embodiments, the administered alpha or D-gamma polyglutamated antifolate comprises pentaglutamated LTX. In some embodiments, the administered alpha or D-gamma polyglutamated antifolate comprises hexaglutamated LTX. In some embodiments, the administered delivery vehicle is a liposome. In further embodiments, the liposome is pegylated. In additional embodiments, the delivery vehicle comprises a targeting moiety that specifically binds a cell surface antigen expressed on the surface of a hematological cancer cell. In additional embodiments, the targeting moiety specifically binds a cell surface antigen selected from the group consisting of CD30, CD79b, CD19, CD138, CD74, CD37, CD19, CD22, CD33, and CD98. In further embodiments, the delivery vehicle is a liposome, and the liposome comprises a targeting moiety that specifically binds a cell surface antigen selected from the group consisting of CD30, CD79b, CD19, CD138, CD74, CD37, CD19, CD22, CD33, and CD98.

In some embodiments the disclosed compositions (e.g., liposomes containing alpha (L-alpha or D-alpha) or D-gamma polyglutamated antifolates) are administered to subjects having or at risk of having a cancer, a solid tumor, and/or a metastasis that is distinguishable by the expression of a tumor specific antigen or tumor associated antigen on its cell surface. Thus, in some embodiments, the disclosure provides a method for treating cancer that comprises administering an effective amount of a delivery vehicle (e.g., liposome) comprising a targeting moiety and alpha (L-alpha or D-alpha) or D-gamma polyglutamated (e.g., pentaglutamated or hexaglutamated) antifolate to a subject having or at risk of having a cancer, solid tumor, and/or metastasis that is distinguishable by the expression of a tumor specific antigen or tumor associated antigen on its cell surface cancer, and wherein the targeting moiety is expressed on the surface of the delivery vehicle and specifically binds the tumor specific antigen or tumor associated antigen. In some embodiments, the administered delivery vehicle is a liposome that comprises alpha polyglutamated antifolate. In some embodiments, the administered delivery vehicle is a liposome that comprises L-alpha polyglutamated antifolate. In some embodiments, the administered delivery vehicle is a liposome that comprises D-alpha polyglutamated antifolate. In some embodiments, the administered delivery vehicle is a liposome that comprises D-gamma polyglutamated antifolate. In some embodiments, the administered alpha or D-gamma polyglutamated antifolate is a member selected from the group consisting of: polyglutamated methotrexate (MTX), polyglutamated pemetrexed (PMX), polyglutamated lometrexol (LTX), polyglutamated AG2034, polyglutamated raltitrexed (RTX), polyglutamated piritrexim, polyglutamated pralatrexate, polyglutamated AG2034, polyglutamated GW1843, polyglutamated aminopterin, and polyglutamated LY309887. In some embodiments, the administered alpha or D-gamma polyglutamated antifolate comprises a pentaglutamated antifolate selected from the group consisting of pentaglutamated MTX, pentaglutamated PMX, pentaglutamated LTX, pentaglutamated AG2034, pentaglutamated RTX, pentaglutamated piritrexim, pentaglutamated pralatrexate, pentaglutamated AG2034, pentaglutamated GW1843, pentaglutamated aminopterin, and pentaglutamated LY309887. In some embodiments, the administered alpha or D-gamma polyglutamated antifolate comprises a hexaglutamated antifolate selected from the group consisting of hexaglutamated MTX, hexaglutamated PMX, hexaglutamated LTX, hexaglutamated AG2034, hexaglutamated RTX, hexaglutamated piritrexim, hexaglutamated pralatrexate, hexaglutamated AG2034, hexaglutamated GW1843, hexaglutamated aminopterin, and hexaglutamated LY309887. In particular embodiments, the administered alpha or D-gamma polyglutamated antifolate comprises pentaglutamated PMX. In particular embodiments, the administered alpha or D-gamma polyglutamated antifolate comprises hexaglutamated PMX. In some embodiments, the administered alpha or D-gamma polyglutamated antifolate comprises pentaglutamated MTX. In some embodiments, the administered alpha or D-gamma polyglutamated antifolate comprises hexaglutamated MTX. In some embodiments, the administered alpha or D-gamma polyglutamated antifolate comprises pentaglutamated RTX. In some embodiments, the administered alpha or D-gamma polyglutamated antifolate comprises hexaglutamated RTX. In some embodiments, the administered alpha or D-gamma polyglutamated antifolate comprises pentaglutamated LTX. In some embodiments, the administered alpha or D-gamma polyglutamated antifolate comprises hexaglutamated LTX In some embodiments, the administered delivery vehicle is a liposome. In further embodiments, the liposome is pegylated. In additional embodiments, the delivery vehicle comprises a targeting moiety that specifically binds a cell surface antigen expressed on the surface of a cancer, a solid tumor, and/or a metastatic cell. In additional embodiments, targeting moiety specifically binds a cell surface antigen selected from the group consisting of GONMB, CD56, TACSTD2 (TROP2), CEACAM5, Folate receptor-α, Folate receptor-β, Folate receptor-δ, Mucin 1, STEAP1, Mesothelin, Nectin 4, ENPP3, Guanylyl cyclase C (GCC), SLC44A4, NaPi2b, CD70 (INFSF7), CA9 (Carbonic anhydrase), 5T4 (TPBG), SLTRK6, SC-16, Tissue factor, LIV-1 (ZIP6), CGEN-15027, P-Cadherin, Fibronectin Extra-domain B (ED-B), VEGFR2 (CD309), Tenascin, Collagen IV, Periostin, endothelin receptor, HER 2, EGFR, CD30, CD79b, CD19, CD138, CD74, CD37, CD19, CD22, CD33, and CD98. In further embodiments, the delivery vehicle is a liposome, and the liposome comprises a targeting moiety that specifically binds a cell surface antigen selected from the group consisting of GONMB, CD56, TACSTD2 (TROP2), CEACAM5, Folate receptor-α, Folate receptor-β, Folate receptor-δ, Mucin 1, STEAP1, Mesothelin, Nectin 4, ENPP3, Guanylyl cyclase C (GCC), SLC44A4, NaPi2b, CD70 (TNFSF7), CA9 (Carbonic anhydrase), 5T4 (TPBG), SLTRK6, SC-16, Tissue factor, LIV-1 (ZIP6), CGEN-15027, P-Cadherin, Fibronectin Extra-domain B (ED-B), VEGFR2 (CD309), Tenascin, Collagen W, Periostin, endothelin receptor, HER 2, EGFR, CD30, CD79b, CD19, CD138, CD74, CD37, CD19, CD22, CD33, and CD98.

In further embodiments, the disclosure provides a method for treating cancer that comprises administering an effective amount of a delivery vehicle (e.g., liposome) comprising a targeting moiety on its surface that specifically binds a folate receptor, and an alpha (L-alpha or D-alpha) or D-gamma polyglutamated (e.g., pentaglutamated or hexaglutamated) antifolate to a subject having or at risk of having a cancer that contains cells expressing the folate receptor on their cell surface. In some embodiments, the administered delivery vehicle is a liposome that comprises alpha polyglutamated antifolate. In some embodiments, the administered delivery vehicle is a liposome that comprises L-alpha polyglutamated antifolate. In some embodiments, the administered delivery vehicle is a liposome that comprises D-alpha polyglutamated antifolate. In some embodiments, the administered delivery vehicle is a liposome that comprises D-gamma polyglutamated antifolate. In further embodiments, the folate receptor is folate receptor alpha, folate receptor beta or folate receptor delta. In some embodiments, the administered alpha or D-gamma polyglutamated antifolate is a member selected from the group consisting of: polyglutamated methotrexate (MTX), polyglutamated pemetrexed (PMX), polyglutamated lometrexol (LTX), polyglutamated AG2034, polyglutamated raltitrexed (RTX), polyglutamated piritrexim, polyglutamated pralatrexate, polyglutamated AG2034, polyglutamated GW1843, polyglutamated aminopterin, and polyglutamated LY309887. In some embodiments, the administered alpha or D-gamma polyglutamated antifolate comprises a pentaglutamated antifolate selected from the group consisting of pentaglutamated MTX, pentaglutamated PMX, pentaglutamated LTX, pentaglutamated AG2034, pentaglutamated RTX, pentaglutamated piritrexim, pentaglutamated pralatrexate, pentaglutamated AG2034, pentaglutamated GW1843, pentaglutamated aminopterin, and pentaglutamated LY309887. In some embodiments, the administered alpha or D-gamma polyglutamated antifolate comprises a hexaglutamated antifolate selected from the group consisting of hexaglutamated MTX, hexaglutamated PMX, hexaglutamated LTX, hexaglutamated AG2034, hexaglutamated RTX, hexaglutamated piritrexim, hexaglutamated pralatrexate, hexaglutamated AG2034, hexaglutamated GW1843, hexaglutamated aminopterin, and hexaglutamated LY309887. In particular embodiments, the administered alpha or D-gamma polyglutamated antifolate comprises pentaglutamated PMX. In particular embodiments, the administered alpha or D-gamma polyglutamated antifolate comprises hexaglutamated PMX. In some embodiments, the administered alpha or D-gamma polyglutamated antifolate comprises pentaglutamated MTX. In some embodiments, the administered alpha or D-gamma polyglutamated antifolate comprises hexaglutamated MTX. In some embodiments, the administered alpha or D-gamma polyglutamated antifolate comprises pentaglutamated RTX. In some embodiments, the administered alpha or D-gamma polyglutamated antifolate comprises hexaglutamated RTX. In some embodiments, the administered alpha or D-gamma polyglutamated antifolate comprises pentaglutamated LTX. In some embodiments, the administered alpha or D-gamma polyglutamated antifolate comprises hrexaglutamated LTX In some embodiments, the administered delivery vehicle is a liposome. In further embodiments, the liposome is pegylated. As disclosed herein, the folate receptor targeted pegylated liposomes containing alpha or D-gamma polyglutamated antifolates are able to deliver high quantities of alpha or D-gamma polyglutamated antifolates to cancer cells and particularly cancer cells that express folate receptors, compared to normal cells (i.e., cells that unlike cancer cells do not actively take up liposomes, and/or do not express folate receptors). Any cancers that express folate receptors may be treated according to the disclosed methods. It should be noted that some cancers may express folate receptors in an early stage while the majority of cancers may express folate receptors at late stages.

Cancer that may be treated by the methods of the invention include carcinomas, sarcomas and melanomas. Carcinomas include without limitation to basal cell carcinoma, biliary tract cancer, bladder cancer, breast cancer, cervical cancer, choriocarcinoma, CNS cancer, colon and rectum cancer, kidney or renal cell cancer, larynx cancer, liver cancer, small cell lung cancer, non-small cell lung cancer (NSCLC, including adenocarcinoma, giant (or oat) cell carcinoma, and squamous cell carcinoma), oral cavity cancer, ovarian cancer, pancreatic cancer, prostate cancer, skin cancer (including basal cell cancer and squamous cell cancer), stomach cancer, testicular cancer, thyroid cancer, uterine cancer, rectal cancer, cancer of the respiratory system, and cancer of the urinary system.

Sarcomas are mesenchymal neoplasms that arise in bone (osteosarcomas) and soft tissues (fibrosarcomas). Sarcomas include without limitation liposarcomas (including myxoid liposarcomas and pleiomorphic liposarcomas), leiomyosarcomas, rhabdomyosarcomas, malignant peripheral nerve sheath tumors (also called malignant schwannomas, neurofibrosarcomas, or neurogenic sarcomas), Ewing's tumors (including Ewing's sarcoma of bone, extraskeletal (i.e., not bone) Ewing's sarcoma, and primitive neuroectodermal tumor), synovial sarcoma, angiosarcomas, hemangiosarcomas, lymphangiosarcomas, Kaposi's sarcoma, hemangioendothelioma, desmoid tumor (also called aggressive fibromatosis), dermatofibrosarcoma protuberans (DFSP), malignant fibrous histiocytoma (MFH), hemangiopericytoma, malignant mesenchymoma, alveolar soft-part sarcoma, epithelioid sarcoma, clear cell sarcoma, desmoplastic small cell tumor, gastrointestinal stromal tumor (GIST), and chondrosarcoma.

Melanomas are tumors arising from the melanocytic system of the skin and other organs. Examples of melanoma include without limitation lentigomaligna melanoma, superficial spreading melanoma, nodular melanoma, and acral lentiginous melanoma.

In some embodiments, the cancer treated by one or more of the methods disclosed herein is a solid tumor lymphoma. Examples of solid tumor lymphoma include Hodgkin's lymphoma, Non-Hodgkin's lymphoma, and B cell lymphoma.

In some embodiments, the cancer treated by one or more of the methods disclosed herein is bone cancer, brain cancer, breast cancer, colorectal cancer, connective tissue cancer, cancer of the digestive system, endometrial cancer, esophageal cancer, eye cancer, cancer of the head and neck, gastric cancer, intra-epithelial neoplasm, melanoma neuroblastoma, Non-Hodgkin's lymphoma, non-small cell lung cancer, prostate cancer, retinoblastoma, or rhabdomyosarcoma.

In some embodiments, the disclosure provides for the use of a composition comprising an alpha (L-alpha or D-alpha) or D-gamma polyglutamated antifolate polyglutamated antifolate for manufacture of a medicament for treatement of a hyperproliferative disease. In some embodiments, the polyglutamated antifolate comprise 5 or more glutamyl groups. In some embodiments, the pentaglutamated antifolate pentaglutamated or hexaglutamated. In some embodiments, the polyglutamated antifolate is a member selected from the group consisting of: polyglutamated methotrexate (MTX), polyglutamated pemetrexed (PMX), polyglutamated lometrexol (LTX), polyglutamated AG2034, polyglutamated raltitrexed (RTX), polyglutamated piritrexim, polyglutamated pralatrexate, polyglutamated AG2034, polyglutamated GW1843, polyglutamated aminopterin, and polyglutamated LY309887. In some embodiments, the polyglutamated antifolate is methotrexate (MTX). In some embodiments, the polyglutamated antifolate is polyglutamated pemetrexed (PMX). In some embodiments, the polyglutamated antifolate is polyglutamated lometrexol (LTX). In some embodiments, the polyglutamated antifolate is polyglutamated AG2034. In some embodiments, the polyglutamated antifolate is polyglutamated raltitrexed (RTX). In some embodiments, the polyglutamated antifolate is polyglutamated pralatrexate. In some embodiments, the polyglutamated antifolate is polyglutamated AG2034. In some embodiments, the polyglutamated antifolate is polyglutamated GW1843 In some embodiments, the polyglutamated antifolate is polyglutamated aminopterin. In some embodiments, the polyglutamated antifolate is polyglutamated LY309887. In some embodiments the poplyglutamated antifolate is in a liposome. In some embodiments the hyperproliferative disease is cancer. In some embodiments the cancer is selected from the group consisting of: lung (e.g., non-small lung cancer), pancreatic, breast cancer, ovarian, lung, prostate, head and neck, gastric, gastrointestinal, colon, esophageal, cervical, kidney, biliary duct, gallbladder, and a hematologic malignancy. In some embodiments the cancer is pancreatic cancer. In some embodiments the cancer is breast cancer. In some embodiments the cancer is pancreatic cancer. In some embodiments the cancer is triple negative breast cancer. In some embodiments the cancer is lung cancer. In some embodiments the cancer is non-small cell lung cancer. In some embodiments the cancer is leukemia or lymphoma. In some embodiments the hyperproliferative disease is an autoimmune disease. In some embodiments, the hyperproliferative disease is rheumatoid arthritis.

The disclosed methods can practiced in any subject that is likely to benefit from delivery of compositions contemplated herein (e.g., polyglutamated antifolate compositions such as liposome containing a pentaglutamated or hexaglutamated antifolate). Mammalian subjects, and in particular, human subjects are preferred. In some embodiments, the subjects also include animals such as household pets (e.g., dogs, cats, rabbits, and ferrets), livestock or farm animals (e.g., cows, pigs, sheep, chickens and other poultry), horses such as thoroughbred horses, laboratory animals (e.g., mice, rats, and rabbits), and other mammals. In other embodiments, the subjects include fish and other aquatic species.

The subjects to whom the agents are delivered may be normal subjects. Alternatively the subject may have or be at risk of developing a condition that can be diagnosed or that can benefit from delivery of one or more of the provided compositions. In some embodiments, such conditions include cancer (e.g., solid tumor cancers or non-solid cancer such as leukemias). In some embodiments, these conditions (e.g., cancers) involve cells that express an antigen that can be specifically bound by a targeted pegylated liposomal alpha (L-alpha or D-alpha) or D-gamma polyglutamated antifolate disclosed herein. In further embodiments, these antigens specifically bind and internalize the targeted pegylated liposomal alpha (L-alpha or D-alpha) or D-gamma polyglutamated antifolate into the cell. In some embodiments, the targeted pegylated liposomal alpha (L-alpha or D-alpha) or D-gamma polyglutamated antifolate specifically binds a folate receptor (e.g., folate receptor alpha (FR-α), folate receptor beta (FR-β) and folate receptor delta (FR-δ)) expressed on the surface of the cancer cell.

Tests for diagnosing the conditions that can be treated with the provided compositions are known in the art and will be familiar to the medical practitioner. The determination of whether a cell type expresses folate receptors can be made using commercially available antibodies. These laboratory tests include without limitation microscopic analyses, cultivation dependent tests (such as cultures), and nucleic acid detection tests. These include wet mounts, stain-enhanced microscopy, immune microscopy (e.g., FISH), hybridization microscopy, particle agglutination, enzyme-linked immunosorbent assays, urine screening tests, DNA probe hybridization, and serologic tests. The medical practitioner will generally also take a full history and conduct a complete physical examination in addition to running the laboratory tests listed above.

A subject having a cancer can, for example, be a subject that has detectable cancer cells. A subject at risk of developing a cancer can, for example, be a subject that has a higher than normal probability of developing cancer. These subjects include, for instance, subjects having a genetic abnormality that has been demonstrated to be associated with a higher likelihood of developing a cancer, subjects having a familial disposition to cancer, subjects exposed to cancer causing agents (i.e., carcinogens) such as tobacco, asbestos, or other chemical toxins, and subjects previously treated for cancer and in apparent remission.

In some embodiments, the disclosure provides methods for selectively deliver a folate receptor targeted pegylated liposomal alpha (L-alpha or D-alpha) or D-gamma polyglutamated antifolate to a tumor cell expressing a folate receptor on its surface at a rate that is higher (e.g. at least two-fold greater, at least three-fold greater, at least four-fold greater, or at least five-fold greater, than a cell not expressing folate receptor on its cell surface). In some embodiments, the delivered pegylated liposome comprises alpha polyglutamated antifolate. In some embodiments, the delivered pegylated liposome comprises L-alpha polyglutamated antifolate. In some embodiments, the delivered pegylated liposome comprises D-alpha polyglutamated antifolate. In some embodiments, the delivered pegylated liposome comprises D-gamma polyglutamated antifolate.

In some embodiments, the disclosure provides a method of making a liposomal composition disclosed herein. In one embodiment, the method includes forming a mixture comprising: (1) a liposomal component; and (2) a alpha (L-alpha or D-alpha) or D-gamma polyglutamated (e.g., pentaglutamated or hexaglutamated) antifolate in aqueous solution. In further embodiments, the mixture comprises a pegylated liposomal component. The mixture is then homogenized to form liposomes in the aqueous solution. Further, the mixture can be extruded through a membrane to form liposomes enclosing the alpha (L-alpha or D-alpha) or D-gamma polyglutamated antifolate in an aqueous solution. It is understood the liposomal components of this disclosure can comprise any lipid (including cholesterol) including functionalized lipids and lipids attached to targeting moieties, detectable labels, and steric stabilizers, or any subset of all of these. It is further noted that the bioactive alpha (L-alpha or D-alpha) or D-gamma polyglutamated antifolate in aqueous solution can comprise any reagents and chemicals discussed herein or otherwise known in the art for the interior or exterior of the liposome including, for example, buffers, salts, and cryoprotectants.

In some embodiments, the disclosure provides a method of making a targeted pegylated liposomal alpha (L-alpha or D-alpha) or D-gamma polyglutamated antifolate (targeted-PLPA) or non-targetd PLPA disclosed herein. In one embodiment, the method includes forming a mixture comprising: (I) a liposomal component; (2) a alpha (L-alpha or D-alpha) or D-gamma polyglutamated (e.g., pentaglutamated or hexaglutamated) antifolate in aqueous solution; and (3) the targeting moiety. The mixture is then homogenized to form liposomes in the aqueous solution. Further, the mixture may be extruded through a membrane to form liposomes enclosing the targeted alpha (L-alpha or D-alpha) or D-gamma polyglutamated antifolate in an aqueous solution. It is understood that the targeted pegylated liposomal components can comprise any lipid (including cholesterol) including functionalized lipids and lipids attached to targeting moieties, detectable labels, and steric stabilizers, or any subset of all of these. It is further noted that the targeted pegylated liposome can comprise any reagents and chemicals discussed herein or otherwise known in the art for the interior or exterior of the liposome including, for example, buffers, salts, and cryoprotectants.

The above methods optionally further comprise the step of lyophilizing the composition after the removing step to form a lyophilized composition. As stated above, targeted-PTPLA or non-targeted-PTPLA in aqueous solution may comprise a cryoprotectant described herein or otherwise known in the art. If the composition is to be lyophilized, a cryoprotectant may be preferred.

Additionally, after the lyophilizing step, the method optionally further comprises the step of reconstituting the lyophilized composition by dissolving the composition in a solvent after the lyophilizing step. Methods of reconstitution are known in the art. One preferred solvent is water. Other preferred solvents include saline solutions and buffered solutions.

While certain exemplary embodiments, are discussed herein, it is understood that liposomes can be made by any method that is known in the art. See, for example, G. Gregoriadis (editor), Liposome Technology, vol. 1-3, 1st edition, 1983; 2nd edition, 1993, CRC Press, 45 Boca Raton, Fla. Examples of methods suitable for making liposome compositions include extrusion, reverse phase evaporation, sonication, solvent (e.g., ethanol) injection, microfluidization, detergent dialysis, ether injection, and dehydration/rehydration. The size of liposomes can routinely be controlled by controlling the pore size of membranes used for low pressure extrusions or the pressure and number of passes utilized in microfluidization or any other suitable methods known in the art.

In general, the alpha (L-alpha or D-alpha) or D-gamma polyglutamated antifolate is contained inside, that is, in the inner (interior) space of the liposomes. In one embodiment, substituted ammonium is partially or substantially completely removed from the outer medium surrounding the liposomes. Such removal can be accomplished by any suitable means known in the art (e.g., dilution, ion exchange chromatography, size exclusion chromatography, dialysis, ultrafiltration, and precipitation). Accordingly, the methods of making liposomal compositions set forth above or otherwise known in the art can optionally further comprise the step of removing polyglutamated antifolate in aqueous solution outside of the liposomes after the extruding step.

In other embodiments, the disclosure provides a targeted pegylated liposomal alpha (L-alpha or D-alpha) or D-gamma polyglutamated antifolate (PLPA) that selectively targets folate receptors comprising: a liposome including an interior space, a alpha (L-alpha or D-alpha) or D-gamma polyglutamated antifolate disposed within the interior space, a steric stabilizer molecule attached to an exterior of the liposome, and a targeting moiety comprising a protein with specific affinity for at least one folate receptor, said targeting moiety attached to at least one of the steric stabilizer and the exterior of the liposome. The components of this embodiment may be the same as described for other embodiments, of this disclosure. For example, the targeted pegylated liposomal alpha (L-alpha or D-alpha) or D-gamma polyglutamated antifolate and the steric stabilizer which may be PEG, are as described in other parts of this disclosure.

In some embodiments the disclosure provides a method of preparing a targeted composition comprising a pegylated liposome including an entrapped and/or encapsulated alpha (L-alpha or D-alpha) or D-gamma polyglutamated antifolate; a targeting moiety an amino acid chain, the amino acid chain comprising a plurality of amino acids, the targeting moiety having a specific affinity for at least one type of folate receptor, the specific affinity being defined to include an equilibrium dissociation constant (Kd) in a range of $0.5 \times 10^{-10}$ to $10 \times 10^{-6}$ moles [0.05 nanoMole to 10 μMole] for at least one type folate receptor, 47 the targeting moiety attached to one or both of a PEG and an exterior of the liposome, the method comprising: forming a mixture comprising: liposomal components; alpha (L-alpha or D-alpha) or D-gamma polyglutamated antifolate in solution; homogenizing the mixture to form liposomes in the solution; processing the mixture to form liposomes entrapping and/or encapsulating alpha (L-alpha or D-alpha) or D-gamma polyglutamated antifolate; and providing the targeting moiety on a surface of the liposomes entrapping and/or encapsulating the polyglutamated antifolate, the targeting moiety having the specific affinity for at least one of folate receptor alpha (FR-α), folate receptor beta (FR-β) and folate receptor delta (FR-δ). In some embodiments the processing includes one or more of: thin film hydration, extrusion, in-line mixing, and stirring, and once the particles have been formed, the particles can have their sizes further modified by one or more of extrusion and sonication. In some embodiments, the targeted composition comprises at least 10% liposome entrapped polyglutamated antifolate. In some embodiments, the liposomes are anionic or neutral. In some embodiments, the targeting moiety has the specific affinity for one or more of: folate receptor alpha (FR-α), folate receptor beta (FR-β) and folate receptor delta (FR-δ). In further embodiments, the targeting moiety has the specific affinity for folate receptor alpha (FR-α) and folate receptor beta (FR-β). In additional embodiments, the targeting moiety has the specific affinity for an epitope on a tumor cell surface antigen that is present on a tumor cell but absent or inaccessible on a non-tumor cell.

EXAMPLES

Figure 5:
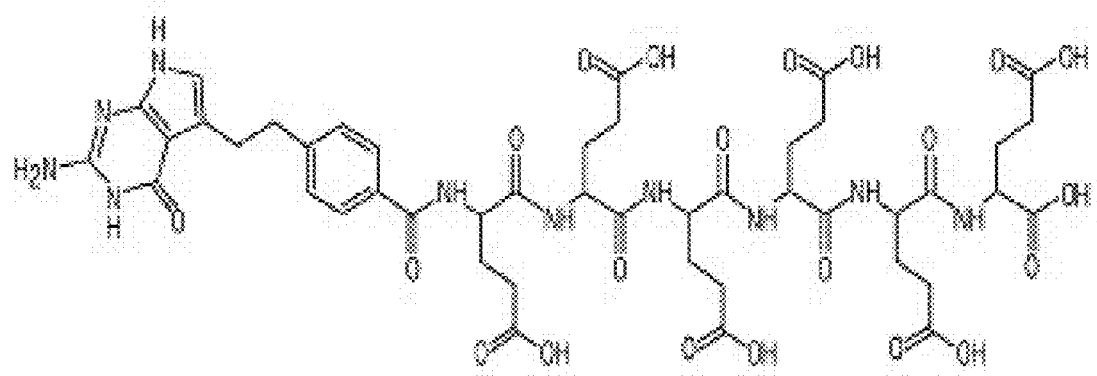
FIG. 5 shows chemical formula of alpha pentaglutamate and hexaglutamate pemetrexed.

The following examples are intended to illustrate but not to limit the disclosure in any manner, shape, or form, either explicitly or implicitly. While they are typical of those that might be used, other procedures, methodologies, or techniques known to those skilled in the art may alternatively be used. The example compositions comprise example liposomes. Both example composition and example liposome are used in the experiments described in the examples section and throughout this disclosure are specific embodiments, of the disclosure and are not meant to define the full scope of the disclosure. FIG. 5 shows chemical formula of alpha pentaglutamate and hexaglutamate pemetrexed. FIG. 6 shows chemical formulae of exemplary L-gamma pentaglutamated and hexaglutamate antifolate compositions encompassed by the disclosure.

Methods
Production of Hexaglutamated Pemetrexed (HGP) Liposomes

Briefly Gamma HGP (gG6) was encapsulated in liposomes by the following procedure. First, the lipid components of the liposome membrane were weighed out and combined as a concentrated solution in ethanol at a temperature of around 65° C. In this example, the lipids used were hydrogenated soy phosphatidylcholine, cholesterol, and DSPE-PEG-2000 (1,2-distearoyl-sn-glycero-3-phosphoethanolamine-N-[methoxy(polyethylene glycol)-2000]). The molar ratio of HSPC:Cholesterol: PEG-DSPE was approximately 3:2:0.15. Next, gG6 was dissolved in an aqueous buffer at a concentration of 20 mg/mi with a pH of 6.5-6.9. The drug solution was heated up to 65° C. The ethanolic lipid solution was injected into the gG6 solution using a small bore needle. During this step the drug solution was well stirred using a magnetic stirrer. The mixing was performed at an elevated temperature (63° C.-72° C.) to ensure that the lipids were in the liquid crystalline state (as opposed to the gel state that they attain at temperatures below the lipid transition temperature Tm=51° C.-54° C.). As a result, the lipids were hydrated and form multiple bilayer (multilamellar) vesicles (MLV) containing gG6 in the aqueous core.

Downsizing of MLV's Using Filter Extrusion

The MLVs were fragmented into unilamellar (single bilayer) vesicles of the desired size by high-pressure extrusion using two passes through stacked (track-etched polycarbonate) membranes. The stacked membranes had two layers with a pore size of 200 nm and six layers with a pore size of 100 nm. During extrusion, the temperature was maintained above the Tm to ensure plasticity of the lipid membranes. As a result of the extrusion, large and heterogeneous in size and lamellarity MLVs turned into small, homogenous (100-120 nm) unilamellar vesicles (ULV) that sequestered the drug in their interior. A Malvern Zetasizer Nano ZS instrument (Southborough, Mass.) with back scattering detector (90°) was used for measuring the hydrodynamic size (diameter) at 25° C. in a quartz micro cuvette. The samples were diluted 50-fold in formulation matrix before analysis.

Purification of Liposomes

After the ULV's containing gG6 had been produced, the extra-liposomal gG6 was removed using columns for small volume or tangential flow diafiltration against a suitable buffer for large volume. Although any buffer solution can be used, in this example the buffer used was 5 mM HEPES, 145 mM Sodium Chloride, pH 6.7. Upon completion of purification, filter sterilization was performed using a 0.22 micron filter.

Antibody Conjugation

Activated liposomes were prepared by adding DSPE-PEG-maleimide to the lipid composition. The liposomes contained four different lipids: hydrogenated soy phosphatidylcholine (HSPC), cholesterol, 1,2-distearoyl-sn-glycero-3-phosphoethanolamine-N-[methoxy(polyethylene glycol)-2000] (DSPE-PEG-2000), and 1,2-distearoyl-sn-glycero-3-phosphoethanolamine-N-[maleimide (polyethylene glycol)-2000] (DSPE-PEG-maleimide), in ratios of 3:2:0.1125: 0.0375.

Antibody thiolation was accomplished through use of Traut's reagent (2-iminothiolane) to attach a sulfhydryl group onto primary amines. Antibodies were suspended in PBS at a concentration of 0.9-1.6 mg/ml. Traut's reagent (14 mM) was added to antibody solution at a final concentration of 1-5 mM and then removed through dialysis after one-hour incubation at room temperature. Thiolated antibody was added to activated liposome at a ratio of 60 g/mol phosphate lipids, and the reaction mixture was incubated for one hour at room temperature and over-night at 4 uL-cysteine was used to terminate the reaction and unconjugated antibodies were removed through dialysis.

Physical Characteristics of the Nanoparticles

|  | Starting con. | Encapsulation efficiency | Final con. | Drug/Lipid Ratio | Diameter | PDI | Zeta potential |
|---|---|---|---|---|---|---|---|
| Lps aDG6 | 1 mg/ml | 4.75% | 0.031 mg/ml | 25-30 g/mM lipids | 122.8 nm | 0.021 | −1.14 mV |
| Lps gDG6 | 1 mg/ml | 5.71% | 0.038 mg/ml | 25-30 g/mM lipids | 103.8 nm | 0.017 | −1.77 mV |
| Lps aG6 | 1 mg/ml | 5.90% | 0.039 mg/ml | 25-30 g/mM lipids | 100.2 nm | 0.018 | −1.90 mV |
| Lps gG6 | 20 mg/ml | 10.60% | 1.39 mg/ml | 35-50 g/mM lipids | 114.9 nm | 0.035 | −1.76 mV |

Dose Response Study of HGP (Hexaglutamated Pemetrexed) and Liposomes

Cell viability was determined by CellTiter-Glo®(CTG) luminescent cell viability assay on Day 3 (48 hour) and Day 4 (72 hour). This assay determines the number of viable cells in culture based on quantifying ATP that is present within, which in turn signals the presence of metabolically active cells. The CTG assay uses luciferase as a readout. To assess cell viability Dose response inhibition of pemetrexed, HGP and liposomes on different cancer cell growth were investigated using CellTiter-Glo® luminescent cell viability assay. Human cancer cells were harvested, counted and plated at a same cell density on Day 0. A series of 8 dilutions of each test article were added to the cells on Day 1. Dose response curve were generated and fit using GraphPad Prism and IC50 of each test article were calculated. A lower the IC50 is, the more potent the test article is in term of cancer cell growth inhibition.

Cells were seeded into 96-well plate at a cell density of 5×104 cells per well in 100 μl of fresh media on Day 0. Eight serial 2-fold dilutions of each test article in culture medium were generated and added to cells in triplicate on Day 1. In addition, three wells of cells were treated with vehicle (HBS for free drug or empty liposome for liposomal HGP) alone as a control.

On Days 3 and 4, 100 μl of CellTiterGlo® Reagent were added to each well and incubated at room temperature for 15 minutes. Luciferase luminescence were recorded for each well. In addition, 8 serial 2-fold dilutions of the vehicle (HBS or empty liposome) in culture medium were added into empty wells and included in the assay to generate the background luminescence signals. Luciferase signals were normalized by subtracting the background luminescence signal out of the read-outs respectively.

Human Normal Primary Bone Marrow CD34+ Cells were obtained from ATCC. (ATCC Catalog Number PCS-800-012). Cells were thawed at 37° C. for 1 minute and then placed on ice. The cells were then resuspended in StemSpan SFEM (Stem Cell Tech Catalog Number 9650) plus 10% heat inactivated fetal bovine serum (Corning 35-015-CV). The cells were plated into 96 well culture plates at a density of 2.5×104 cells/well. The following day, live cells were collected via centrifugation and resuspended in neutrophil growth media (StemSpan SFEM plus 10% Heat Inactivated fetal bovine serum plus 100 ng/ml human stem cell factor (Sigma Catalog Number H8416), 20 ng/ml human granulocyte colony-stimulation factor (Sigma Catalog Number H5541), and long/ml human recombinant IL3 (Sigma SRP3090) at a density of 2.5×104 cells/well. Cells were incubated at 37° C. for 10 days. Fresh media was added every two days. Mature neutrophils were then collected and plated in 96 well plates at a density of 1×104 cells/well and incubated at 37° C. overnight. The next day, test article or vehicle was resuspended in neutrophil growth media and added to the plates. The cells were then incubated for either 48 hours or 72 hours at 37° C. and then assayed at each time point using the Cell Titer Glo Assay (Promega Catalog #G7572).

Methodologies used for cell line AML12 (non-cancerous liver cells) and CCD841 (non-cancerous colon epithelial cells) are similar to the methods used for cancer cells.

Results

FIG. 5 shows chemical formula of alpha pentaglutamate and hexaglutamate pemetrexed.

FIG. 6 shows chemical formulae of exemplary L-gamma pentaglutamate and hexaglutamate antifolate compositions encompassed by the disclosure.

In a set of dose response experiments, 6 cell lines representing different types of cancers, namely HT-29 (colon cancer), H2342 (NSCLC, adenocarcinoma subtype), H292 (NSCLC, adenocarcinoma subtype), SW620 (CRC), H1806 (triple negative breast cancer) and OAW28 (ovarian cancer), were studied (FIG. 7). Treatment consisted of exposure for 48 hours using 4 different encapsulated derivatives of liposomal pemetrexed hexaglutamate (liposomal gG6), namely liposomal gamma hexaglutamate (liposomal gG6) its mirror image liposomal gamma-D hexaglutamate (liposomal gDG6), also referred to as its corresponding enantiomer, and liposomal alpha hexaglutamate (liposomal aG6) and its mirror image, liposomal alpha-D hexaglutamate (liposomal aDG6) also referred to as its corresponding enantiomer.

The relative potency of all of the above mentioned derivatives as compared to pemetrexed, following exposure over 48 hours, is represented in FIG. 7. The relative potency of treatment using the various derivatives, as shown in this figure was calculated by dividing the IC50 of pemetrexed by the IC50 of liposomal pemetrexed hexaglutamate for each cell line. As shown in this figure, in all cell lines, the potency of liposomal pemetrexed hexaglutamate well exceeded that of pemetrexed. By way of example, consider the NSCLC cell line H292. As shown in the figure, the potency of liposomal pemetrexed hexaglutamate ranged from 25-fold to ≥50-fold that of pemetrexed. This suggests that a 4% or lower dose of the liposomal pemetrexed hexaglutamate would have the same treatment effect as a 100% dose of pemetrexed.

Cancer cell viability studies comparing liposomal pemetrexed hexaglutamate (liposomal gG6/Lps Hexa gG6) and pemetrexed for cytotoxic activity on representative cell lines in breast, lung and ovarian cancer are shown in FIGS. 8-10. These data show that liposomal pemetrexed hexaglutamate is more potent than pemetrexed. Further, as an indicator of efficacy, the results of the experiments on the same cell lines depicted at various dose levels ranging from 16 to 128 nM in FIGS. 11-13. As shown in these figures, at each of these dose ranges, liposomal pemetrexed hexaglutamate is superior to pemetrexed in terms of inhibiting cancer cells for the lung and breast cancer cell lines. In the ovarian cancer cell line, pemetrexed at the dose of 128 nM, appears to be equally effective as liposomal pemetrexed hexaglutamate, whereas the liposomal pemetrexed hexaglutamate at the dose of 32 nM and 64 nM has a better treatment effect than pemetrexed; at 16 nM the treatment effect is lower and similar in magnitude for liposomal pemetrexed hexaglutamate and pemetrexed.

The major toxicities seen in patients treated with pemetrexed is bone marrow suppression which manifests as a decrease in blood counts including neutrophil counts (a type of white blood cells). There is also some adverse effect on the lining of the mouth and gut that manifests as diarrhea and mucositis, as well as an adverse effect on the liver in some instances. To assess the above-mentioned toxicities, treatment liposomal pemetrexed hexaglutamate and pemetrexed was measured at 48 hours on CD34+ cells that were differentiated into neutrophils, CCD841 colon epithelium cells and AML12 liver cells. As shown in FIG. 14, liposomal pemetrexed hexaglutamate is significantly less toxic to differentiating human neutrophils in contrast to pemetrexed. This is also supported by neutrophil counts that are better preserved following treatment with the derivatives compared to pemetrexed, at dose ranges from 16 nM to 128 nM (FIG. 15). Strikingly, there does not appear to be any toxicity to the liver cells following treatment with liposomal pemetrexed hexaglutamate at the dose levels studied (FIG. 16). In contrast, pemetrexed at all doses studied is leading to a reduction in the liver cell counts of approximately 40%. And finally, the same trend is seen following treatment of epithelial colon cells (FIG. 17). As shown in this figure, pemetrexed at all doses studied is leading to approximately a ≥50% decrease in the number of cells compared to approximately a 20% or less decrease after treatment with liposomal pemetrexed hexaglutamate.

In a non-limiting example embodiment of this disclosure, there is provided a composition comprising alpha (L-alpha or D-alpha) or D-gamma polyglutamated antifolate.

In the composition of the immediately preceding paragraph, the composition may comprise pentaglutamated or hexaglutamated antifolate.

In the composition of any of the preceding two paragraphs, the alpha (L-alpha or D-alpha) or D-gamma polyglutamated antifolate may be one or more members selected from the group consisting of: polyglutamated methotrexate (MTX), polyglutamated pemetrexed (PMX), polyglutamated lometrexol (LTX), polyglutamated AG2034, polyglutamated raltitrexed (RTX), polyglutamated piritrexim, polyglutamated pralatrexate, polyglutamated AG2034, polyglutamated GW1843, polyglutamated aminopterin, and polyglutamated LY309887.

In the composition of any of the preceding three paragraphs, the composition may comprise alpha (L-alpha or D-alpha) or D-gamma polyglutamated antifolate which may be polyglutamated PMX, MTX, RTX, or LTX.

In the composition of any of the preceding four paragraphs, the composition may comprise alpha (L-alpha or D-alpha) or D-gamma polyglutamated antifolate which may include pentaglutamated or hexaglutamated antifolate.

In the composition of any of the preceding five paragraphs, the composition may comprise alpha (L-alpha or D-alpha) or D-gamma polyglutamated antifolate which may include pentaglutamated or hexaglutamated PMX, MTX, RTX, and/or LTX.

A non-limiting example liposomal alpha (L-alpha or D-alpha) or D-gamma polyglutamated antifolate (LPA) composition may comprise a composition of any of the preceding six paragraphs and the liposome may be optionally pegylated (PLPA).

In the LPA or PLPA composition of the immediately preceding paragraph, the alpha (L-alpha or D-alpha) or D-gamma polyglutamated antifolate may include pentaglutamated or hexaglutamated antifolate.

In the LPA or PLPA composition of any of the preceding two paragraphs, the alpha (L-alpha or D-alpha) or D-gamma polyglutamated antifolate may be one or more members selected from the group consisting of: alpha (L-alpha or D-alpha) or D-gamma polyglutamated methotrexate (MTX), polyglutamated pemetrexed (PMX), polyglutamated lometrexol (LTX), polyglutamated AG2034, polyglutamated raltitrexed (RTX), polyglutamated piritrexim, polyglutamated pralatrexate, polyglutamated AG2034, polyglutamated GW1843, polyglutamated aminopterin, and polyglutamated LY309887.

In the LPA or PLPA composition of any of the preceding three paragraphs the alpha (L-alpha or D-alpha) or D-gamma polyglutamated antifolate is polyglutamated PMX, MTX, RTX, and/or LTX.

In the LPA or PLPA composition of any of the preceding four paragraphs, the alpha (L-alpha or D-alpha) or D-gamma polyglutamated antifolate may include a pentaglutamated or hexaglutamated antifolate.

In the LPA or PLPA composition of any of the preceding five paragraphs, the alpha (L-alpha or D-alpha) or D-gamma polyglutamated antifolate may include pentaglutamated or hexaglutamated PMX, MTX, RTX, and/or LTX.

In the LPA or PLPA composition of any of the preceding six paragraphs, the liposome may be anionic or neutral.

In the LPA or PLPA composition of any of the preceding seven paragraphs, a targeting moiety may be attached to one or both of a PEG and the exterior of the liposome, and the targeting moiety may have a specific affinity for a surface antigen on a target cell of interest.

In the LPA or PLPA composition of any of the preceding eight paragraphs, a targeting moiety may be attached to one or both of a PEG and the exterior of the liposome and may be a polypeptide.

In the LPA or PLPA composition of any of the preceding nine paragraphs, a targeting moiety may be attached to one or both a PEG and the exterior of the liposome and may be an antibody or a fragment of an antibody.

In the LPA or PLPA composition of any of the preceding ten paragraphs, one or more of an immunostimulatory agent, a detectable marker and a maleimide may be disposed on at least one of a PEG and the exterior of the liposome.

In the LPA or PLPA composition of any of the preceding eleven paragraphs, a polypeptide may bind an antigen with an equilibrium dissociation constant (Kd) in a range of $0.5 \times 10^{-10}$ to $10 \times 10^{-6}$ as determined using BIACORE analysis.

In the LPA or PLPA composition of any of the preceding twelve paragraphs, a polypeptide may specifically bind one or more folate receptors selected from the group consisting of: folate receptor alpha (FR-α), folate receptor beta (FR-β), and folate receptor delta (FR-δ).

A non-limiting example method of killing a hyperproliferative cell may include contacting a hyperproliferative cell with a liposomal alpha (L-alpha or D-alpha) or D-gamma polyglutamated antifolate composition of any of the preceding thirteen paragraphs.

In the method of the immediately preceding paragraph, the hyperproliferative cell may be a cancer cell.

A non-limiting example method for treating cancer may comprise administering an effective amount of the alpha (L-alpha or D-alpha) or D-gamma polyglutamated antifolate composition of any of paragraphs [0321]-[0339] to a subject having or at risk of having cancer.

In the method of the immediately preceding paragraph, the cancer may be one or more selected from the group consisting of: lung cancer, pancreatic, breast cancer, ovarian cancer, lung cancer, prostate cancer, head and neck cancer, gastric cancer, gastrointestinal cancer, colon cancer, esophageal cancer, cervical cancer, kidney cancer, biliary duct cancer, gallbladder cancer, and a hematologic malignancy.

A non-limiting example maintenance therapy for subjects that are undergoing or have undergone cancer therapy may include administering an effective amount of the alpha (L-alpha or D-alpha) or D-gamma polyglutamated antifolate composition of any of paragraphs [0321]-[0339] to a subject that is undergoing or has undergone cancer therapy.

A non-limiting example pharmaceutical composition may include the alpha (L-alpha or D-alpha) or D-gamma polyglutamated antifolate composition of any of paragraphs [0321]-[0339].

A non-limiting example method for treating a disorder of the immune system may include administering an effective amount of the alpha (L-alpha or D-alpha) or D-gamma polyglutamated antifolate composition of any of paragraphs [0321]-[0339] to a subject having or at risk of having a disorder of the immune system.

A non-limiting example method for treating an infectious may include comprises administering an effective amount of the alpha (L-alpha or D-alpha) or D-gamma polyglutamated antifolate composition of any of paragraphs [0321]-[0339] to a subject having or at risk of having an infectious disease.

A non-limiting example method of delivering alpha (L-alpha or D-alpha) or D-gamma polyglutamated antifolate to a tumor expressing a folate receptor on its surface may include administering a polyglutamated antifolate composition of any of paragraphs [0321]-[0339] to a subject having the tumor in an amount to deliver a therapeutically effective dose of the alpha (L-alpha or D-alpha) or D-gamma polyglutamated antifolate to the tumor.

A non-limiting example method of preparing a liposomal alpha (L-alpha or D-alpha) or D-gamma polyglutamated antifolate composition which may include alpha (L-alpha or D-alpha) or D-gamma polyglutamated antifolate composition of any of paragraphs [0321]-[0339] includes forming a mixture comprising: liposomal components; alpha (L-alpha or D-alpha) or D-gamma polyglutamated antifolate in solution; homogenizing the mixture to form liposomes in the solution; and processing the mixture to form liposomes containing the polyglutamated antifolate.

A non-limiting example pharmaceutical composition may include an alpha (L-alpha or D-alpha) or D-gamma polyglutamated antifolate composition of any of paragraphs [0321]-[0339].

Although the disclosure has been described with reference to various some embodiments, it should be understood that various modifications can be made without departing from the spirit of the disclosure. Accordingly, the scope of the disclosure should be determined with reference to the appended claims, along with the full scope of equivalents to which such claims are entitled. The disclosures of all cited articles and references, including patent applications and publications, are incorporated herein by reference for all purposes.

Various new chemical entities, methods and equipment for making these chemical entities are set forth below in the appended claims.

What is claimed is:

1. A liposomal composition comprising polyglutamated pemetrexed (PMX) encapsulated by a pegylated liposome, wherein the polyglutamated PMX comprises at least 3 glutamate residues linked by alpha carboxyl group linkages wherein the liposome has a diameter in the range of 20 nm to 200 nm and wherein the liposome does not contain a targeting moiety having specific affinity for a surface antigen on a target cell.

2. The liposomal composition of claim 1, wherein the polyglutamated PMX comprises 3, 4, 5, 6, 7, 8, 9, or 4-10 glutamate residues linked by alpha carboxyl group linkages.

3. The liposomal composition of claim 1, wherein the polyglutamated PMX comprises 2, 3, 4, 5, 6, 7, 8, 9, or 4-10 D-glutamate residues linked by alpha carboxyl group linkages.

4. The liposomal composition of claim 1, wherein the polyglutamated PMX comprises pentaglutamated PMX.

5. The liposomal composition of claim 1, wherein the polyglutamated PMX comprises hexaglutamated PMX.

6. The liposomal composition of claim 1, wherein the liposome has a diameter in the range of 50 nm to 150 nm or 80 nm to 120 nm.

7. The liposomal composition of claim 1, wherein the liposome is formed from liposomal components and wherein: the liposomal components comprise:
   (a) at least one of an anionic lipid and a neutral lipid;
   (b) at least one member selected from the group consisting of: DSPE; DSPE-PEG; DSPE-PEG-maleimide; HSPC; HSPC-PEG; cholesterol; cholesterol-PEG; and cholesterol-maleimide; or
   (c) at least one selected from the group consisting of: DSPE; DSPE-PEG-FITC; DSPE-PEG-maleimide; cholesterol; and HSPC.

8. The liposomal composition of claim 7, wherein one or more liposomal components further comprises at least one steric stabilizer selected from the group consisting of polyethylene glycol (PEG); poly-L-lysine (PLL); monosialoganglioside (GM1); poly(vinyl pyrrolidone) (PVP); poly(acrylamide) (PAA); poly(2-methyl-2-oxazoline); poly(2-ethyl-2-oxazoline); phosphatidyl polyglycerol; poly [N-(2-hydroxypropyl) methacrylamide]; amphiphilic poly-N-vinylpyrrolidones; L-amino-acid-based polymer; or polyvinyl alcohol.

9. The liposomal composition of claim 1, wherein the PEG of the liposome has a number average molecular weight (Mn) of 200 to 5000 daltons.

10. The liposomal composition of claim 1, wherein the liposome:
   (a) is anionic or neutral,
   (b) has a zeta potential that is less than or equal to zero,
   (c) has a zeta potential that is between 0 to −150 mV, or
   (d) has a zeta potential that is between −30 to −50 mV.

11. The liposomal composition of claim 1, wherein the liposome has an interior space and the interior space comprises the polyglutamated PMX and an aqueous pharmaceutically acceptable carrier, optionally wherein the aqueous pharmaceutically acceptable carrier (a) is trehalose, or (b) comprises citrate buffer at a concentration of between 5 to 200 mM and a pH of between 2.8 to 6.

12. The liposomal composition of claim 1, wherein the liposome comprises less than 200,000 molecules or between 10,000 to 100,000 molecules of polyglutamated PMX.

13. The liposomal composition of claim 1, wherein the polyglutamated PMX is at a pH of 5-8.

14. The liposomal composition of claim 1, further comprising one or more of an immunostimulating agent, a detectable marker and a maleimide disposed on at least one of the PEG and the exterior of the liposome.

15. The liposomal composition of claim 1, further comprising one or more of an immunostimulating agent, a detectable marker and a maleimide, wherein the immunostimulating agent, the detectable marker or the maleimide is attached to said PEG or the exterior of the liposome.

16. The liposomal composition of claim 15, wherein the immunostimulating agent is at least one selected from the group consisting of: a fluorescein; a fluorescein isothiocyanate (FITC); a dinitrophenol (DNP); a beta glucan; a beta-1,3-glucan; and a beta-1,6-glucan.

17. The liposomal composition of claim 1, further comprising a hapten or at least one cryoprotectant selected from the group consisting of mannitol; trehalose; sorbitol; and sucrose.

18. The liposomal composition of claim 1, which is in unit dosage form.

19. A pharmaceutical composition comprising the liposomal composition of claim 1.

* * * * *